(12) United States Patent
Buelow et al.

(10) Patent No.: US 7,129,084 B2
(45) Date of Patent: Oct. 31, 2006

(54) PRODUCTION OF HUMANIZED ANTIBODIES IN TRANSGENIC ANIMALS

(75) Inventors: Roland Buelow, Palo Alto, CA (US); Josef Platzer, Munich (DE); Wim van Schooten, Sunnyvale, CA (US); Jens-Ulrich Buelow, Karlsruhe (DE)

(73) Assignee: Therapeutic Human Polyclonals, Inc., Mountain View, CA (US)

( * ) Notice: Subject to any disclaimer, the term of this patent is extended or adjusted under 35 U.S.C. 154(b) by 52 days.

(21) Appl. No.: 09/921,819

(22) Filed: Aug. 3, 2001

(65) Prior Publication Data

US 2003/0017534 A1   Jan. 23, 2003

Related U.S. Application Data

(60) Provisional application No. 60/222,872, filed on Aug. 3, 2000, provisional application No. 60/276,156, filed on Mar. 15, 2001.

(51) Int. Cl.
   *C12N 15/00* (2006.01)
   *C12N 15/63* (2006.01)
   *C12N 15/64* (2006.01)

(52) U.S. Cl. .................. 435/320.1; 435/455; 435/463; 435/326

(58) Field of Classification Search ............. 435/320.1, 435/455, 325
See application file for complete search history.

(56) References Cited

U.S. PATENT DOCUMENTS

| | | | |
|---|---|---|---|
| 5,202,238 A * | 4/1993 | Fell et al. ................... | 435/69.6 |
| 5,416,260 A | 5/1995 | Koller et al. | |
| 5,453,357 A | 9/1995 | Hogan | |
| 5,545,807 A | 8/1996 | Surani et al. | |
| 5,567,607 A | 10/1996 | Zhao et al. | |
| 5,569,825 A * | 10/1996 | Lonberg et al. ............... | 800/18 |
| 5,570,429 A | 10/1996 | Paddock | |
| 5,639,457 A | 6/1997 | Brem et al. | |
| 5,814,318 A | 9/1998 | Lonberg et al. | |
| 5,874,299 A | 2/1999 | Lonberg et al. | |
| 6,180,400 B1 | 1/2001 | Kuwana et al. ............. | 435/325 |
| 2002/0028488 A1* | 3/2002 | Singh ...................... | 435/70.21 |

FOREIGN PATENT DOCUMENTS

| | | |
|---|---|---|
| AU | 199655310 B2 | 5/1996 |
| CA | 2034034 | 7/1991 |
| CA | 2043088 | 1/1992 |
| EP | 0438474 B1 | 7/1991 |
| EP | 0438474 B1 | 5/1996 |
| GB | 2245589 A | 1/1992 |
| GB | 2282139 A | 3/1995 |
| GB | 2318578 B | 4/1998 |
| GB | 2331751 B | 6/1999 |
| JP | H6-16698 | 6/1994 |
| WO | WO9004036 | 4/1990 |
| WO | WO9323528 | 11/1993 |
| WO | WO9407997 | 4/1994 |
| WO | WO9418344 | 8/1994 |
| WO | WO9508625 | 3/1995 |
| WO | WO9510599 | 4/1995 |
| WO | WO9514376 | 6/1995 |
| WO | WO9517516 | 6/1995 |
| WO | WO9520042 | 7/1995 |
| WO | WO9607732 | 3/1996 |
| WO | WO 9612793 | 5/1996 |
| WO | WO 96/30498 | 10/1996 |
| WO | WO9630498 | 10/1996 |
| WO | WO9707668 | 3/1997 |
| WO | WO9707669 | 3/1997 |
| WO | WO 97/18703 | 5/1997 |
| WO | WO 9737009 | 10/1997 |
| WO | WO 9807841 | 2/1998 |
| WO | WO9816630 | 4/1998 |
| WO | WO9829532 | 7/1998 |
| WO | WO 9830683 | 7/1998 |
| WO | WO9837183 | 8/1998 |
| WO | WO9841615 | 9/1998 |
| WO | WO9857538 | 12/1998 |
| WO | WO 9901163 | 1/1999 |
| WO | WO 9901164 | 1/1999 |
| WO | WO 9906534 | 2/1999 |
| WO | WO 99/10505 | 3/1999 |
| WO | WO9921415 | 5/1999 |
| WO | WO 9937143 | 7/1999 |
| WO | WO9940213 | 8/1999 |
| WO | WO 00/46251 | 8/2000 |
| WO | WO 00/75300 A2 | 12/2000 |

(Continued)

OTHER PUBLICATIONS

Rader et al. (2000) J. Biol. Chem., vol. 275, No. 18, 13668-13676.*

(Continued)

*Primary Examiner*—Anne Marie Wehbé
(74) *Attorney, Agent, or Firm*—Ginger R. Dreger, Esq.; Heller Ehrman, LLP

(57) ABSTRACT

This invention relates to humanized antibodies and antibody preparations produced from transgenic non-human animals. The non-human animals are genetically engineered to contain one or more humanized immunoglobulin loci which are capable of undergoing gene rearrangement and gene conversion in the transgenic non-human animals to produce diversified humanized immunoglobulins. The present invention further relates to novel sequences, recombination vectors and transgenic vectors useful for making these transgenic animals. The humanized antibodies of the present invention have minimal immunogenicity to humans and are appropriate for use in the therapeutic treatment of human subjects.

18 Claims, 21 Drawing Sheets

FOREIGN PATENT DOCUMENTS

WO      WO 01/19394      3/2001

OTHER PUBLICATIONS

Tsai et al. (2002) Int. Immunol., vol. 14 (1), 55-64.*
Knight, et al., "Organization and Polymorphism of Rabbit Immunoglobulin Heavy Chain Genes", *J. Immunol.*, pp. 1245-1250 (1985).
Huang and Stollar, "A Majority of Ig H.Chain, Cdna of Normal Human Adult Blood Lymphocytes Resembles cDNA for Fetal Ig and Natural Autoantibodies", *The American Assoc. of Immunology*, vol. 151, pp. 5290-5300 (1993).
Knight & Becker, "Molecular Basis of the Allelic Inheritance of Rabbit ImmunologyVH Allotypes: Implications for theGeneration of Antibody Diversity", *Cell*, vol. 60, pp. 963-970 (1990).
Pritsch, et al., "V Gene Usage by Seven Hybrids Derived From CD5+ B-Cell Chronic Lymphocytic Leukemia and Displaying Autoantibody Activity", *Blood*, vol. 82, No. 10, pp. 3103-3112 (1993).
Lautner-Rieske, et al., "The Human Immunoglobulin $\chi$ Locus, Characterization of the Duplicated A Regions*", *Eur. J. Immunol.*, vol. 22, No. 4, pp. 1023-1029 (1992).
Lieberman, et al., "Structure of a Germline Rabbit Immunoglobin $V_\chi$-Region Gene: Implications for Rabbit $V_\chi$-$J_\chi$ Recombination", *The Journal of Immunology*, vol. 133, No. 5, pp. 2753-2756 (1984).
Fan, et al., "Transgenic Rabbit Models for Biomedical Research: Current Status, Basic Methosd and Future Perspectives", *Pathology International*, vol. 49, No. 7, pp. 583-594 (1999).
Zhang, et al., "DNA Cloning by Homologous Recombinatio in *Escherichia coli*", *Nature Biotechnology*, vol. 18, No. 12, pp. 1314-1317 (2000).
Kametani, et al., "Comparitive Studies on the Structure of Light Chains of Human Immunoglobulins", *J. Biochem.*, vol. 93, No. 2, pp. 421-429 (1983).
McCormack et al., "Chicken IgL Rearrangement Involves Deletion of a Circular Episome and Addition of Single Nonrandom Nucleotides to Both Coding Segments", *Cell*, vol. 56, pp. 785-791 (1989).
Mattyssens and Rabbitts, "Structure and Arrangement of Human Heavy Chain Variable Region Genes", *The Immune System*, vol. 1, pp. 132-138 (1981).
Etches, et al., "Strategies for the Production of Transgenic Chickens", *Methods in Molecular Biology*, vol. 62, pp. 433-450.
Pain, et al., "Chicken Embryonic Stem Cells and Transgenic Strategies", *Cells Tissues, Organs*, vol. 165, No. 3-4, pp. 212-219 (1999).
Sang, et al., "Transgenic Chickens—Methods and Potential Applications", *TIBTECH*, vol. 12, pp. 415-420 (1994).
Brem, et al., "YAC Transgenesis in Farm Animals: Rescue of Albinism in Rabbits", *Molecular Reproduction & Development*, vol. 44, pp. 56-62 (1996).
Stice, et al., "Nuclear Reprogramming in Nuclear Transplant Rabbit Embryos", *Biology of Reproduction*, vol. 39, pp. 657-664 (1988).
McCartney-Francis, et al., "Expression of K2 Isotype mRNA in Normal and Basilea Rabbits", *Molecular Immunology*, vol. 24, No. 4, pp. 357-364 (1987).
Allegrucci, et al., "Preferential Rearrangement in Normal Rabbits of the 3' $V_{Ha}$ Allotype Gene that is Deleted in Alicia Mutants . . . ", *Eur. J. Immunol.*, vol. 21, pp. 411-417 (1991).
Frommel et al., "Metabolism of G and M Immunoglobulins in Normal and Hypogammaglobulinemic Chickens", *The Journal of Immunology*, vol. 105, No. 1, pp. 1-6 (1970).
Bendict, et al., "Inherited Immunodeficiency in Chickens: A Model for Common Variable Hypogammaglobulinemia in Man", *Adv. Exp. Med. Biol.*, vol. 88, No. 2, pp. 197-205 (1977).
T. Wakayama, et al., "Full-Term Development of Mice from Enucleated Oocytes Injected with Cumulus Cell Nuclei", *Nature*, vol. 394, No. 23, pp. 369-374 (1998).
Cibelli, et al., "Transgenic Boyine Chimeric Offspring Produced from Somatic Cell-Derived Stem-Like Cells", *Nature Bio Technology*, vol. 16, pp. 642-646 (1998).

Ishida, et al., "Production of a Diverse Repertoire of Human Antibodies in Genetically Engineered Mice", *Microbiol. Immunl.*, vol. 42, No. 3, pp. 143-150 (1998).
Tomizuka, et al., "Double Trans-Chromosomic Mice: Maintenance of Two Individual Human Chromosome Fragments Containing Ig Heavy and loci and Expression of Fully Human Antibodies", *National Academy of Sciences*, vol. 97, Issue 2, pp. 722-727 (2000).
Sale, et al., "Ablation of XRCC2/3 Transforms Immunoglobulin V Gene Conversion into Somatic Hypermutation", *Nature*, vol. 412 (2001).
Lanza, et al., "Extension of Cell Life-Span and Telomere Length in Animals Cloned from Senescent Somatic Cells", *Science*, vol. 288, pp. 665-669 (2000).
Polejaeva, et al., "Cloned Pigs Produced by Nuclear Transfer from Adult Somatic Cells", *Nature*, vol. 407, No. 7 (2000).
K.J. McCreath, et al., Production of Gene-Targeted Sheep by Nuclear Transfer from Cultured Somatic Cells, *Nature*, vol. 405 (2000).
D. Bucchini, et al., "Rearrangement of a Chicken Immunoglobulin Gene Occurs in the Lymphoid Lineage of Transgenic Mice", *Nature*, vol. 326, No. 26, pp. 409-411 (1987).
Knight, et al., "Generating the Antibody Repertoire in Rabbit", *Advances in Immunology*, vol. 56, pp. 179-218 (1994).
Langman, et al., "A Theory of the Ontogeny of the Chicken Huroral Immune System: The Consequences of Diversification by Gene Hyperconversion and its Extension to Rabbit", *Res. Immunology*, vol. 144, pp. 422-446 (1993).
Campbell, et al., "Sheep Cloned by Nuclear Transfer from a Cultural Cell Line", *Nature*, vol. 380, pp. 64-66 (1996).
Stice, et al., "Cloning: New Breakthroughs Leading to Commercial Opportunities", *Theriogenology*, vol. 49, pp. 129-138 (1998).
Cibelli, et al., "Cloned Transgenic Calves Produced from Nonquiescent Fetal Febroblasts", *Science*, vol. 280, pp. 1256-1258 (1998).
Schnieke, et al., "Human Factor IX Transgenic Sheep Produced by Transfer of Nuclei from Transfected Fetal Febroblasts", *Science*, vol. 278, pp. 2130-2133 (1997).
Akimenko, M.A., "Rabbit immunoglobin b9 C kappa light chain gene", Jun. 13, 1985.
Akimenko, M.A., "Complex allotypes of the rabbit immunoglobin kappa light chains are encoded by structural alleles", Nucleic Acids Research, vol. 12, No. 11, pp. 4691-4701, 1984.
Andris-Widhopf, J. et al., "Methods for the generation of chicken monoclonal antibody fragments by phage display", Journal of Immunological Methods, vol. 242, pp. 159-181, Aug. 28, 2000.
Butler, J E, "Immunoglobin diversity B-cell and antibody repertoire development in large farm animals", Revue Scientifique et Technique Office International Des Epizooties, vol. 17, No. 1, pp. 43-70, Apr. 1998.
Clarkson C.A., "O.aries mRNA for Ig gamma 2 constant region heavy chain", Database Accession No. X70983, Mar. 10, 1993.
Clarkson C.A., et al., Sequence of ovine Ig gamma-2 constant region heavy chain cDNA and molecular modeling of ruminant IgG isotypes, Molecular Immunology, vol. 30, No. 13, pp. 1195-1204, 1993.
Dreher, K. L., et al., "Rabbit IG Kappa-1B6 Gene Structure", Journal of Immunology, vol. 145, No. 1, pp. 325-330, Jul. 1, 1990.
Dufour, V., "O.aries mRNA for immunoglobin gammal chain secreted form", Database Accession No. X69797, Dec. 23, 1992.
Dufour, Vinciane, et al., "The Sheep Ig Variable Region Repertoire Consists of a single $V_H$ family", Journal of Immunology, vol. 156, No. 6, pp. 2163-2170, 1996.
Green, L.L., "Antibody engineering via genetic engineering of the mouse: XenoMouse strains are a vehicle for the facile generation of therapeutic human monoclonal antibodies", Journal of Immunological Methods, vol. 231, No. 1-2, pp. 11-23, Dec. 10, 1999.
Kacskovics, "Bos tauras IgG1 heavy chain constant region (IgCgamma) mRNA, partial cds", Database Accession No. S82409, Dec. 7, 1996.
Kacskovics, Imre et al., The Heterogeneity of Bovine IgG2: VIII. The Complete cDNA Sequence of Bovine IgG2a (A2) and an IgG1, Molecular Immunology, vol. 33, No. 2, pp. 189-195, 1996.

Jackson, T. et al., "B. tauras mRNA for Immunoglobin G1 heavy chain", Database Accesion No. X62916.1, Jun. 17, 1992.

Jackson, T. et al., "Nucleotiode Sequences and Expression of CDNAS for a Bovine Anti-Testosterone Monoclonal IGG1 Antibody", Molecular Immunology, vol. 29, No. 5, pp. 667-676, 1992.

Mariame, B. et al., "Interallelic and intergenic conversion events could induce differential evolution of the two rabbit immunoglobin kappa light chain genes", Nucleic Acids Research, vol. 15, No. 15, Aug. 11, 1987.

Martens, C.L. et al., "Oryctolagus cuniculus Ig gamma H-chain C-region gene, partial cds", Database Accession No. L29172, Mar. 2, 1994.

Martens, C.L., "Molecular Genetic Analysis of Genes Encoding the Heavy Chains of Rabbit Immunoglobin G", Journal of Immunology, vol. 133, No. 2, pp. 1022-1027, 1984.

Rader, C et al., "The Rabbit Antibody Repertoire as a Novel Source for the Generation of Therapeutic Human Antibodies", Journal of Biological Chemistry, vol. 275, No. 18, pp. 13668-13776, May 5, 2000.

Symons et al., "Bovine Ig germline heavy chain gamma-2-chain gene C-region, 3' end", Database Accession No. X16702, Nov. 23, 1989.

Symons et al., "Structure of Bovine Immunoglobin Constant Region Heavy Chain Gamma 1 and Gamma 2 Genes", Molecular Immunology, vol. 26, No. 9, pp. 841-850, 1989.

Taki, Shinsuke et al., "Targeted insertion of a variable region gene inot the immunoglobin heavy chain locus", Science, vol. 262, No. 5137, pp. 1268-1271, 1993.

Weidle U H et al., "Genes Encoding a Mouse Monoclonal Antibody Are Expressed in Transgenic Mice, Rabbits and Pigs", Gene, vol. 98, No. 2, pp. 185-191, Feb. 15, 1991.

Winstead, C. R. et al., "Antigen-induced somatic diversification of rabbit IgH genes: gene conversion and point mutation", Journal of Immunology, vol. 162, No. 11, Jun. 1, 1999.

Yarnold, S. et al., "Chimerization of Antitumor Antibodies via Homolgous Recombination Conversion Vectors", Cancer Research, American Association for Cancer Research, vol. 54, No. 2, pp. 506-512, Jan. 15, 1994.

Zou, Yong-Rui et al., "Generation of a mouse strain that produces immunoglobin kappa chains with human constant regions", Science, vol. 262, No. 5137, pp. 1271-1274, 1993.

* cited by examiner

Figure 1(a)-(d). Novel nucleotide sequences 3'prime of the cow Cgamma gene
(Cow Cγ 3' flanking sequences). Primers are shown in shaded boxes. The 5'
primer is in CH3, and the 3' primer is in M1. The sequences of clone 11,
clone 3, and clone 5 are set forth in SEQ ID NO: 3, SEQ ID NO: 4 and SEQ ID
NO: 5, respectively.

```
                 1                                                          50
     clone11     CCTAC ACGTGTGTGG TGATGCACGA AACTTTACGG
      clone3     CCTAC ACGTGTGTGG TGATGCACGA GGCCCTGCAC
      clone5     CCTAC ACGTGTGTGG TGATGCACGA GGCCCTGCAC 151                                                       200
     clone11     AATCACTACA AAGAGAAGTC CACCTCGAGG TCTCCGGGTA AATGAGCCTC
      clone3     AATCACTACA CGCAGAAGTC CACCTCTAAG TCTGCGGGTA AATGAGCCTC
      clone5     AATCACTACA CGCAGAAGTC CACCTCTAAG TCTGCGGGTA AATGAGCCTC 201                                                       250
     clone11     GCGCCGCTGA TCTAGTGGAC GTTCCCTCAT CCACCCACCC CTCCCCCCAC
      clone3     ACGTCCCTGC ACCAGCAAGC CCTCACCCAG C......... ..CCACCCTC
      clone5     ACGTCCCTGC ACCAGCAAGC CCTCACCCAG C......... ..CCACCCTC 251                                                       300
     clone11     CCCGGGCTCC AGGTCCAGCC AGGGCGCCCT AGCCCCTCCC TGTGTGCATT
      clone3     CCCGGGCTCC AAGTCCAGCC AGGACGCCCT AGCCCCTCCC TGTGTGCATT
      clone5     CCCGGGCTCC AGGTCCAGCC AGGACGCCCT AGCCCCTCCC TGTGTGCATT 301                                                       350
     clone11     CCTCCTGGGC CGCCGTGAAT AAAGCACCCA GGCCGCCCTG GGACCCTGCA
      clone3     CCTCCTGGGC CGCCGTGAAT AAAGCACCCA GGCCACCCTG GGACCCTGCA
      clone5     CCTCCTGGGC CGCCGTGAAT AAAGCACCCA GGCCGCCCTG GGACCCTGCA 351                                                       400
     clone11     ACGCTGTGCT GGTTCTTTCC GAGGCAGAGC CCTGGTGGCC GCCAGGCCTG
      clone3     ACGCTGTGCT GGTTCTTTCC GAGGCAGAGC CCTGGTGGCC GCCAGGCCTG
      clone5     ACGCTGTGCT GGTTCTTTCC GAGGCAGAGC CCTGGTGGCC GCCAGGCCTG 401                                                       450
     clone11     CGGGGGTGGG CTGAGCCGAC TCTGGGCCAC TTTGTTCAGC ATCTGTGGGG
      clone3     CAGGGGTGGG CTGAGCCGAC TCTGGGCCAC TTTGTTCAGC ATCTGTGGGG
      clone5     CGGGGGTGGG CTGAGCCGAC TCTGGGCCAC TTTGTTCAGC ATCTGTGGGG 451                                                       500
     clone11     GAGCTGACCC CACTCCGGGC CAGACACACA GTGAGTGGGT CCAGCAGGCC
      clone3     GAGCTGACCC CGCTCCGGGC CAGACACACA GTGAGTGGGT CCAGCAGGCC
      clone5     GAGCTGACCC CACTCCGGGC CAGACACACA GTGAGTGGGT CCAGCAGGCC 501                                                       550
     clone11     ACCTGGGGGC TGCCCAAGGC CACAGAGGGG CTTGGCCAGA GGCACAGCTC
      clone3     ACCTGGGGGC TGCCCGAGGC CACGGAGGGG CTTGGCCAGA GGCGTACCTC
      clone5     ACCTGGGGGC TGCCCAAGGC CACAGAGGGG CTTGGCCAGA GGCACAGCTC
```

Figure 1(a)

```
               551                                                         600
    clone11    CACGGTCCCC TCCAGCCACC ACCTGCTGGG CCGGCCTCTG GACAGGAACC
     clone3    CACGGCCCCC TCCAGCCACC ACCTGCTGGG CCGGCCTCTG GACAGGAACC
     clone5    CACGGTCCCC TCCAGCCACC ACCTGCTGGG CCGGCCTCTG GACAGGAACC 601                                                         650
    clone11    GGGGAAGCCC CCGAGACCCT CAGGGATTGA GGCCCAATGC TTCCCGCCTC
     clone3    GGGGAAGCCC CCGAGACCCT CAGGGATTGA GGCCCAATGC TTCCCGCCTC
     clone5    GGGGAAGCCC CCGAGACCCT CAGGGATTGA GGCCCAATGC TTCCCGCCTC 651                                                         700
    clone11    TGCTCCAGCC CACGCTGTGG GGCAGGGCCA CATCCTTGTC CCCAGGCCCC
     clone3    TGCTCCAGCC CACGCTGTGG GGCAGGGCCA CATCCTTGTC CCCAGGCCCC
     clone5    TGCTCCAGCC CACGCTGTGG GGCAGGGCCA CATCCTTGTC CCCAGGCCCC 701                                                         750
    clone11    TGTCCTTGGG TGTCCAGAGT CCTTGTGTCC ACTCTGGGCC TGCCTGGAGC
     clone3    TGTCCCTGGG TGCCCAGAGT CCTTGTGTCC ACTCTGGGCC TGCCTGGAGC
     clone5    TGTCCTTGGG TGTCCAGAGT CCTTGTGTCC ACTCTGGGCC TGCCTGGAGC 751                                                         800
    clone11    CACGCATGGC CAGGGGGTGG CCCTGCTTCA CCCTCAGGCT CCCAAGGTCA
     clone3    CACGCGTGGC CGGGGGATGG CCCTGCTCCA CCCTCAGGCT CCCAAGGTCA
     clone5    CACGCATGGC CAGGGGGTGG CCCTGCTTCA CCCTCAGGCT CCCAAGGTCA 801                                                         850
    clone11    GGCCTCGCCC TCCCTCGGCC AGGAGGCTCT GCCCGGCTCT CCCTGCCCAG
     clone3    GGCCTCGCCC TCCCTCAGCC AGGAGGCTCT GCCCGGCTCT CCCTGCCCAG
     clone5    GGCCTCGCCC TCCCTCGGCC AGGAGGCTCT GCCCGGCTCT CCCTGCCCAG 851                                                         900
    clone11    GGCCAGGCCT GTGCGCCCAT GGGGAGGTCA TCCCTGTGCC TGAAAGGGGT
     clone3    GGCCAGGCCT GTGCGCCCAT GGGGAGGTCA TCCCTGTGCC TGAAAGGGCT
     clone5    GGCCAGGCCT GTGCGCCCAT GGGGAGGTCA TCCCTGTGCC TGAAAGGGGT 901                                                         950
    clone11    CCAGGCCGAG AGCCCTGAAT GTCCAGGGCA GGGACCTAGC TGCTCCCTGT
     clone3    CCAGGCCGGG AGCCCTGAAT GTCCAGGGCA GGGACCTAGC TGCTCCCTGC
     clone5    CCAGGCCGAG AGCCCTGAAT GTCCAGGGCA GGGACCTAGC TGCTCCCTGT 951                                                         1000
    clone11    GGACACGGAG CCCAGAGCCA CAGACAACAA GCCCAGCCC CGCACGCACA
     clone3    AGACACGGAG CCCAGAGCCA CAGACAACAA GCCCAGCCC CGCACGCACA
     clone5    GGACACGGAG CCCAGAGCCA CAGACAACAA GCCCAGCCC CGCACGCACA 1001                                                        1050
    clone11    CGAGACAGCC CGCACCCAGC CTCCTCCACA CGCACTCAGG TGTACATGCG
     clone3    CAAGACAGCC CGCACCCAGC CTCCTCCACA CGCACTCAGG TGTGCATCCG
     clone5    CGAGACAGCC CACACCCCGC CTCCTCCACA CGCACTCAGG TGTGCATCCG
```

Figure 1(b)

```
             1051                                                    1100
clone11  CACATGAGCA CACTTCACCC CGTCACACCC ACACACCTAC ACACACTCAG
 clone3  CACATGAGCA CACTTCACCC CGTCACACCC ACACGCCTAC ACACACTCAG
 clone5  CACATGAGCA CACTTCACCC CATCACACCC ACACGCCTAC ACACACTCAG 1101                                                    1150
clone11  GTCTCGCACT CGGGGACCCA TGGGGTGACC CCACGGGCCC AGA.CCAGAG
 clone3  GTCTCGCACT CGGGGACCCA TGGGGTGACC CCACAGGCCC AGACCCAGAG
 clone5  GTCTCGCACT CGGGGACCCA TGGGGTGACC CCACAGGCCC AGACCCAGAG 1151                                                    1200
clone11  CTGGGTCTTG TGAGCCCTCC CTGTGGACAC CAGCTGGGCC CCACCCTCCA
 clone3  CTGGGTCTTG TGAGCCCTCC CTGTGGACAC CAGCTGGTCC CCACCCTCCA
 clone5  CTGGGTCTTG TGAGCCCTCC CTGTGGACAC CAGCTGGTCC CCACCCTCCA 1201                                                    1250
clone11  GCGCCCATGG GCTGCTCAGC GGCCCTTTCC CACACTGACC ACACTGACCA
 clone3  GCGCCCATGG GCTGCTCAGT GGCCCTTTCC CACACTGACC ACACTGACCA
 clone5  GCGCCCGTGG GCTGCTCAGC GGTCCTTTCC CACACTGACC ACACTGACCA 1251                                                    1300
clone11  GGTCAGACAT CCGTTCCTTG CCTCCCCTGG GACACCCACG CCCCTCCCTA
 clone3  GGTCAGACAT CCGTTCCTTG CCTCCCCTGG GGCACCCACG CCCCTCCCTA
 clone5  GGTCAGACAT CCGTTCCTTG CCTCCCCTGG GGCACCCATG CCCCTCCCTA 1301                                                    1350
clone11  GCAGGCTGAG ATCCCCCCTC AGCCCCTCGT CCTGGCAGCC TCACCCCTCG
 clone3  GCAGGCTGAG ATCCCCCCTC AGCCCCTCGT CCTGGCACCC TCACCCCTCA
 clone5  GCAGGCTGAG ATCCCCCCTC AGCCCCTCGT CCTGGCACCC TCACCCCTCA 1351                                                    1400
clone11  GGCACAGCAC CCCTCAGGCC CGGTGCTGTC AGCCCTCCCT CCCCGGGGGC
 clone3  GGCACAGGGA CAC...AGCC CGGCGCTGTC TGCCCTCCCT CCCTGGGGGC
 clone5  GGCACAGGGA CAC...AGCC CGGTGCTGTC TGCCCTCCCT CCCTGGGGGC 1401                                                    1450
clone11  AGGGCCCAGG AACGTGCGCT CTGCTGACCC TCCCAGCTCC AGGCCTGGCC
 clone3  AGGGCCCAGG CTCACATGCT CTGCTGACCC TCCCGGCTCC AGGCCTGGCC
 clone5  AGGGCCCAGG CTCACATGCT CTGCTGACCC TCCCAGCTCC AGGCCTGGCC 1451                                                    1500
clone11  CCCAGGGCAG AGGAGGCCAG GAACTGAGCC TCTGTCCTGT GGGGAGGTAG
 clone3  CCCAGGGCAG AGGAGGCCAG GAACTGAGCC TCTGTCCTGG GGGGAGGTGG
 clone5  CCCAGGGCAG AGGAGGCCAG GAACTGAGCC TCTGTCCTGG GGGGAGGTGG 1501                                                    1550
clone11  GGTCAGGGTC CCAGCTCAGG GCACAGCTCA GGATGGGAGC AGGACCCCAC
 clone3  GGTCAGGGCC CCAGCTCAGG GCACAGCTCA GGATGGGAAC AGGACACCAC
 clone5  GGTCAGGGCC CCAGCTCAGG GCACAGCTCA GGATGGGAGC AGGACACCAC
```

Figure 1(c)

```
             1551                                                     1600
clone11  AGGCCAGGCC CAGATAGCAG CCAGGGCTGG AGGGGTTGGG GCTGGGGCTG
 clone3  AGGCCAGGCC CAGACAGTGG CCAGGGCTGG AGGGGTGGGG TCTGGGGCTG
 clone5  AGGCCAGGCC CAGACAGTGG CCAGGGCTGG AGGGGTGGGG TCTGGGGCTG 1601                                                     1650
clone11  GGCCCCAGAG ACTGACCTCA GGTGACCCCT GCCTGGCCCA TGGGGAGATC
 clone3  GGGCCCAGAG ACTGACCTCA GGTGATCCCT GCCCAGCCCA TGGGGGGATC
 clone5  GGCCCCAGAG AATGACCTCA GGTGATCCCT GCCCAGCCCA TGGGGGGATC 1651                                                     1700
clone11  ACGCCACCTT CCCCCCACCC AGAGGGAGCC CTGCCC...T ACCCCAGTGA
 clone3  CTGCCACCTT CCCCCCACCC AGAGGGAGCC CTGCCCCGAG GCCCTGATGA
 clone5  CTGCCACCTT CCCCCCACCC AGAGGGAGCC CTGCCCCGAG GCCCTGATGA 1701                                                     1750
clone11  CCCTGCCCAG CCCTCCGTGG GCAGACACAG CACTGACCAC CCCTCCCTGT
 clone3  TGCCACCCAG CCCCCGTGG GCAGACACAG CACTGACCAC CCCTCCCTGT
 clone5  TGCCACCCAG CCCCCCGTGG GCAGACACAG CACTGACCAC CCCTCCCTGT 1751                                                     1800
clone11  GCAGACTTGC TGCTGGAGGA GGAGATCTGT GCGGACGACC TGGATGGGGA
 clone3  GCAGACCTGC TGCTGGAGGA GGAGATCTGT GCGGACGCCC AGGACGGGGA
 clone5  GCAGACCTGC TGCTGGAGGA GGAGATCTGT GCGGACGCCC AGGACGGGGA 1801                                                     1850
clone11  GCTGGACGGG CTCTGGACCA CCATCTCCAT CTT
 clone3  GCTGGACGGG CTCTGGACGA CCATCACCAT CTT
 clone5  GCTGGACGGG CTCTGGACCA CCATCACCAT CTT
```

Figure 1(d)

Figure 2(a)-(e). Novel nucleotide sequnces 3'prime of the sheep Cgamma
genes. Primers are shown in shaded boxes. The 5' primer is in CH3, and the
3' primer is in M2. The sequences of clone 11 and clone 1 are set forth in
SEQ ID NO: 8 and SEQ ID NO: 9, respectively.

```
            101                                                      150
clone11     CCTACCCTG TGTGCTGATG CACGAGGCTC TACACAACCA CTACACACAG
clone1      CCTACGCTG TGTGCTGATG CACGAGGCTC TGCACAACCA CTACACACAG 151                                                      200
clone11     AAGTCGATCT CTAAGCCTCC GGGTAAATGA GCCACATGCC CCCGCACCAG
clone1      AAGTCGGTCT CTAAGCCTCC GGGTAAATGA GCCACACGCC CCCGCACCAG 201                                                      250
clone11     CAAGCCCTCA CCCAGCCCGC CCTCCCCGGG CTCCAGGTCC AGCCAGGACG
clone1      CAAGCCCTCA CCCAGCCCGC CCTCCCCGGG CTCCAGGTCC AGCCAGGACG 251                                                      300
clone11     CCCTAGCCCC TCCCTGTGTG CATGCCTCCT GGGCCGCCAT GAATAAAGCA
clone1      CCCTAGCCCC TCCCTGTGTG CATGCCTCCT GGGCCGCCAT GAATAAAGCA 301                                                      350
clone11     CCCAGGCCGC CCTGGGACCC TGCAACGCTG TGCTTGTTCT TTCCGAGGCA
clone1      CCCAGGCCGC CCTGGGACCC TGCAGCGCTG TGCTGGTTCT TTCCGAGGCA 351                                                      400
clone11     GAGCCCTGGT GACCGCCAGG CCTGCGGGGG GTGGGCTGAG CCCACTCTGG
clone1      GAGCCCTGGT GATCGCCAGG CCTGCGGGGG GCGGGCTGAG CCCACTCTGG 401                                                      450
clone11     GCCGCTTGGT TCAGCATCTG TGGGGGCGCT GACCCCTCTC CGGGCCAGAC
clone1      GCCGCTTGGT TCAGCATCTG TGGGGGCGCT GACCCCTCTC CGGGCCAGAC 451                                                      500
clone11     ACACAGTGAG TGGGTCCGGC AGGGCACCTG GGGGCTGCCC GAGGCCTCGG
clone1      ACACAGTGAG TGGGTCCGGC AGGGCACCTG GGGGCTGCCC GAGGCCTCGG 501                                                      550
clone11     AGGGGCTTGG CCAGAGGCGC AGCTTCACGG CCCCCTCCAG CCACCACATT
clone1      AGGGGCTTGG CCAGAGGCGC AGCTCCACGG CCCCCTCCAG CCACCACATT 551                                                      600
clone11     CTGGGCCAGA CTCTGGGCAG GAACGGGGGA AGCCCCCGAC ACCTCAGGGA
clone1      CTGGGCCAGA CTCTGGGCAG GAACGGGGGA AGCCCCCGAC ACCTCAGGGA 601                                                      650
clone11     TTGAGGCCCA ACGCTTCCCG CCTCTGCTCC AGCCCACGCT GAGGGGCAGG
clone1      TTGAGGCCCA ACGCTTCCCG CCTCTGCTCC AGCCCACGCT GAGGGGCAGG
```

Figure 2(a)

```
            651                                                       700
clone11  GCCGCGGCCT TGTCCCCAGG CCCCTGTTCC TGGGTGCCCA GAGTCCGTGT
 clone1  GCCGCGGCCT TGTCCCCAGG CCCCTGTTCC TGGGTGCCCA GAGTCCGTGT 701                                                       750
clone11  GTCCACTCTG GGCCTGCCTG GAGCCAGACT GGCCCAGGGG GAGGCCCTGC
 clone1  GTCCACTCTG GGCCTGCCTG GAGCCAGACT GGCCCAGGGG GAGGCCCTGC 751                                                       800
clone11  TTCACCCTCA GGCTCCCGAG GTCAGGCATC ATCCTCGTCG GCCAGTAGCT
 clone1  TTCACCCTCA GGCTCCCGAG GTCAGGCATC ATCCTCGTCG GCCAGTAGCT 801                                                       850
clone11  CTGCCTGGCT CTCTCTGCCC GGGGCCAAGC CTGTGTGCCC ATGGGGAGGT
 clone1  CTGCCTGGCT CTCTCTGCCC GGGGCCAAGC CTGTGTGCCC ATGGGGAGGT 851                                                       900
clone11  CGTCCCTGTG CCTGAAAAGG GCCCAGGCTG GGAGCCCTGA ACGTCCAGGG
 clone1  CGTCCCTGTG CCTGAAAAGG GCCCAGGCTG GGAGCCCTGA ACGTCCAGGG 901                                                       950
clone11  CAGGGACCTA GCTGCTCCCT GGGGACACTG AGCCCAGAGC CCCAGACACC
 clone1  CAGGGACCTA GCTGCTCCCT GGGGACACTG AGCCCAGAGC CCCAGACACC 951                                                      1000
clone11  AAGCCCCAGC CCCGCACGCA CACGAGACAG CCCACACCCA GCGTCCTCCA
 clone1  AAGCCCCAGC CCCGCACGCA CACGAGACAG CCCACACCCA GCGTCCTCCA 1001                                                      1050
clone11  CACGCACTCA GGCGTCCACC CGCACACAAG CATGCTTCAC CCCCGTCACA
 clone1  CACCCACTCA GGCGTCCACC CGCACACAAG CATGCTTCAC CCCCGTCACA 1051                                                      1100
clone11  CACCCACATG CCTGCACACA CTCAGGTCTC ACGCTCCGGG ACCCATGGAG
 clone1  CACCCACATG CCTGCACACA CTCAGGTCTC ACGCTCCGGG ACCCATGGAG 1101                                                      1150
clone11  TGATCCCACG GGCCCAGACC CAGAGCTGGG TCTCATGAGC CCTCCCTGTG
 clone1  TGATCCCACG GGCCCAGACC CAGAGCTGGG TCTCATGAGC CCTCCCTGTG 1151                                                      1200
clone11  GACACCAGCT GGTCCCCATT CTCCAGCGCC CTTGGGCTGC TCAGTGGCCC
 clone1  GACACCAGCT GGTCCCCATC CTCCAGCGCC CTTGGGCTGC TCAGTGGCCC 1201                                                      1250
clone11  TTTCCCACAC TGACCACACT GACCAGGTCA GACATCCTTC CTCGCCTCCC
 clone1  TTTCCCACAC TGACCACACT GACCAGGTCA GACATCCTTC CTCGCCTCCC
```

Figure 2(b)

```
           1251                                                    1300
clone11    CTGGGGCACC CACGCCCCTC CCTCGCAGGC TGAGACCCCC CCTCAGCCCC
clone1     CTGGGGCACC CACGCCCCTC CCTTGCAGGC TGAGACCCCC CCTCAGCCCC 1301                                                    1350
clone11    TCGTCCTGGC ACCCTCACCC CTCGGGCACA GGGACACAGC CCGGCACTGT
clone1     TCGTCCTGGC ACCCTCACCC CTCGGGCACA GGGACACAGC CCGGCACTGT 1351                                                    1400
clone11    CTGCCCTCCC TCTCGGGGAC AGAGCCCAGG CACGTGTGCT CTGCTGAGCC
clone1     CTGCCCTCCC TCTCGGGGAC AGAGCCCAGG CACGTGTGCT CTGCTGAGCC 1401                                                    1450
clone11    TCCCGGCTCC AGGCCTGGCC CCCAGGGCAG AGGAGGCCAG GAATTGAGCC
clone1     TCCCGGCTCC AGGCCTGGCC CCCAGGGCAG AGGAGGCCAG GAATTGAGCC 1451                                                    1500
clone11    TCTGTCCTGC GGGGAGGTGG GGTCAGGGCC CCAGCTCAGG GCACAGCTCA
clone1     TCTGTCCTGC GGGGAGGTGG GGTCAGGGCC CCAGCTCAGG GCACAGCTCA 1501                                                    1550
clone11    GGATGGGAGC AGGACCCCAC AGGCCAGGCC CAGACAGTGG CCAGGGCTGG
clone1     GGATGGGAGC AGGACCCCAC AGGCCAGGCC CAGACAGTGG CCAGGGCTGG 1551                                                    1600
clone11    GGCTGGGGCT GGGGCCCAGA GACTGACCTC AGGTGACCCC TGCCCGGCCC
clone1     GGCTGGGGCT GGGGCCCAGA GACTGACCTC AGGTGACCCC TGCCCGGCCC 1601                                                    1650
clone11    ATGGGGATC ACACCGCCAT CCCCCCCGCC GCAGAGGGAG CCCTGCCCCG
clone1     ATGGGGATC ACACCGCCAT CCCCCCCGCC GCAGAGGGAG CCCTGCCCCG 1651                                                    1700
clone11    AAGCCCCGAT GGCCCCGCCC AGCCCCCCGT GGGCAGACAC AGCACTGACC
clone1     AAGCCCCGAT GGCCCCGCCC AGCCCCCCGT GGGCAGACAC AGCACTGACC 1701                                                    1750
clone11    CCCCTCCCTG TGCAGATCTG CTGCTGGAGG AGGAGAGCTG TGCGGACGCC
clone1     CCCCTCCCTG TGCAGATCTG CTGCTGGAGG AGGAGAGCTG TGCGGACGCC 1751                                                    1800
clone11    CAGGACGGGG AGCTGGACGG GCTCTGGACG ACTATCTCCA TCTTCATCAC
clone1     CAGGACGGGG AGCTGGACGG GCTCTGGACG ACTATCTCCA TCTTCATCAC 1801                                                    1850
clone11    GCCCTTCCTG CTCAGCGTCT GCTACAGCGC CACCGTGACC CTCTTCAAGG
clone1     GCTCTTCCTG CTCAGCGTCT GCTACAGTGC CACCGTGACC CTCTTCAAGG
```

Figure 2(c)

```
               1851                                                   1900
clone11   TGGGGGTCCA CCCTGCTGGG CCCTCGGGCC CCCTCTCTGT CCCCAGGGTC
clone1    TGGGGGCCCA CCCTGCTGGG CCCTCGGGCC CCCTCTCTGT CCCCAGGGTC 1901                                                   1950
clone11   CCCGCAGAGT CCCTCCCTGC CCCTCACTGT CCCTCCCTGT CCCTCTCTGT
clone1    CCCGCAGAGT CCCTCCCTGC CCCTCACTGT CCCTCCCTGT CCCTCTCTGT 1951                                                   2000
clone11   CCCTCTCTGT CCCTCTCTGT CCCTCTCTGT CCGTTCATTT TCCCTTCACC
clone1    CCCTCTCTGT CCCTCTCTGT CCCTCTCTGT CCGCTCATTT TCCCTTCACC 2001                                                   2050
clone11   GTAAGCTTGA GACAGATTGG GGTCATTTCA GAGGGCGTCT GAAGAGTCTC
clone1    GTAAGCTTGA GACAGATTGG GGTCATTTCA GAGGGCGTCT GAAGAGTCTC 2051                                                   2100
clone11   TGTGCCGCAC GCCTCCCTTC ATGTCAGTGG GGAGAATTCA GCAAGGGTGG
clone1    TGTGCCGCAC GCCTCCCTTC ATGTCAGTGG GGAGAATTCA GCAAGGGTGG 2101                                                   2150
clone11   AGTGCTGGGT GAGAAATGAG GCTTGCGGCG CTCACGAGCA GTGATGGGGC
clone1    AGTGCTGGGT GAGAAATGAG GCTTGCGGCG CTCACGAGCA GTGATGGGGC 2151                                                   2200
clone11   ACTGCTGCTC CCTGAGACCT GCGCGGACAC CGTTTTCCAT CGCAGGAGAA
clone1    ACTGCTGCTC CCTGAGACCT GCGCGGACAC CGTTTTCCAT CGCAGGAGAA 2201                                                   2250
clone11   GCGGGCAAGG GAAAACGCCC TCTTGGTCTC TCTTGAGTAA ATGTCGCGTT
clone1    GCGGGCAAGG GAAAACGCCC TCTTGGTCTC TCTTGAGTAA ATGTCGCGTT 2251                                                   2300
clone11   TTGGTCATCA GTCCCTCCCC CAGTGAGGCT AGAGGAGTTT ACTTCTCCCT
clone1    TTGGTCATCA GTCCCTCCCC CAGTGAGGCT AGAGGAGTTT ACTTCTCCCT 2301                                                   2350
clone11   CTCGATGGTC AGGTCAGGAC TGTCATAGAC TCCGGATCAC CTTCCTGTAA
clone1    CTCGATGGTC AGGTCAGGAC TGTCATAGAC TCCGGATCAC CTTCCTGTAA 2351                                                   2400
clone11   ATGCTTGCTT TTTGTGTGCA GAGAGCCTGT TTTAGCTCGG GGGTCCTCAG
clone1    ATGCTTGCTT TTTGTGTGC. .AGAGCCTGT TTTAGCTCGG GGGTCCTCAG 2401                                                   2450
clone11   CTCACTGAGC TCGCGGGGCA GGGGTGGGCT CGGGCTGGCG CCGCCTGTTC
clone1    CTCACTGAGC TCGCGGGGCA GGGGTGGGCT CGGGCTGGCG CCGCCTGTTC
```

Figure 2(d)

```
             2451                                                    2500
clone11  GGGAGCGCAT CTCCAGCATG CTGTCGCACA GCTTCGTTGC TAACAAGACC
 clone1  GGGAGCGGCA TCTCCAGCTG CTGTCGCACA GCTTCGTTGC TAACAAGACC 2501                                                    2550
clone11  GCTTAGTCTC GTGGTTAGAC CAACCTGCTT TCTCGAGTAA TTGTTAATTT
 clone1  GCTTAGTCTC GTGGTTAGAC CAACCTGCTT TCTCGAGTAA TTGTTAATTT 2551                                                    2600
clone11  ACAGGAGTTT CCTGTATTTT TCAACTTATA ATCCCCTAGT CAGATAACTC
 clone1  ACAGGAGTTT CCTGTATTTT TCAACTTATA ATCCCCTAGT CAGATAACTC 2601                                                    2650
clone11  TTTAATCACC TATTCTGCCC CTTCATTTTC TCCCTATCGA TCTCAGCAAC
 clone1  TTTAATCACC TATTCTGCCC CTTCATTTTC TCCCTATCGA TCTCAGCAAC 2651                                                    2700
clone11  CCATCACTGC CCTCACTGTC CTTAAACTGT CCCTTAACTG ACCAGACTGT
 clone1  CCATCACTGC CCTCACTGTC CTTAAACTGT CCCTTAACTG ACCAGACTGT 2701                                                    2750
clone11  CCCTCAGTGT CCCCTCAGAG TCACCTCCCT ATCACCTCAC TGTCCCTCTC
 clone1  CCCTCAGTGT CCCCTCAGAG TCACCTCCCT ATCACCTCAC TGTCCCTCTC 2751                                                    2800
clone11  TGCCCCTCTC TGCCCCTCTC TGTCCCTCCC TGCCCCTCCC CGTCCCCTCT
 clone1  TGCCCCTCTC TGCCCCTCTC TGTCCCTCTC TGTCCCTCCC CGTCCCCTCT 2801                                                    2850
clone11  CTGTCCCTCT CTGCCCCTCA CTGCTCCTCT CTGCACCTCA CTGCTCCTCA
 clone1  CTGTCCCTCT CTGCCCCTCA CTGCTCCTCT CTGCACCTCA CTGCTCCTCA 2851                                                    2900
clone11  CTGCCCTGGG GGAGGCCCGC ATCGAGGTGT CTCTGCTCAC CCCGTCCCCC
 clone1  CTGCCCTGGG GGAGGCCCGC ATCGAGGTGT CTCTGCTCAC CCCGTCCCCC 2901                                                    2950
clone11  ACCCCGTACC CCCCGCCAGG TGAAGTGGAT CTTGTCCTCG GT
 clone1  ACCCCGTCCC CCCCGCCAGG TGAAGTGGAT CTTCTCCTCG GT
```

Figure 2(e)

Figure 3(a)-(b). Novel 3'prime flanking sequence (SEQ ID NO: 10) of rabbit Cgamma gene.

```
                                          GTCCGCCGACGCCGCAGG
TGTGCACCCCGCACACAAATAAAGCACCCAGCTCTGCCCTGAGAGGCTGTCCTGATTCCT
TCCAAGGCAGAGGCTTCCACTCGGGCCGGACAGGGTTGGGCGGGCGCCGTGGGCTCTGCT
GTGGCCAGCAGCCAGAACGGTCAACAGTGGGACAGGGGCAGACCCACAGCACAGGGGCCT
GCCAAGAACTGGGCTCAGCCGGAGTGCTGTGGCAGGTCCCCCCTTGCAGCTAGCACGTGT
GTGCTGGGCAGGCAGAGGCCCCAGGGGAGGAGCACACAGCTACCACCTCTGCAAGAGCC
TGGCCTGGCGCCCAGGTCCCAGTCCACAGGGTGTGTAGTACACAGAGCCTCATCTTACCA
CAGATGTAGGGACAGACCCACCACGCCCCTGCACCCCACCCAGCCTCGCCCCTTGTGGGA
CCAGGGCTACCACTCCACTCCCCCGCCCAGAGCAGCAGAAGCAGGTGGCATCCTCAGCAG
AGGGACAGTCTCACCCCTCCACGGCACTGAGCCCTGACCCATCAAACAAGCCCCTCCTGC
TGCACAGCACCTGTGTGCACATCACACACACACACACACACACACTGAGGCCTGACCCCA
TCAAACAAGCCCCTCCTGCTGCACAGCACCTGTGTGCACATCACACACACACACACACAC
ACACTGAGGCCTGACCCCATCCTGCCCTCCTGCTGCATGGCACCTGTGTGCACATCACAC
ACACATGCACACACACACTCACACACACTGAGCCCTGACCCCATCCTGCCCTCCTGCTGC
ATGGCACCTGTGTGCACATCACACACACACACACACACACACACACTGAGCCCTGACC
CCATCCTGCCCTCCTGCTGCATGGCACCTGTGCACACATCACAAACACGCCTGCCTCATA
CACTGGCACTCAGAAGGGGCCCCTGTACACGCATACACATGCACACACCTTGACACATGG
GCCCCCTACACACGCATCACACACACTCATGCACACTCCTCACACATGGCCCTCCTGCAC
ATACATTGCACACACATGTGCACAGACCTCACAATGGGCCCCTGCACACACATTGTACAC
ACGCATGTGCACACACTTCACACATGGGCCCCCTGCACATGCATTGCACACACAGACACA
CACATGTGCATTCCTCACACATTGGGGCCTTGCAAGGGATGCCCTGCACACACATTGCAC
ATGCTCACATGTGCACACACCCCACACTGGAGCCTTGCATAGGGCCCCCTGTACACACAC
CATGCATACACACACACCTCACACAAGGGGCCCCTACATACGCAAAACACACACACACA
CATGCACACACCTCATACACGGGCCCCCTACACACATCACACACACACACACACACACGT
ATGCATGCCTCACACACAGACCTTGCAAGGGGCCCCCTGCACATGCATCAAACACATATG
CACATGTTTCACACACACGGTCCCCTACACACACTGCACACGCACACATGTGTACATGCT
TCACACACTGGGGCCTTGCATGGGGTCCCCTGCATAGCATAGCACCCAGAGCCACGCCAG
GTGCCTGGGCACATGGACACTGGTGCACACACAGCACCCAAGCCCAGCTCTCCCATCCAA
GGGGCACCAGCACCCCCCACTCACGAGCACCCTGAATTCCTGCTCCCCACAAGCGAACGT
GCACCCTACCTCTCCAGACGTCCCTTTCCTGTGGCCACTCCCATAGGTATTGGCGAGACC
CTCCCTTGACCCTTGGGCCTGGTCACCCAGGGGACAGGAGAGGGCCAAGTTGGGCCACAG
TACCACTGCCCAGCAGGGGTGAGGCAAGCAGAGGGTGGGTCTGTGAGGCGTCTGGCCAGC
CGTGCTGGGGCCCAGGTGGGGAGCAGCTGGGTGGCTGAGGTGGCTTCCTTGCAGGTGGTT
GGGGGGAGCTGGCCCCACAAGTGCCACTGCCCAGCACTGTCCAGTGCTTCCCCCTGAACC
TCCCGGCCACCCATCCCCAGCTGCAGCCGCAGAGGGAGTGCCCCTCGGCCTCCTCGGCAA
GACGCACGCTGACTGCCCCTCCCCATCCAGAGCTGCAGCTGGACGAGAGCTGTGCCGAGG
CCCAGGACGGGGAGCTGGACGGGCTGTGGACCACCATCACCATCTTCATCTCCCTCTTCC
TGCTCAGCGTGTGCTACAGCGCCACAGTCACCCTCTTCAAGGTGGGTGCTGCACCCGGCA
CGGGTGGGCTGGGGCCAGGGCGGGGGCCGGGGGCCAGGCCCTCCTCACCCCGCGCCGC
CGCTGCTGCAGGTGAAGTGGATCTTCTCGTCCGTGGTGGAGCTGAAACACACCATCGCTC
CCGACTACAGGAACATGATCGGGCAGGGGGCCTAGGCCCTTCGTTCTCACAGCCTGCCTC
CCTGGCCAGCAGGAGCCCCGCCTCCGCCTCGGACCCCATGGCTCTCTGCTCTGGCCGCT
CCGGACCCCTCCGCCTCGGGAGAAGCGCGCAGCTGATGCCTGCCGGCCCCTCCACGCAGC
AGTGCGGACAGCACGCATCTGTCGTCCACCCGGCAGGACCCCACCCAGGGCCAGCCCTGA
CCGCCAGCCTCCTGGACTCAGGGCTCCTCTGAGAAAAGGCCCACTTGTTGGTCCCCTCAG
CCCACACCCAGGCAGCCTCCGGTGGGTGCTTCCCTGGACCCCAGCCTGAGGCCTATGCTT
GTTCTCCTGTGGCTCTTACTCAGAGGCCCGTGCTGGACTCCCACCCACAGGGACAGTGCC
```

Figure 3(a)

CTGCTCCAACCCTCACTGCACTGGGGGTCATGGGGCCACCTTCTGTGCAGGGGTCCTGGC
TCCAAGGAGAACACTCGAAGGGCCTGCTTGGCCACCTGGCACCACGGGAGCCCCGCTGGG
TAGCTTGGCAGGGACCCCTGAGTAGAGGTGGGTGCACCCAGCCAGAAAGCCTGCTGGATG
GACAGGAGCCTGGCGTCCGGGCCCCAGGCAGGCAGACACGGCTTCATGGACAGGAGAGGC
CAAGGAACATCAGCAAAGAGAGACAGCTGGGCCGGGCGTTCCAGCCAGACCCATCCTGCA
GCCCAGCATCGGCCCCGTGTACTACAGCAGGGACAGCCAGT

Figure 3(b)

Figure 4. Novel nucleotide sequence (SEQ ID NO:11) 3'prime of the rabbit Ckappa 1 gene.

```
                              GCGAGACGCCTGCCAGGGCACCGCCAGTGACCCTGAG
GCCCAGCCTCGCCGCTCCCTCCCCTCAGTGGACCCATTCCCACCACAGTCCTCCAGCCCC
TCCCCTCCCGGCCCTCACCCCCTCCTTGGCTTTAACCTTGCGAATGTTGGTGAGATGGAT
GAATAAAGTGAATCTTTGCACTTGTGACTTCTCTCTGCTTCTTCATTTAATGGTTATTAC
TCATGGTTTCCCAGTTGCCCTAAAGTCACCGCCATTTCATCCTCCATCCCACCCTGCCCT
GCTGTCCTCCGGGAGACACCACTCCCTGAAACCCACAGGCCCCTGTCTTCACACCGCCGA
CCCCGACCACACGTGAGGGGCTTGCTTCGTGTCTCACTCCCCTCATCGAGCCCCAGAGTC
CTCCTTTAGTGTTCTTACAGTCACATACAGTTATACAGTTTGAGTCAATCCAACCTGCCC
TGCCAATTTCCCAAAACAAAGATTTTCAGAATAAAACAGCTATGAAGAAAGTCATTTATG
GAAGCATGATATACAACAACAAAACAATGCAAACAACCTAACTGAATAAGCAGAGGGAAA
TGTTCAGACACACTATGGGGCTTGGGCTTCATGGAGTATTACACCTTCATTACATTTTTA
AACTTGTATTAAGGAGCTCCTATATTACAAGGATTATACTAGAGCACTTTCCATGACCTA
ATTAATTCTCATTACACTGTGAGGTTAAAAGCATTAGTTAAAATATTGGGCAGGCTCCCT
ATAGCCAACAGTTGTTCATATTCCATAACCCAACCATCATTTAGGTGACTCAGGGTCCTT
GTCCACCAAGAACTTTGGCAAGAATGTTCAGAGCAACTTCCTTTATAAAGTCAAAAATT
GGAAGTAACTCAAATGTCTACCAACAGTAGAATGGGCTGTTAATTGGCATATGTTTACAT
ATTAGAATGCTGTTTAATAAAGAGAATTAACAAACTACAACTATCCCTAATAACATAGGT
GACTCATAAACATGATGTTAAGCACAAGAACCCAAACACAAAAGACACACTGTGTATGTT
TTCATCCATAGGAAGTTCAAAACTAGTTAAAAATTGAATTAGAAATTGAGATGAAGTTTA
CTCTTGGCTGGGGGTGTGGAGTGAGGCGGTGCCTGGTGGGGACAGAAAGTGGCTGCTGG
GGTCTTGGTGATGTTCTAGTCCTCACTGTGGTGTGTGCTACTCTGAAAATGTATTGAGTA
CACAATTAGGTTTTGTGCTTTCATTATACTCCAAAGTAAGTTCTCATAAACATTGCCTTA
CACGGGGTCTACAGATAAGAGAGACTAAGAGGAATGAGTAACAGATCAAGCCACACAGC
TGGTAGGCATGGGCCTGGGATCAAACCCTGTCTGCCCAATTCTGCTCTCTTGAGCCCTAC
ACTATTCTTTCCAGCACTGGAATGCCATGCAGAACAGGGAGTAGGACATGCTACCTCCCT
AGGGTCTCCTCCTTTACCCACCTAACCAGGAGCACCCATACATAGAAACAGGATGGAAAA
GACCATCAGCAATGGAACAAGGGAGAGATTAACCTTGTTCAGTATTGTGATCCCATGTAG
GAAAGATTGTGGGAGGAGGGCTGCACACAGAGCACCGTCCCCCTTCTATGTGCCCACCGC
TCTGTGCCCCCTTATCTGCTCACCCGCCCAGCGTGCATTCACTCAGCACCCTTTTCGCCT
GCCCTCTGAAAGAGGTGCAGAAGTAACTAAACCAGCTTCCCTCCTTCAGTGACTTGGAAT
CCAGTTTTCCTCCTCTATTTCCCCCTCCTTTTCAGTGCAGGAGCCTGGAGAAATGTGATT
TGTGTTATTATAAATTTCCCACATCATTTTGTGTAAGGGAAAATATACTCAACAGTCATA
ACTGGTAAAACTGCTGTGAAAACTAAGAGAAGTAATTCATGCGAAGGTTGAGCACCAGCC
TTGTATATACTAAGAGATCCAGAAGTGTTAGTCACCGTTAGAAATAAGAAGGAGTAGCTC
AATTTGACTAGTTCCTGGTTCACTCCTTGAACATGTTCTTCAGTTATCATCTTTCAGTCC
CAAATGATTGAACTTGGAATTAACTCACATGGATTCTAGACCTGTGCCGAGAATGGCTGC
CACTCGTGCTCTAGAGCTCTGGGGATGAGGCTGTCCCTACTGTGGTGTGCTACAGGTCTA
ACAACACACCAGGTTTTGAAGACTTAGCACTATGAATATATATATATATTATATTCCAAT
AAATTTAACATACTTTCTACTTTCATTGCATGTTGAGATAGTAATCTACTTTGGATATAT
TTGGTTAAACCAAACTATTCTCAAGACAAATTTCATAGGTTTATGGTTTTTTTACAATTT
AATCAAAATATAAACATAGTCCAAACAATTAATCCATTTAAAGTGGAGAATGGCCCAAGT
GTTTGGGCCCCTGCTACCCATTTTTAAGACCAGATGTTGCTCTTGGCTTCTGGCTTTTGC
TTGGCTCAGCCCTGGCCATTGCAGCCATCTGAGGAGTAAACAGTGGATGGAAGACATCTC
CCCCCACCCTGCCCATAAAGCTCGGCATCC
```

Figure 5. Novel nucleotide sequences (SEQ ID NO:12 and SEQ ID NO: 13) 5'prime of the rabbit Cgamma gene. The sequences between SEQ ID NO: 12 and SEQ ID NO: 13 (a gap of about 1000 nt) remain to be determined.

```
CTTCAGCGTCAACGACGCCCTCCCGCTGAGTCTCACGCACCCCCG
GTGCAGGCAGTCCGGCCTCACCTGGAAGGTGCACTGACTGAAGACACTGCAAGGGGTGAG
AGCATTTCTCAGGAAAGAGCCCTGAGTTTAGAAGGCCAGAGAGCAGAGGGCTGAGGGCTG
CCTTGCGCTGCAACCCATGGAAACACAGGCTTAGCAGATGTTCAAGCTCCGGGAGTCCAC
ACTGGGTGAGGGCAGGCGTCCAGCCTGACATGGCCCCCACAGACTCGCCCACAGGTGACG
CCAGATGAGGACGGTCAAGGATCGGGGATCCTACATGCCCAGGGGCACCAAGACAGCCA
GGAGAGCACCAGAGGCCACAAGAGAGGCCTGGGACAGTCTCCCTGCTGACATCCAGAGCC
CAGGCCCCACTTGGCAGAGCTGGCTGAGAACACGTCTCTGCGGTGGAAGCTGCCCCGTCC
TGGGTGTTGCTCGGCGGGCTAAGCCGACTGACGCGGGGCGGGCCAGGCCATCGGCCCCAC
GGCCTGCAGCTTCCTCCCCAGCCCAGGCCACGTGGGCTCCTGGCTGAACTGGCCGCTCGC
TGAGCTCTCACCCCCCACCCAGCAGCAGGCCGGGCGGTGCTGCCATGAGCTCCATTCCC
ACCACACAAGCGACAGCCCGGGCAGCGCCCCAGGCCCACGGGGCGTTTGCTGTGCGGCTC
GCACTCGCTGCTCAGGGCCAGCGCAGGGTGCAGCAGGGACTCACCAACCCGCCCCGACTC
GGCTGGCACGTTTACTGGAGGCCTCTGAGCCTGACCGTGGCAGTGGGGCCCGAGCAGGCT
CCAGGCTGCCCCCTGCACCCTGGGCTTGCCGCTCCGGGACCCCTGGTGGGCACCTTCCCA
GATGTGCTCCCACCGTGCCTCCTTGGGGCTCTGGGCTCATAGCGGTCACTCTCCGCCTTC
TCTCCTCCCAGCCCTTTCCTGCCTCCCTATGGCCCCATCTAGCTCTGCCCTNTCTAGAGC
CTCTACCTGGAAGGAATCTGCTGTTGGACCAAGACACCACCCGCAGCACAGGTGGGCGCC
TTGCACTGTGCTAGGCCCTCCCCGCACAGAAAAGGGCCCTAGGCTCTGGAGGCTGCTGCT
GNCTCTGGGGCTGGCATCGGGCGCACCCTGCACCCTGCACCCTGAGGAAACTCAGGCCTG
CCCGCTCCAGGCCTGTCCCT

Gap of about 1000 nt

GAAGCTTTACTTGTTGGGGGCGG
GCAGGTCTAAGGGACCTGCCAGGTGTGGGGGCTGGGCTTGACTCAGCAGGAGCCTTCTAG
AAGGAAAGCTCTGGAGAAGGTGGGGGCAGAGGGCGGGAAAGGCCTGTGAGGAGGCGGGTG
GTGGGCAGGGCCACTGGGAAGGGACGGCTGGGGGTGACACTCAGGTTGGCACTGGGGAGG
ACCTGAGGAGGCAGGTGCCAGGCACAGAGCTGAACCTGGGCAGGGCAGGGGCAGGTAACA
AGAAGGATTCTCCTTGGAGCCTGGTCCAGGGTGGTCCAGGGCGGTCCAGGGCCTGGGGTT
TGCAAGCTGGGCTGTGACAGGGCCTCTCTCCCCAGGGGCAAGCAGCAAAGCCTGGGCACA
GAGCCCAAAGCCCCCACACAGAGAAGCTCCCCAGGGCAGGGCCTGCAGGGCTTGGGGGAC
CTTCTTGGAGCAGGCAGAGGACAGAGGCATGAGATCAGCCTCCCAGAGGCTGGAATGATA
GGTCCAGCAGGAGGGGCCCACATGGGCTCTGGTTAGCAGGAGAAAACAGCCCCCAGGTCC
CCATGGCCACCACGCACCGACTGCTGGTGAAGCTTTGGGTGGCAGACGAGAGCCACATGG
CAGCTGCTCCTGTCACTGTCTGGGACGGCATCGAGGGCGCGTGGAC
```

Figure 6. Comparison of human, mouse, rabbit, sheep, cow and camel sequences for the the M1 and M2 regions 3' of the Cgamma gene.

M1
```
                    1                                                    46  SEQ
         camel  EPLLEEESCA EAQSGELDGL WTTISIFITL FLLSVCYSAT VTLFK.        14
     human-Ig3  .ELQLEESCA EAQDGELDGL WTTITIFITL FLLSVCYSAT VTFFK.        15
   human-Ig3/2  .ELQLEESCA EAQDGELDGL WTTITILITL FLLSVCYSAT VTFFK.        16
     human-Ig1  .ELQLEESCA EAQDGELDGL WTTITIFITL FLLSVCYSAT VTFFK.        17
     mouse-Ig1  .GLQLDETCA EAQDGELDGL WTTITIFISL FLLSVCYSAA VTLFK.        18
    mouse-Ig2a  .GLDLDDVCA EAQDGELDGL WTTITIFISL FLLSVCYSAS VTLFK.        19
    mouse-mRNA  PGLQLDETCA EAQDGELDGL WTTITIFISL FLLSVCYSAA VTLFK.        20
     mouse-Ig3  .ELELNETCA EAQDGELDGL WTTITIFISL FLLSVCYSAS VTLFK.        21
   mouse-Ig3/2  .ELELNGTCA EAQDGELDGL WTTITIFISL FLLSVCYSAS VTLFK.        22
  sheep-clone11 .LLLEEESCA DAQDGELDGL WTTISIFITP FLLSVCYSAT VTLFK.        23
   sheep-clone1 .LLLEEESCA DAQDGELDGL WTTISIFITL FLLSVCYSAT VTLFK.        24
    cow-clone11 .LLLEEEICA DDLDGELDGL .......... .......... ......        25
   cow-clone3/5 .LLLEEEICA DAQDGELDGL .......... .......... ......        26
        rabbit  ..LQLDESCA EAQDGELDGL WTTITIFISL FLLSVCYSAT VTLFK.        27
```

M2
```
                    1                   27                               SEQ
         camel  VKWIFSSVVE LKRTIVPDYR NMIGQGS                              28
     human-Ig3  VKWIFSSVVD LKQTIIPDYR NMIGQGA                              29
   human-Ig3/2  VKWIFSSVVD LKQTIIPDYR NMIGQGA                              30
     human-Ig1  VKWIFSSVVD LKQTIIPDYR NMIGQGA                              31
     mouse-Ig1  VKWIFSSVVE LKQTLVPEYK NMIGQAP                              32
    mouse-Ig2a  VKWIFSSVVE LKQTISPDYR NMIGQGA                              33
    mouse-mRNA  VKWIFSSVVE LKQTLVPEYK NMIGQAP                              34
     mouse-Ig3  VKWIFSSVVQ VKQTAIPDYR NMIGQGA                              35
   mouse-Ig3/2  VKWIFSSVVQ VKQTAIPDYR NMIGQGA                              36
        rabbit  VKWIFSSVVE LKHTIAPDYR NMMGQGA                              37
 sheep-clone1/11 VKWIFSSV.. ..........                                     38
```

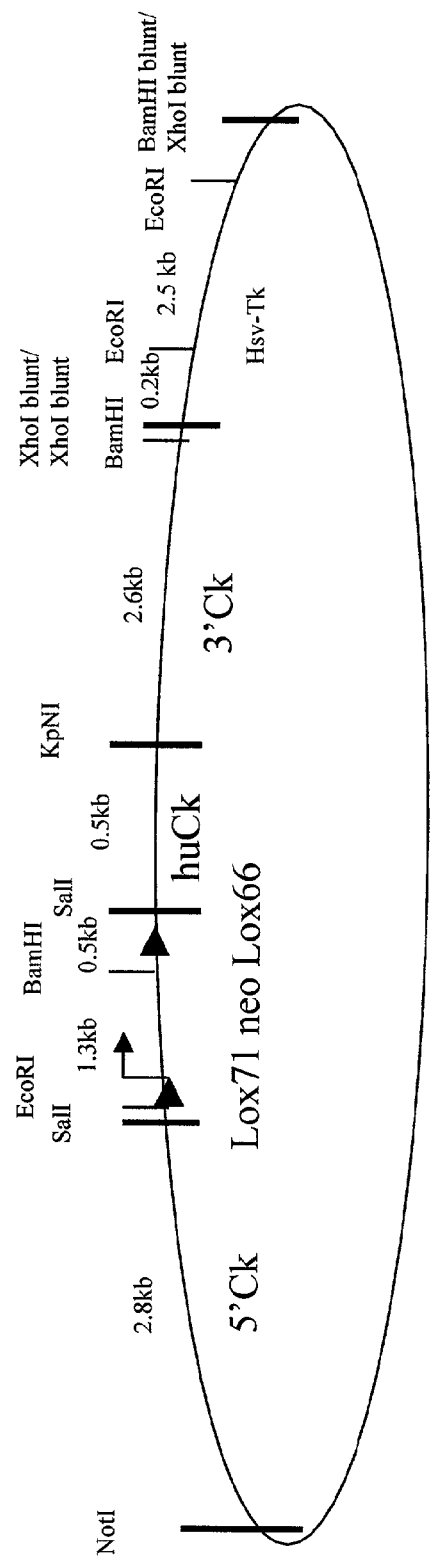
Figure 7a: DNA construct for the replacement of rabbit Cκ with human Cκ. A 0.5 kb fragment containing a DNA sequence encoding human Cκ is flanked by sequences from the rabbit Cκ1 gene. The upstream sequence (5'Cκ) is 2.8 kb, the downstream sequence (3'Cκ) is 2.6 kb. The vector also contains a lox-neo cassette for positive selection and a Hsv-Tk cassette for negative selection.

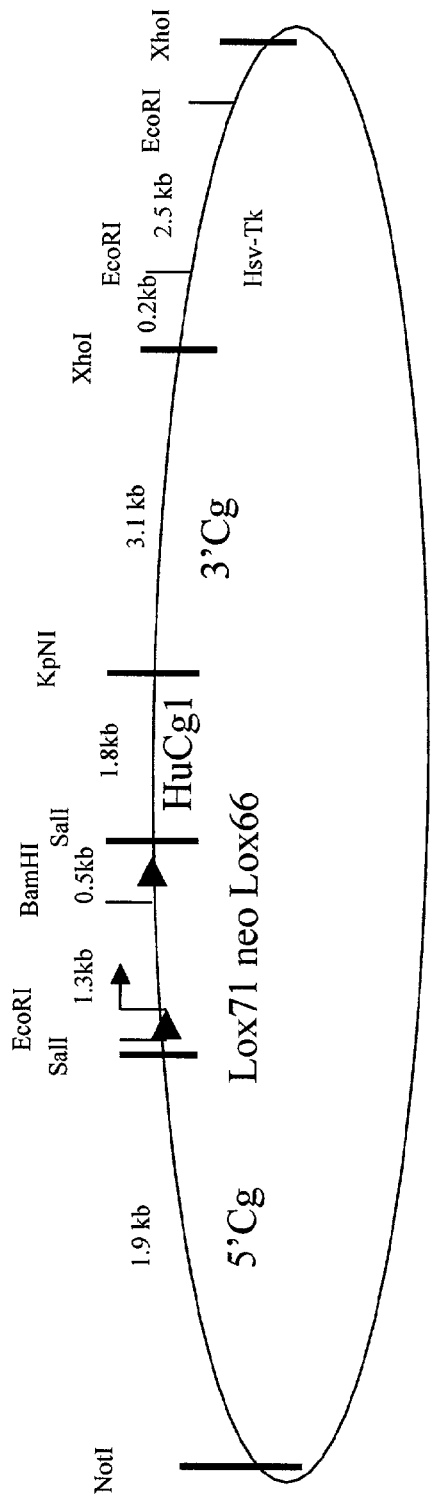

Figure 7b: DNA construct for the replacement of rabbit Cγ with human Cγ1. A 1.8 kb fragment containing a DNA sequence encoding human Cγ1 is flanked by sequences from the rabbit Cγ gene. The upstream sequence (5'Cγ) is 1.9 kb, the downstream sequence (3'Cγ) is 3.1 kb. The vector also contains a lox-neo casette for positive selection and a Hsv-Tk cassette for negative selection. The figure is not up to scale.

Figure 8. DNA fragment (SEQ ID NO: 51) containing a human immunoglobulin heavy chain Cγ1 gene segment flanked by 50 nucleotides derived from the rabbit heavy chain immunoglobulin gene. Flanking sequences derived from rabbit immunoglobulin DNA sequences are underlined.

```
                       tgacctacct accctgccaa ggtcaggggt cctccaaggc
aagggatcac atggcaccac ctctcttgca gcctccacca agggcccatc ggtcttcccc
ctggcaccct cctccaagag cacctctggg ggcacagcgg ccctgggctg cctggtcaag
gactacttcc ccgaaccggt gacggtgtcg tggaactcag gcgccctgac cagcggcgtg
cacaccttcc cggctgtcct acagtcctca ggactctact ccctcagcag cgtggtgacc
gtgccctcca gcagcttggg cacccagacc tacatctgca acgtgaatca caagcccagc
aacaccaagg tggacaagaa agttggtgag aggccagcac agggagggag ggtgtctgct
ggaagccagg ctcagcgctc ctgcctggac gcatcccggc tatgcagccc cagtccaggg
cagcaaggca ggccccgtct gcctcttcac ccggaggcct ctgcccgccc cactcatgct
cagggagagg gtcttctggc tttttcccca ggctctgggc aggcacaggc taggtgcccc
taacccaggc cctgcacaca aagggcaggt gctgggctc agacctgcca agagccatat
ccgggaggac cctgccctg acctaagccc accccaaagg ccaaactctc cactccctca
gctcggacac cttctctcct cccagattcc agtaactccc aatcttctct ctgcagagcc
caaatcttgt gacaaaactc acacatgccc accgtgccca ggtaagccag cccaggcctc
gccctccagc tcaaggcggg acaggtgccc tagagtagcc tgcatccagg gacaggcccc
agccgggtgc tgacacgtcc acctccatct cttcctcagc acctgaactc ctggggggac
cgtcagtctt cctcttcccc ccaaaaccca aggacaccct catgatctcc cggacccctg
aggtcacatg cgtggtggtg gacgtgagcc acgaagaccc tgaggtcaag ttcaactggt
acgtggacgg cgtggaggtg cataatgcca agacaaagcc gcgggaggag cagtacaaca
gcacgtaccg tgtggtcagc gtcctcaccg tcctgcacca ggactggctg aatggcaagg
agtacaagtg caaggtctcc aacaaagccc tcccagcccc catcgagaaa accatctcca
aagccaaagg tgggacccgt ggggtgcgag ggcacatgg acagaggccg gctcggccca
ccctctgccc tgagagtgac cgctgtacca acctctgtcc ctacagggca gccccgagaa
ccacaggtgt acaccctgcc cccatcccgg gatgagctga ccaagaacca ggtcagcctg
acctgcctgg tcaaaggctt ctatcccagc gacatcgccg tggagtggga gagcaatggg
cagccggaga acaactacaa gaccacgcct cccgtgctgg actccgacgg ctccttcttc
ctctacagca agctcaccgt ggacaagagc aggtggcagc aggggaacgt cttctcatgc
tccgtgatgc atgaggctct gcacaaccac tacacgcaga agagcctctc cctgtctccg
ggtaaatgag cgctgtgccg gcgagctgcc cctctccctc cccccacgc cgcagctgt.
```

Figure 9. The DNA fragment (SEQ ID NO: 52) containing a VH gene segment with more than 80% sequence identity with rabbit VH elements and encoding a human VH element polypeptide sequence. Flanking sequences derived from rabbit immunoglobulin DNA sequences are underlined.

```
           tgagtcacag tgtccsgacc atgscgtctg tgtttgcagg tgtccagtgt
gaggtgcagc tgttggagtc cgggggaggt ctcgtccagc cagggcggac cctgagactc
acctgcgcag tctctggatt caccttcagt agctatgcaa tgagctgggt ccgccaggct
ccagggaagg ggctggaatg ggtcggagcc attagtggta gsggtagcac atactacgcg
gacagcgtga aaggccgatt caccatctcc agagacaact ccaagaacac gctgtatctg
caaatgaaca gtctgagagc cgaggacacg gccgcctatt actgtgcgaa agacacagtg
agggggccctc aggctgagcc cagacacaaa cctccctgca
```

Figure 10. DNA fragment (SEQ ID NO: 53) containing a human immunoglobulin light chain Cκ gene segment flanked by 50 nucleotides derived from the rabbit light chain immunoglobulin Kappa1 gene. Flanking sequences derived from rabbit immunoglobulin DNA sequences are underlined.

```
                                      .catccacat ggcacccagg
           ggagatgtcc actggtacct aagcctcgcc atcctgtttg cttctttcct caggaactgt
ggctgcacca tctgtcttca tcttcccgcc atctgatgag cagttgaaat ctggaactgc
ctctgttgtg tgcctgctga ataacttcta tcccagagag gccaaagtac agtggaaggt
ggataacgcc ctccaatcgg gtaactccca ggagagtgtc acagagcagg acagcaagga
cagcacctac agcctcagca gcaccctgac gctgagcaaa gcagactacg agaaacacaa
agtctacgcc tgcgaagtca cccatcaggg cctgagctcg cccgtcacaa agagcttcaa
caggggagag tgttagagcg agacgcctgc cagggcaccg ccagcgaccc tgaggcccag
cctcgc.
```

Figure 11. DNA fragment (SEQ ID NO: 54) containing a Vκ gene segment with more than 80% sequence identity with rabbit Vκ elements and encoding a human Vκ element polypeptide sequence. Flanking sequences derived from rabbit immunoglobulin DNA sequences are underlined.

```
                                      ..ggcaggct gctcccaccc
catgcaggag gcagtaccag gcaggaccca gcatggacat gagggtccct gctcagctcc
tggactcct gctgctctgg ctcccaggta agcagggaaa caacaaaaat tttattcagc
cagtgtagcc actaatgcct ggcacttcag gaaattcttc ttagaacatt actaatcatg
tggatatctg ttttatgtt cctaatatca gataccagat gttacatcca gatgacccag
tctccatcct ctctgtctgc atctgtggga gacagagtca ccatcacttc ccgagccagt
cagggcatta gcaattactt agcctggtat cagcagaaac cagggaaggt tcccaagctc
ctgatttatg ctgcatccac tttgcaatct ggggtcccat cgcggttcag tggcagtgga
tctgggacag atttcactct taccatcagc agcctgcagc ctgaagatgt tgccacctat
tactgtcaaa agtacaacag tgcccctcca cttttcggcg gagggaccaa ggtggagatc
aaacgtaagt gcactttcct aatgttcctc accgtttctg cctgatttgt ttgcttttc
cattttttcgctat
```

Figure 12. DNA fragment (SEQ ID NO: 57) containing a gene encoding human
immunoglobulin light chain constant region Clambda2 flanked by 50 nucleotides
derived from the chicken light chain gene. The DNA sequence of chicken origin
is underlined.

```
catacacag ccatacatac gcgtgtggcc gctctgcctc tctcttgcag gtcagcccaa
ggctgccccc tccgtcactc tgttcccgcc ctcctctgag gagcttcaag ccaacaaggc
cacactggtg tgtctcataa gtgacttcta cccgggagcc gtgacagtgg cttggaaagc
agatagcagc cccgtcaagg cgggagtgga gaccaccaca ccctccaaac aaagcaacaa
caagtacgcg gccagcagct atctgagcct gacgcctgag cagtggaagt cccacagaag
ctacagctgc caggtcacgc atgaagggag caccgtggag aagacagtgg cccctacaga
atgttcatag tagtcccact ggggatgcaa tgtgaggaca gtggttcctc accctccctg
```

Figure 13. Modification of the chicken light chain locus using the ET system.
A chicken genomic BAC clone with the full length light chain locus was modified by homologous recombination. In a first step Cλ was deleted by insertion of a selection cassette which was in a second homologous recombination step exchanged against the human Cλ gene. The homology stretch was 50bp.

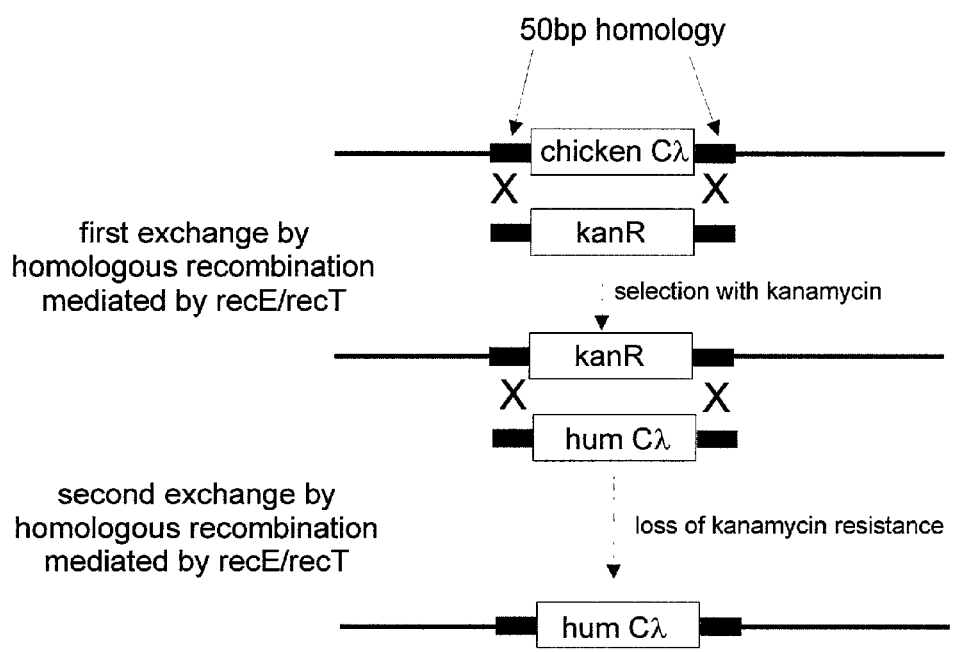

Figure 14. DNA fragment (SEQ ID NO: 58) containing a VJ gene segment with 80% sequence identity with chicken V gene segments and encoding a human VJ immunoglobulin polypeptide. Flanking sequences derived form chicken immunolgobulin DNA sequences are underlined.

```
.ttgccgttt tctcccctct ctcctctccc tctccaggtt ccctggtgca gtcagtgctg actcagccgc
cctcggtgtc agcagccccg ggacaagaag tcacgatctc ctgctccggg tctagtagca acattggcga
taatttcgtc tcttggtacC agcagctgcc tggcactgcc cctaagcttc tgatctatga taacaacAag
agaccctcgg gcatccctga ccgattctcc ggttccaaat ccggcacctc agccacatta ggcatcactg
ggctccaaac cggcgacgag gctgactatt actgtgggac ttgggacagc agcctttctg ttggtatgtt
tgggggcggg acacgcgtga ccgtcctagg tgagtcgctg acctcgtctc ggtctttctt cccccat…
```

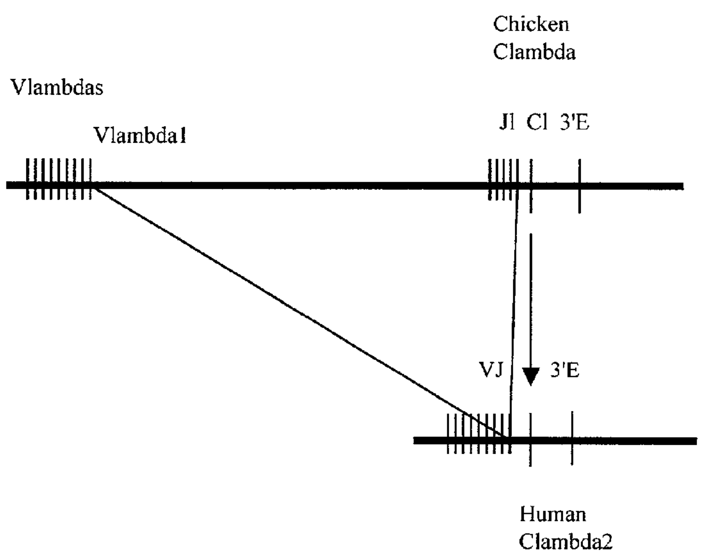

Figure 15. Humanized chicken light chain locus.

US 7,129,084 B2

PRODUCTION OF HUMANIZED ANTIBODIES IN TRANSGENIC ANIMALS

CROSS REFERENCE TO RELATED APPLICATIONS

This application claims the benefit of priority of Provisional Application Ser. No. 60/222,872, filed on Aug. 3, 2000, and Provisional Application Ser. No. 60/276,156, filed on Mar. 15, 2001.

FIELD OF THE INVENTION

This invention relates to humanized antibodies produced from transgenic non-human animals. The non-human animals are genetically engineered to contain one or more humanized immunoglobulin loci which are capable of undergoing gene rearrangement and gene conversion in the transgenic non-human animals to produce diversified humanized immunoglobulins. The present invention further relates to novel sequences, recombination vectors and transgenic vectors useful for making these transgenic animals. The humanized antibodies of the present invention have minimal immunogenicity to humans and are appropriate for use in the therapeutic treatment of human subjects.

BACKGROUND OF THE INVENTION

The therapy of infectious diseases caused by bacteria, fungi, virus and parasites is largely based on chemotherapy. However, the emergence of drug-resistant organisms requires the continuous development of new antibiotics. Therapies of patients with malignancies and cancer are also based on chemotherapy. However, many of these therapies are ineffective and the mortality of diseased patients is high. For both infectious diseases and cancer, improved and innovative therapies are needed. Therapy of steroid resistant rejection of transplanted organs requires the use of biological reagents (monoclonal or polyclonal antibody preparations) that reverse the ongoing alloimmune response in the transplant recipient. The major problem of antibody preparations obtained from animals is the intrinsic immunogenicity of non-human immunoglobulins in human patients. In order to reduce the immunogenicity of non-human antibodies, genetic engineering of individual antibody genes in animals has been proposed. In particular, it has been shown that by fusing animal variable (V) region exons with human constant (C) region exons, a chimeric antibody gene can be obtained. However, this approach may only eliminate the immunogenicity caused by the non-human Fc region, while the remaining non-human Fab sequences may still be immunogenic. In another approach, human immunoglobulin genes for both, heavy and light chain immunoglobulins have been introduced into the genome of mice. While this genetic engineering approach resulted in the expression of human immunoglobulin polypeptides in genetically engineered mice, the level of human immunoglobulin expression is low. This may be due to species-specific regulatory elements in the immunoglobulin loci that are necessary for efficient expression of immunoglobulins. As demonstrated in transfected cell lines, regulatory elements present in human immunoglobulin genes may not function properly in non-human animals.

Several regulatory elements in immunoglobulin genes have been described. Of particular importance are enhancers downstream (3') of heavy chain constant regions and intronic enhancers in light chain genes. In addition, other, yet to be identified, control elements may be present in immunoglobulin genes. Studies in mice have shown that the membrane and cytoplasmic tail of the membrane form of immunoglobulin molecules play an important role in expression levels of human-mouse chimeric antibodies in the serum of mice homozygous for the human Cγ1 gene. Therefore, for the expression of heterologous immunoglobulin genes in animals it is desirable to replace sequences that contain enhancer elements and exons encoding transmembrane (M1 exon) and cytoplasmic tail (M2 exon) with sequences that are normally found in the animal in similar positions.

The introduction of human immunoglobulin genes into the genome of mice resulted in expression of a diversified human antibody repertoire in genetically engineered mice. In both mice and humans, antibody diversity is generated by gene rearrangement. This process results in the generation of many different recombined V(D)J segments encoding a large number of antibody molecules with different antigen binding sites. However, in other animals, like rabbits, pigs, cows and birds, antibody diversity is generated by a substantially different mechanism called gene conversion. For example, it is well established that in rabbit and chicken, VDJ rearrangement is very limited (almost 90% of immunoglobulin is generated with the 3'proximal VH1 element) and antibody diversity is generated by gene conversion and hypermutation. In contrast, mouse and human gene conversion occurs very rarely, if at all. Therefore, it is expected that in animals that diversify antibodies by gene conversion a genetic engineering approach based on gene rearrangement will result in animals with low antibody titers and limited antibody diversity. Thus, the genetic engineering of large animals for the production of non-immunogenic antibody preparations for human therapy requires alternative genetic engineering strategies.

Relevant Literature

The use of polyclonal antibody preparations for the treatment of transplant rejection was recently reviewed by N. Bonnefoy-Berard et al., *J Heart Lung Transplant* 1996; 15(5):435–442; C. Colby et al., *Ann Pharmacother* 1996; 30(10):1164–1174; M. J. Dugan et al., *Ann Hematol* 1997; 75(1–2):41–46. The use of polyclonal antibody therapies for autoimmune diseases has been described by W. Cendrowski, *Boll Ist Sieroter Milan* 1997; 58(4):339–343; L. K. Kastrukoff et al., *Can J Neurol Sci* 1978; 5(2):175–178; J. E. Walker et al., *J Neurol Sci* 1976; 29(2–4):303–309. The depletion of fat cells using antibody preparations has been described by L. De Clercq et al., *J Anim Sci* 1997; 75(7): 1791–1797; J. T. Wright et al., *Obes Res* 1995; 3(3): 265–272.

Regulatory elements in immunoglobulin genes have been described by Bradley et al. (1999), *Transcriptional enhancers and the evolution of the IgH locus*; Lauster, R. et al., *Embo J* 12: 4615–23 (1993); Volgina et al., *J Immunol* 165:6400 (2000); Hole et al., *J Immunol* 146:4377 (1991).

Antibody diversification by gene conversion in chicken and rabbit has been described by Bucchini et al., *Nature* 326: 409–11 (1987); Knight et al., *Advances in Immunology* 56: 179–218 (1994); Langman et al., *Res Immunol* 144: 422–46 (1993). The generation of mice expressing human-mouse chimeric antibodies has been described by Pluschke et al., *Journal of Immunological Methods* 215: 27–37 (1998). The generation of mice expressing human-mouse chimeric antibodies with mouse derived membrane and cytoplamic tails has been described by Zou et al., *Science* 262: 1271–1274

(1993); Zou et al. *Curr Biol* 4: 1099–1103. The generation of mice expressing human immunoglobulin polypeptides has been described by Bruggemann et al. *Curr Opin Biotechnol* 8(4):455–8 (1997); Lonberg et al. *Int Rev Immunol* 13(1):65–93 (1995); Neuberger et al., *Nature* 338: 350–2 (1989). Generation of transgenic mice using a BAC clone has been described by Yang et al., *Nat Biotechnol* 15: 859–65 (1997).

The generation of transgenic rabbits has been described by Fan, J. et al., *Pathol Int* 49: 583–94 (1999); Brem et al., *Mol Reprod Dev* 44: 56–62 (1996). Nuclear transfer cloning of rabbits has been described by Stice et al., *Biology of Reproduction* 39: 657–664 (1988). Rabbits with impaired immunoglobulin expression have been described by McCartney-Francis et al., *Mol Immunol* 24: 357–64 (1987); Allegrucci, et al., *Eur J Immunol* 21: 411–7 (1991).

The production of transgenic chicken has been described by Etches et al., *Methods in Molecular Biology* 62: 433–450; Pain et al., *Cells Tissues Organs* 1999; 165(3–4): 212–9; Sang, H., "Transgenic chickens—methods and potential applications", *Trends Biotechnol* 12:415 (1994); and in WO 200075300, "Introducing a nucleic acid into an avian genome, useful for transfecting avian blastodermal cells for producing transgenic avian animals with the desired genes, by directly introducing the nucleic acid into the germinal disc of the egg".

Agammaglobulinemic chicken have been described by Frommel et al., *J Immunol* 105(1): 1–6 (1970); Benedict et al., *Adv Exp Med Biol* 1977; 88(2): 197–205.

The cloning of animals from cells has been described by T. Wakayama et al., *Nature* 1998; 394:369–374; J. B. Cibelli et al., *Science* 280:1256–1258 (1998); J. B. Cibelli et al., *Nature Biotechnology* 1998; 16:642–646; A. E. Schnieke et al., *Science* 278: 2130–2133 (1997); K. H. Campbell et al., *Nature* 380: 64–66 (1996).

Production of antibodies from transgenic animals is described in U.S. Pat. No. 5,814,318, U.S. Pat. No. 5,545,807 and U.S. Pat. No. 5,570,429. Homologous recombination for chimeric mammalian hosts is exemplified in U.S. Pat. No. 5,416,260. A method for introducing DNA into an embryo is described in U.S. Pat. No. 5,567,607. Maintenance and expansion of embryonic stem cells is described in U.S. Pat. No. 5,453,357.

The mechanisms involved in the diversification of the antibody repertoire in pigs, sheep and cows are reviewed in Butler, J. E. (1998), "Immunoglobulin diversity, B-cell and antibody repertoire development in large farm animals", *Rev Sci Tech* 17:43. Antibody diversification in sheep is described in Reynaud, C. A., C. Garcia, W. R. Hein, and J. C. Weill (1995), "Hypermutation generating the sheep immunoglobulin repertoire is an antigen-independent process", *Cell* 80:115; and Dufour, V., S. Malinge, and F. Nau. (1996), "The sheep Ig variable region repertoire consists of a single VH family", *J Immunol* 156:2163.

SUMMARY OF THE INVENTION

One embodiment of the present invention provides humanized antibodies (humanized immunoglobulins) having at least a portion of a human immunoglobulin polypeptide sequence.

The humanized antibodies of the present invention are made from transgenic non-human animals genetically engineered to contain one or more humanized Ig loci.

Preferably, the humanized antibodies of the present invention are prepared from transgenic non-human animals which generate antibody diversity primarily by gene conversion and hypermutation, e.g., rabbit, pigs, chicken, sheep, cow and horse. The antibodies can be made by immunizing transgenic animals with a desired antigen such as an infectious agent (e.g., bacteria or viruses) or parts or fragments thereof.

Such humanized antibodies have reduced immunogenicity to primates, especially humans, as compared to non-humanized antibodies prepared from non-human animals. Therefore, the humanized antibodies of the present invention are appropriate for use in the therapeutic treatment of human subjects.

Another embodiment of the present invention provides a preparation of humanized antibodies which can be monoclonal antibodies or polyclonal antibodies. Preferred antibody preparations of the present invention are polyclonal antibody preparations which, according to the present invention, have minimal immunogenicity to primates, especially humans.

A preferred preparation of polyclonal antibodies is composed of humanized immunoglobulin molecules having at least a heavy chain or light chain constant region polypeptide sequence encoded by a human constant region gene segment. More preferably, the variable domains of the heavy chains or light chains of the immunoglobulins molecules are also encoded by human gene segments.

In another embodiment, the present invention provides pharmaceutical compositions which include a preparation of humanized antibodies, and a pharmaceutically-acceptable carrier.

Another embodiment of the present invention provides novel sequences from the 5' and 3' flanking regions of the Ig gene segments of non-human animals, preferably, animals which rely primarily on gene conversion in generating the antibody diversity. In particular, the present invention provides novel nucleotide sequences downstream (3', 3-prime) of the genes coding for Cλ in chickens, Cγ and Cκ in rabbits, Cγ1,2,3 in cows and Cγ1,2 in sheep, as well as novel sequences 5' of rabbit Cγ.

In another embodiment, the present invention provides recombination vectors useful for replacing an Ig gene segment of a non-human animal with the corresponding human Ig gene segment. These vectors include a human Ig gene segment which is linked to flanking sequences at the 5' end and the 3' end, wherein the flanking sequences are homologous to the flanking sequences of the target animal Ig gene segment.

Preferred recombination vectors are those useful for the replacement of the animal's Ig constant region. For example, recombination vectors useful for replacing the rabbit heavy chain constant region genes are provided. A preferred vector contains from 5' to 3', a nucleotide sequence as set forth in SEQ ID NO: 12 or SEQ ID NO: 13, or a portion of SEQ ID NO: 12 or SEQ ID NO: 13, a human heavy chain constant region gene segment, a nucleotide sequence as set forth in SEQ ID NO: 10 or a portion of or SEQ ID NO: 10. Another preferred vector contains a nucleotide sequence as set forth in SEQ ID NO: 51, which sequence is characterized as having a human Cγ1 gene linked to flanking sequences from the 5' and 3' flanking regions of a rabbit heavy chain constant region gene.

Recombination vectors are also provided useful for replacing the rabbit light chain constant region genes. A preferred vector contains a nucleotide sequence as set forth in SEQ ID NO: 53, which sequence is characterized as having a human Cκ linked to flanking sequences from the 5' and 3' flanking regions of the rabbit light chain Cκ1 gene.

Other recombination vectors are provided which are useful for replacing the chicken light chain constant region genes. A preferred vector contains a nucleotide sequence as set forth in SEQ ID NO: 57 which is characterized as having a human Cλ2 linked to flanking sequences from the 5' and 3' flanking regions of the chicken light chain Cλ gene.

Other recombination vectors provided include those useful for replacing the animal's Ig V region elements. For example, a recombination vector useful for replacing a rabbit heavy chain V region element is provided and contains SEQ ID NO: 52. A recombination vector useful for replacing a rabbit light chain V region element is provided and contains SEQ ID NO: 54.

In still another embodiment, the present invention provides transgenic constructs or vectors containing at least one humanized Ig locus, i.e., an Ig locus from a non-human animal or a portion of an Ig locus from a non-human animal wherein the locus or the portion of a locus is genetically modified to contain at least one human Ig gene segment. Such humanized Ig locus has the capacity to undergo gene rearrangement and gene conversion in the non-human animal thereby producing a diversified repertoire of humanized immunoglobulins.

One humanized Ig locus provided by the invention is a humanized heavy chain locus which includes one or more V gene segments, one or more D gene segments, one or more J gene segments, and one or more constant region gene segments, wherein at least one gene segment is a human heavy chain gene segment. The gene segments in the humanized heavy chain locus are juxtaposed with respect to each other in an unrearranged, or partially or fully rearranged configuration. A preferred humanized heavy chain locus contains a human constant region gene segment, preferably, Cα or Cγ. A more preferred humanized locus contains multiple V gene segments and at least one human V gene segment, in addition to a human heavy chain constant region segment. The human V gene segment is placed downstream of the non-human V gene segments.

Another humanized Ig locus is a humanized light chain locus which includes one or more V gene segments, one or more J gene segments, and one or more constant region gene segments, wherein at least one gene segment is a human light chain gene segment. The gene segments in the humanized light chain locus are juxtaposed with respect to each other in an unrearranged or rearranged configuration. A preferred humanized light chain locus contains a human constant region gene segment, preferably, Cλ or Cκ. More preferably, the humanized light chain locus further contains multiple V gene segments and at least one human V gene segment. The human V gene segment is placed downstream of the non-human V gene segments. Even more preferably, the humanized light chain locus includes a rearranged human VJ segment, placed downstream of a number of (e.g., 10–100) VL gene segments of either non-human or human origin.

Another embodiment of the present invention is directed to methods of making a transgenic vector containing a humanized Ig locus by isolating an Ig locus or a portion of an Ig locus from a non-human animal, and integrating the desired human Ig gene segment(s) into the isolated animal Ig locus or the isolated portion of an Ig locus. The human Ig gene segment(s) are integrated into the isolated animal Ig locus or the isolated portion of an Ig locus by ligation or homologous recombination in such a way as to retain the capacity of the locus for undergoing effective gene rearrangement and gene conversion in the non-human animal. Integration of a human Ig gene segment by homologous recombination can be accomplished by using the recombination vectors of the present invention.

In another embodiment, the present invention provides methods of making transgenic animals capable of producing humanized antibodies. The transgenic animals can be made by introducing a transgenic vector containing a humanized Ig locus, or a recombination vector containing a human Ig gene segment, into a recipient cell or cells of an animal, and deriving an animal from the genetically modified recipient cell or cells.

Transgenic animals containing one or more humanized Ig loci, and cells derived from such transgenic animals (such as B cells from an immunized transgenic animal) are also provided. The transgenic animals of the present invention are capable of gene rearranging and gene converting the transgenic humanized Ig loci to produce a diversified repertoire of humanized immunoglobulin molecules.

BRIEF DESCRIPTION OF THE DRAWINGS

FIGS. 1(a–d). Cow Cγ 3' flanking sequences. Primers are shown in shaded boxes. The 5' primer is in CH3, and the 3' primer is in M1. The sequences of clone 11, clone 3, and clone 5 are set forth in SEQ ID NO: 3, SEQ ID NO: 4 and SEQ ID NO: 5, respectively.

FIGS. 2(a–e). Sheep Cγ 3' flanking sequences. Primers are shown in shaded boxes. The 5' primer is in CH3, and the 3' primer is in M2. The sequences of clone 11 and clone 1 are set forth in SEQ ID NO: 8 and SEQ ID NO: 9, respectively.

FIGS. 3(a–b). A novel 3' flanking sequence (SEQ ID NO: 10) of the rabbit Cgamma gene.

FIG. 4. A novel nucleotide sequence (SEQ ID NO: 11) 3' of the rabbit Ckappa 1 gene.

FIG. 5. Novel nucleotide sequences (SEQ ID NO: 12 and SEQ ID NO: 13) 5' of the rabbit Cgamma gene. The sequences between SEQ ID NO: 12 and SEQ ID NO: 13 (a gap of about 1000 nt) remain to be determined.

FIG. 6. Comparison of human, mouse, rabbit, sheep, cow and camel sequences for the M1 and M2 regions 3' of the Cgamma gene.

FIG. 7a. DNA construct for the replacement of rabbit Cκ with human Cκ. A 0.5 kb fragment containing a DNA sequence encoding human Ck is flanked by sequences from the rabbit Cκ1 gene. The upstream sequence (5'Cκ) is 2.8 kb, the downstream sequence (3'Cκ) is 2.6 kb. The vector also contains a lox-neo cassette for positive selection and a Hsv-Tk casette for negative selection.

FIG. 7b. DNA construct for the replacement of rabbit Cγ with human Cγ1. A 1.8 kb fragment containing a DNA sequence encoding human Cγ1 is flanked by sequences from the rabbit Cγ gene. The upstream sequence (5'Cγ) is 1.9 kb, the downstream sequence (3'Cγ) is 3.1 kb. The vector also contains a lox-neo casette for positive selection and a Hsv-Tk cassette for negative selection. The figure is not up to scale.

FIG. 8. DNA fragment (SEQ ID NO: 51) containing a human immunoglobulin heavy chain Cγ1 gene segment flanked by 50 nucleotides derived from the flanking regions of rabbit Cγ gene. Flanking sequences derived from the flanking regions of rabbit Cγ gene are underlined.

FIG. 9. DNA fragment (SEQ ID NO: 52) containing a V gene segment with more than 80% sequence identity with rabbit V elements and encoding a human V element polypeptide sequence. Flanking sequences derived from the flanking regions of rabbit VH1 and J genes are underlined.

FIG. 10. DNA fragment (SEQ ID NO: 53) containing a human immunoglobulin heavy chain Cκ gene segment flanked by 50 nucleotides derived from the rabbit light chain immunoglobulin Kappa1 gene. Flanking sequences derived from the flanking regions of rabbit Cκ gene are underlined.

FIG. 11. DNA fragment (SEQ ID NO: 54) containing a V gene segment with more than 80% sequence identity with rabbit V elements and encoding a human V element polypeptide sequence. Flanking sequences derived from the flanking regions of rabbit immunoglobulin V and J genes are underlined.

FIG. 12. DNA fragment (SEQ ID NO: 57) containing a gene encoding human immunoglobulin light chain constant region Clambda2 flanked by 50 nucleotides (underlined) derived from the flanking sequences of chicken Clambda gene.

FIG. 13. Modification of the chicken light chain locus using the ET system. A chicken genomic BAC clone with the full-length light chain locus was modified by homologous recombination. In a first step Cλ was deleted by insertion of a selection cassette which was in a second homologous recombination step exchanged against the human Cλ gene.

FIG. 14. DNA fragment (SEQ ID NO: 58) containing a VJ gene segment with 80% sequence identity with chicken V gene segments and encoding a human VJ immunoglobulin polypeptide. Flanking sequences derived from the flanking regions of chicken immunolgobulin V and J genes are underlined.

FIG. 15. Modified chicken light chain locus.

DETAILED DESCRIPTION OF THE INVENTION

One embodiment of the present invention provides humanized immunoglobulins (antibodies).

By "a humanized antibody" or "a humanized immunoglobulin" is meant an immunoglobulin molecule having at least a portion of a human immunoglobulin polypeptide sequence (or a polypeptide sequence encoded by a human Ig gene segment). The humanized immunoglobulin molecules of the present invention can be isolated from a transgenic non-human animal engineered to produce humanized immunoglobulin molecules. Such humanized immunoglobulin molecules are less immunogenic to primates, especially humans, relative to non-humanized immunoglobulin molecules prepared from the animal or prepared from cells derived from the animal.

The term "non-human animals" as used herein includes, but is not limited to, rabbits, pigs, birds (e.g., chickens, turkeys, ducks, geese and the like), sheep, goats, cows and horses. Preferred non-human animals are those animals which rely primarily on gene conversion and/or somatic hypermutation to generate antibody diversity, e.g., rabbit, pigs, birds (e.g., chicken, turkey, duck, goose and the like), sheep, goat, and cow. Particularly preferred non-human animals are rabbit and chicken.

In animals such as human and mouse, there are multiple copies of V, D and J gene segments on the heavy chain locus, and multiple copies of V and J gene segments on a light chain locus. Antibody diversity in these animals is generated primarily by gene rearrangement, i.e., different combinations of gene segments to form rearranged heavy chain variable region and light chain variable region. In other animals (e.g., rabbit, chicken, sheep, goat, and cow), however, gene rearrangement does not play a significant role in the generation of antibody diversity. For example, in rabbit, only a very limited number of the V gene segments, most often the V gene segments at the 3' end of the V-region, are used in gene rearrangement to form a contiguous VDJ segment. In chicken, only one V gene segment (the one adjacent to the D region, or "the 3' proximal V gene segment"), one D segment and one J segment are used in the heavy chain rearrangement; and only one V gene segment (the 3' proximal V segment) and one J segment are used in the light chain rearrangement. Thus, in these animals, there is little diversity among initially rearranged variable region sequences resulting from junctional diversification. Further diversification of the rearranged Ig genes is achieved by gene conversion, a process in which short sequences derived from the upstream V gene segments replace short sequences within the V gene segment in the rearranged Ig gene.

The term "Ig gene segment" as used herein refers to segments of DNA encoding various portions of an Ig molecule, which are present in the germline of animals and humans, and which are brought together in B cells to form rearranged Ig genes. Thus, Ig gene segments as used herein include V gene segments, D gene segments, J gene segments and C region gene segments.

The term "human Ig gene segment" as used herein includes both naturally occurring sequences of a human Ig gene segment, degenerate forms of naturally occurring sequences of a human Ig gene segment, as well as synthetic sequences that encode a polypeptide sequence substantially identical to the polypeptide encoded by a naturally occurring sequence of a human Ig gene segment. By "substantially" is meant that the degree of amino acid sequence identity is at least about 85%–95%.

A preferred humanized immunoglobulin molecule of the present invention contains at least a portion of a human heavy or light chain constant region polypeptide sequence. A more preferred immunoglobulin molecule contains at least a portion of a human heavy or light chain constant region polypeptide sequence, and at least a portion of a human variable domain polypeptide sequence.

In another embodiment of the present invention, a preparation of humanized antibodies is provided.

By "a preparation of humanized antibodies" or "a humanized antibody preparation" is meant an isolated antibody product or a purified antibody product prepared from a transgenic non-human animal (e.g., serum, milk, or egg yolk of the animal) or from cells derived from a transgenic non-human animal (e.g., a B-cell or a hybridoma cell).

A humanized antibody preparation can be a preparation of polyclonal antibodies, which includes a repertoire of humanized immunoglobulin molecules. A humanized antibody preparation can also be a preparation of a monoclonal antibody.

Although the immunogenicity to humans of a humanized monoclonal antibody preparation is also reduced as compared to a non-humanized monoclonal antibody preparation, humanized polyclonal antibody preparations are preferred embodiments of the present invention. It has been recognized that humanized monoclonal antibodies still invoke some degree of an immune response (an anti-idiotype response) in primates (e.g., humans) when administered repeatedly in large quantities because of the unique and novel idiotype of the monoclonal antibody. The present inventors have uniquely recognized that the overall immunogenicity of polyclonal antibodies is less dependent on an anti-idiotype response. For example, polyclonal antibodies made from non-human animals with only the constant region elements humanized (e.g., polyclonal antibodies having constant regions encoded by human gene segments, and having variable domains encoded by the endogenous genes of the non-human animal), are substantially non-immunogenic to primates.

Without intending to be bound to any theory, the present inventors have proposed that the reduced immunogenicity of such a humanized polyclonal antibody preparation is due to the fact that the preparation contains a very large number of different antibodies with many different idiotypes which are to a large extent defined by novel amino acid sequences in the complimentarily determining regions (CDR) of the heavy and light chain. Therefore, upon administration of such preparation into a primate such as a human, the administered amount of each individual immunoglobulin molecule in the preparation may be too low to solicit immune response against each immunoglobulin molecule. Thus, the humanized polyclonal antibody preparation which has many different idiotypes and variable regions has minimal immunogenicity to a recipient, even if the antibodies in the polyclonal antibody preparation are all directed to the same antigen. To further reduce any potential residual immunogenicity, a humanized polyclonal antibody preparation may be prepared which is composed of immunoglobulin molecules having both the variable domains and the constant regions encoded by human Ig gene segments.

In a preferred embodiment, the present invention provides an antibody preparation which includes humanized immunoglobulin molecules having at least a portion of a human heavy or light chain constant region polypeptide sequence. More preferably, the humanized immunoglobulines in the antibody preparation of the present invention further contain at least a portion of a human variable domain polypeptide sequence, in addition to at least a portion of a human constant region polypeptide sequence.

Preferred humanized antibody preparations of the present invention are composed of humanized antibodies made from transgenic non-human animals whose antibody diversity is generated primarily by gene conversion, such as rabbit, birds (e.g., chicken, turkey, duck, goose and the like), sheep, goat, and cow; preferably, rabbit and chicken.

Once a transgenic non-human animal capable of producing diversified humanized immunoglobulin molecules is made (as further set forth below), humanized immunoglobulins and humanized antibody preparations against an antigen can be readily obtained by immunizing the animal with the antigen. A variety of antigens can be used to immunize a transgenic host animal. Such antigens include, microorganism, e.g. viruses and unicellular organisms (such as bacteria and fungi), alive, attenuated or dead, fragments of the microorganisms, or antigenic molecules isolated from the microorganisms.

Preferred bacterial antigens for use in immunizing an animal include purified antigens from *Staphylococcus aureus* such as capsular polysaccharides type 5 and 8, recombinant versions of virulence factors such as alpha-toxin, adhesin binding proteins, collagen binding proteins, and fibronectin binding proteins. Preferred bacterial antigens also include an attenuated version of *S. aureus, Pseudomonas aeruginosa*, enterococcus, enterobacter, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa*, enterococcus, enterobacter, and *Klebsiella pneumoniae*.

Preferred antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans*.

Preferred antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatits B virus (HBV), cytomegalovirus (CMV), EBV, and HSV.

Therapeutic antibodies can be generated for the treatment of cancer by immunizing transgenic animals with isolated tumor cells or tumor cell lines; tumor-associated antigens which include, but are not limited to, Her-2-neu antigen (antibodies against which are useful for the treatment of breast cancer); CD20, CD22 and CD53 antigens (antibodies against which are useful for the treatment of B cell lymphomas), (3) prostate specific membrane antigen (PMSA) (antibodies against which are useful for the treatment of prostate cancer), and 17-1A molecule (antibodies against which are useful for the treatment of colon cancer).

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, spleen cells are isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", *J Immunol Methods* 242:159 (2000), and by Burton, D. R., "Phage display", *Immunotechnology* 1:87 (1995), the disclosures of which are incorporated herein by reference.

In a further embodiment of the present invention, purified monoclonal or polyclonal antibodies are admixed with an appropriate pharmaceutical carrier suitable for administration in primates especially humans, to provide pharmaceutical compositions. Pharmaceutically acceptable carriers which can be employed in the present pharmaceutical compositions can be any and all solvents, dispersion media, isotonic agents and the like. Except insofar as any conventional media, agent, diluent or carrier is detrimental to the recipient or to the therapeutic effectiveness of the antibodies contained therein, its use in the pharmaceutical compositions of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

The present invention is further directed to novel nucleotide sequences and vectors, as well as the use of the sequences and vectors in making a transgenic non-human animal which produces humanized immunoglobulins.

In general, the genetic engineering of a non-human animal involves the integration of one or more human Ig gene segments into the animal's genome to create one or more humanized Ig loci. It should be recognized that, depending upon the approach used in the genetic modification, a human Ig gene segment can be integrated at the endogenous Ig locus of the animal (as a result of targeted insertion, for example), or at a different locus of the animal. In other words, a humanized Ig locus can reside at the chromosomal location where the endogenous Ig locus of the animal ordinarily resides, or at a chromosomal location other than where the endogenous Ig locus of the animal ordinarily resides. Regardless of the chromosomal location, a humanized Ig locus of the present invention has the capacity to undergo gene rearrangement and gene conversion in the non-human animal thereby producing a diversified repertoire of humanized immunoglobulin molecules. An Ig locus having the capacity to undergo gene rearrangement and gene conversion is also referred to herein as a "functional" Ig locus, and the antibodies with a diversity generated by a functional Ig locus are also referred to herein as "functional" antibodies or a "functional" repertoire of antibodies.

In one embodiment, the present invention provides novel sequences useful for creating a humanized Ig locus and making transgenic animals capable of producing humanized immunoglobulin molecules. In particular, the present invention provides sequences from the 5' and 3' flanking regions of the Ig gene segments of non-human animals, preferably, animals which rely primarily on gene conversion in generating antibody diversity (e.g., rabbit, pigs, sheep, goat, cow, birds such as chicken, turkey, duck, goose, and the like).

The 5' and 3' flanking regions of the genes coding for the constant region are particularly important as these sequences contain untranslated regulatory elements (e.g., enhancers) critical for high Ig expression in the serum. The 3' flanking region of the genes coding for the constant region of the heavy chain also contain exons coding for the membranous and cytoplasmic tail of the membrane form of immunoglobulin (Volgina et al. *J Immunol* 165:6400, 2000). It has been previously established that the membrane and cytoplasmic tail of the membrane form of antibodies are critical in achieving a high level of expression of the antibodies in mice sera (Zou et al., *Science* 262:1271, 1993). Thus, the identification of the flanking sequences permits the replacement of exons and intervening introns of the Cγ gene with the human equivalent, and the maintenance of the endogenous exons encoding the transmembrane and cytoplasmic tail regions as well as the endogenous non-coding enhancer sequences.

In one embodiment, the present invention provides 3' flanking sequences of heavy chain constant regions of non-human animals. More particularly, nucleotide sequences downstream (3', 3-prime) of the genes coding for rabbit Cγ, cow Cγ1,2,3, and sheep Cγ1,2 are provided. Especially preferred nucleotide sequences include SEQ ID NO: 10 (3' of rabbit Cγ), SEQ ID NOS: 3–5 (3' of cow Cγ1,2,3), and SEQ ID NOS: 8–9 (3' of sheep Cγ1,2).

In another embodiment, the present invention provides 3' flanking sequences of light chain constant regions of non-human animals. More particularly, the present invention provides nucleotide sequences downstream (3', 3-prime) of the genes coding for Cκ in rabbits. Especially preferred nucleotide sequences include SEQ ID NO: 11 (3' of rabbit Cκ).

In still another embodiment, the present invention provides 5' flanking sequences of heavy chain constant regions of non-human animals. More particularly, nucleotide sequences upstream (5', 5-prime) of the rabbit Cγ gene are provided. Especially preferred sequences include SEQ ID NO: 12 and SEQ ID NO: 13.

Another embodiment of the present invention provides 5' flanking sequences of light chain constant regions of non-human animals.

Portions of the above novel flanking sequences are provided by the present invention. By "a portion" is meant a fragment of a flanking nucleotide sequence capable of mediating homologous recombination between the human Ig gene segment and the target animal Ig gene segment. Generally, a portion is at least about 200 base pairs, preferably, at least about 400 base pairs, for recombination in animal cells such as ES cells or fibroblasts, and at least about 40 base pairs, preferably at least about 50 base pairs, for recombination in *E. coli*. Examples of portions of the above novel flanking sequences include SEQ ID NOS: 59–60, 61–62, 63–64, 65–66, 67–68 and 69–70 (represented by the underlined sequences in FIGS. 8–12 and 14, respectively).

In a further aspect, the present invention provides vectors useful for the replacement of an Ig gene segment of a non-human animal with the corresponding human Ig gene segment. These vectors, also referred to herein as "recombination vectors", include a human Ig gene segment which is linked to flanking sequences at the 5' end and the 3' end, wherein the flanking sequences have a degree of homology with the flanking sequences of the target animal Ig gene segment sufficient to mediate homologous recombination between the human gene and the animal gene segments. Generally, at least about 200 bases should be identical between the flanking regions in a recombination vector and the flanking regions of the target gene to achieve efficient homologous recombination in animal cells such as ES cells and fibroblasts; and at least about 40 bases should be identical to achieve efficient homologous recombination in *E. coli*.

Recombination vectors useful for replacing the animal's immunoglobulin heavy chain constant region genes are provided, which contain from 5' to 3', a nucleotide sequence homologous to the 5' flanking region of the target animal heavy chain constant region gene, a human heavy chain constant region gene (e.g., human Cγ1), and a nucleotide sequence homologous to the 3' flanking region of the target animal heavy chain constant region gene.

Preferred recombination vectors are provided for the replacement of the rabbit heavy chain constant region genes. One such vector contains from 5' to 3', a nucleotide sequence as set forth in SEQ ID NO: 12 or SEQ ID NO: 13 or a portion thereof, a human heavy chain constant region gene segment, a nucleotide sequence as set forth in SEQ ID NO: 10 or a portion of or SEQ ID NO: 10. Another such vector contains SEQ ID NO: 51 (FIG. 8) which is characterized as having a human Cγ1 gene linked to flanking sequences from the 5' and 3' flanking regions of a rabbit heavy chain constant region gene.

Recombination vectors are also provided which are useful for replacing the animal's immunoglobulin light chain constant region genes. Such vectors contain from 5' to 3', a nucleotide sequence homologous to the 5' flanking region of the target light chain constant region gene, a human light chain constant region gene (e.g., human Cκ or Cλ), and a nucleotide sequence homologous to the 3' flanking region of the target light chain constant region gene.

Preferred vectors include those useful for replacing the rabbit light chain constant region genes. A preferred vector contains a nucleotide sequence as set forth in SEQ ID NO: 53, which sequence is characterized as having a human Cκ linked to flanking sequences from the 5' and 3' flanking regions of the rabbit light chain Cκ1 gene.

Other recombination vectors provided include those useful for replacing the animal's Ig V region elements. For example, a recombination vector useful for replacing a rabbit heavy chain V region element is provided and contains SEQ ID NO: 52. A recombination vector useful for replacing a rabbit light chain V region element is provided and contains SEQ ID NO: 54.

The recombination vectors of the present invention can include additional sequences that facilitate the selection of cells which have undergone a successful recombination event. For example, marker genes coding for resistance to neomycin, bleomycin, puromycin and the like can be included in the recombination vectors to facilitate the selection of cells which have undergone a successful recombination event.

In a further aspect of the present invention, transgenic constructs or vectors carrying one or more humanized Ig loci are provided.

In one embodiment, the present invention provides transgenic constructs containing a humanized Ig heavy chain locus which includes one or more V gene segments, one or more D gene segments, one or more J gene segments, and one or more constant region gene segments, wherein at least one gene segment is a human heavy chain gene segment. The gene segments in such humanized heavy chain locus are juxtaposed wit respect to each other in an unrearranged configuration (or "the germline configuration"), or in a partially or fully rearranged configuration. The humanized heavy chain locus has the capacity to undergo gene rearrangement (if the gene segments are not fully rearranged) and gene conversion in the non-human animal thereby producing a diversified repertoire of heavy chains having human polypeptide sequences, or "humanized heavy chains".

In a preferred embodiment, the humanized heavy chain locus contains at least one C-region gene segment that is a human constant region gene segment, preferably, Cα or Cγ (including any of the Cγ subclasses 1, 2, 3 and 4).

In another more preferred embodiment, the humanized heavy chain locus of the transgene contains a humanized V-region and a humanized C-region, i.e., a V-region having at least one human VH gene segment and a C-region having at least one human C gene segment (e.g., human Cα or Cγ).

Preferably, the humanized V-region includes at least about 10–100 heavy chain V (or "VH") gene segments, at least one of which is a human VH gene segment. In accordance with the present invention, the human VH gene segment included in the transgene shares at least about 75% to about 85% homology to the VH gene segments of the host animal, particularly those animal VH gene segments included in the upstream region of the transgene. As described above, a human VH segment encompasses naturally occurring sequences of a human VH gene segment, degenerate forms of naturally occurring sequences of a human VH gene segment, as well as synthetic sequences that encode a polypeptide sequence substantially (i.e., at least about 85%–95%) identical to a human heavy chain V domain polypeptide.

Preferably, the human VH gene segment(s) is placed downstream of the non-human VH segments in the transgene locus. Preferably, the non-human VH gene segments in the transgene are the VH gene segments from the 3' VH-region in the Ig locus of the host animal, including the 3' proximal VH1.

In another embodiment, the present invention provides transgenic constructs containing a humanized light chain locus capable of undergoing gene rearrangement and gene conversion in the host animal thereby producing a diversified repertoire of light chains having human polypeptide sequences, or "humanized light chains".

The humanized light locus includes one or more V gene segments, one or more J gene segments, and one or more constant region gene segments, wherein at least one gene segment is a human light chain gene segment. The gene segments in the humanized light chain locus are juxtaposed in an unrearranged configuration (or "the germline configuration"), or fully rearranged configuration.

In a preferred embodiment, the humanized light chain locus contains at least one C-region gene segment that is a human constant region gene segment, preferably, Cλ or Cκ.

In another preferred embodiment, the humanized light chain locus of the transgene contains a humanized V-region and a humanized C-region, e.g., a V-region having at least one human VL gene and/or at least one rearranged human VJ segment, and a C-region having at least one human C gene segment (e.g., human Cλ or Cκ).

Preferably, the humanized V-region includes at least about 10–100 light chain V (or "VL") gene segments, at least one of which is a human VL gene segment. The human VL gene segment included in the transgene shares at least about 75% to about 85% homology to the VL gene segments of the host animal, particularly those animal VL gene segments included in the upstream region of the transgene. Consistently, a human VL segment encompasses naturally occurring sequences of a human VL gene segment, degenerate forms of naturally occurring sequences of a human VL gene segment, as well as synthetic sequences that encode a polypeptide sequence substantially (i.e., at least about 85%–95%) identical to a human light chain V domain polypeptide.

Preferably, the human VL gene segment(s) is placed downstream of the non-human VL segments in the transgene locus. The non-human VL gene segments in the transgene construct are selected from the VL gene segments in the 3'VL-region in the light chain locus of the host animal, including the 3' proximal VL1.

In still another preferred embodiment, the humanized light chain locus includes a rearranged human VJ segment, placed downstream of a number of (e.g., 10–100) VL gene segments of either non-human or human origin.

Another aspect of the present invention is directed to methods of making a transgenic vector containing a humanized Ig locus. Such methods involve isolating an Ig locus or a portion thereof from a non-human animal, and inserting the desired human Ig gene segment(s) into the isolated animal Ig locus or the isolated portion of an animal Ig locus. The human Ig gene segment(s) are inserted into the isolated animal Ig locus or a portion thereof by ligation or homologous recombination in such a way as to retain the capacity of the locus of undergoing effective gene rearrangement and gene conversion in the non-human animal.

Preferably, DNA fragments containing an Ig locus to be humanized are isolated from animals which generate antibody diversity by gene conversion, e.g., rabbit and chicken. Such large DNA fragments can be isolated by screening a library of plasmids, cosmids, YACs or BACs, and the like, prepared from the genomic DNA of the non-human animal. An entire animal C-region can be contained in one plasmid or cosmid clone which is subsequently subjected to humanization. YAC clones can carry DNA fragments of up to 2 megabases, thus an entire animal heavy chain locus or a large portion thereof can be isolated in one YAC clone, or reconstructed to be contained in one YAC clone. BAC clones are capable of carrying DNA fragments of smaller sizes (about 150–250 kb). However, multiple BAC clones containing overlapping fragments of an Ig locus can be separately humanized and subsequently injected together into an animal recipient cell, wherein the overlapping fragments recombine in the recipient animal cell to generate a continuous Ig locus.

Human Ig gene segments can be integrated into the Ig locus on a vector (e.g., a BAC clone) by a variety of methods, including ligation of DNA fragments, or insertion of DNA fragments by homologous recombination. Integration of the human Ig gene segments is done in such a way that the human Ig gene segment is operably linked to the host animal sequence in the transgene to produce a functional humanized Ig locus, i.e., an Ig locus capable of gene rearrangement and gene conversion which lead to the production of a diversified repertoire of humanized antibodies.

Preferably, human Ig gene segments are integrated into the Ig locus by homologous recombination. Homologous recombination can be performed in bacteria, yeast and other cells with a high frequency of homologous recombination events. For example, a yeast cell is transformed with a YAC containing an animal's Ig locus or a large portion thereof. Subsequently, such yeast cell is further transformed with a recombination vector as described hereinabove, which carries a human Ig gene segment linked to a 5' flanking sequence and a 3' flanking sequence. The 5' and the 3' flanking sequences in the recombination vector are homologous to those flanking sequences of the animal Ig gene segment on the YAC. As a result of a homologous recombination, the animal Ig gene segment on the YAC is replaced with the human Ig gene segment. Alternatively, a bacterial cell such as E. coli is transformed with a BAC containing an animal's Ig locus or a large portion thereof. Such bacterial cell is further transformed with a recombination vector which carries a human Ig gene segment linked to a 5' flanking sequence and a 3' flanking sequence. The 5' and the 3' flanking sequences in the recombination vector mediate homologous recombination and exchange between the human Ig gene segment on the recombination vector and the animal Ig gene segment on the BAC. Humanized YACs and BACs can be readily isolated from the cells and used in making transgenic animals.

In a further aspect of the present invention, methods of making transgenic animals capable of producing humanized immunoglobulins are provided.

According to the present invention, a transgenic animal capable of making humanized immunoglobulins are made by introducing into a recipient cell or cells of an animal one or more of the transgenic vectors described herein above which carry a humanized Ig locus, and deriving an animal from the genetically modified recipient cell or cells.

Preferably, the recipient cells are from non-human animals which generate antibody diversity by gene conversion and hypermutation, e.g., bird (such as chicken), rabbit, cows and the like. In such animals, the 3'proximal V gene segment is preferentially used for the production of immunoglobulins. Integration of a human V gene segment into the Ig locus on the transgene vector, either by replacing the 3'proximal V gene segment of the animal or by being placed in close proximity of the 3'proximal V gene segment, results in expression of human V region polypeptide sequences in the majority of immunoglobulins. Alternatively, a rearranged human V(D)J segment may be inserted into the J locus of the immunoglobulin locus on the transgene vector.

The transgenic vectors containing a humanized Ig locus is introduced into the recipient cell or cells and then integrated into the genome of the recipient cell or cells by random integration or by targeted integration.

For random integration, a transgenic vector containing a humanized Ig locus can be introduced into an animal recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells and subsequently injecting the genetically modified embryonic stem cells into developing embryos. Alternatively, a transgenic vector (naked or in combination with facilitating reagents) can be directly injected into a developing embryo. Ultimately, chimeric transgenic animals are produced from the embryos which contain the humanized Ig transgene integrated in the genome of at least some somatic cells of the transgenic animal.

In a preferred embodiment, a transgene containing a humanized Ig locus is randomly integrated into the genome of recipient cells (such as fertilized oocyte or developing embryos) derived from animal strains with an impaired expression of endogenous immunoglobulin genes. The use of such animal strains permits preferential expression of immunoglobulin molecules from the humanized transgenic Ig locus. Examples for such animals include the Alicia and Basilea rabbit strains, as well as Agammaglobinemic chicken strain. Alternatively, transgenic animals with humanized immunoglobulin transgenes or loci can be mated with animal strains with impaired expression of endogenous immunoglobulins. Offspring homozygous for an impaired endogenous Ig locus and a humanized transgenic Ig locus can be obtained.

For targeted integration, a transgenic vector can be introduced into appropriate animal recipient cells such as embryonic stem cells or already differentiated somatic cells. Afterwards, cells in which the transgene has integrated into the animal genome and has replaced the corresponding endogenous Ig locus by homologous recombination can be selected by standard methods. The selected cells may then be fused with enucleated nuclear transfer unit cells, e.g. oocytes or embryonic stem cells, cells which are totipotent and capable of forming a functional neonate. Fusion is performed in accordance with conventional techniques which are well established. See, for example, Cibelli et al., Science (1998) 280:1256. Enucleation of oocytes and nuclear transfer can also be performed by microsurgery using injection pipettes. (See, for example, Wakayama et al., Nature (1998) 394:369.) The resulting egg cells are then cultivated in an appropriate medium, and transferred into synchronized recipients for generating transgenic animals. Alternatively, the selected genetically modified cells can be injected into developing embryos which are subsequently developed into chimeric animals.

Further to the present invention, a transgenic animal capable of producing humanized immunoglobulins can also be made by introducing into a recipient cell or cells, one or more of the recombination vectors described herein above, which carry a human Ig gene segment, linked to 5' and 3' flanking sequences that are homologous to the flanking sequences of the endogenous Ig gene segment, selecting cells in which the endogenous Ig gene segment is replaced by the human Ig gene segment by homologous recombination, and deriving an animal from the selected genetically modified recipient cell or cells.

Similar to the target insertion of a transgenic vector, cells appropriate for use as recipient cells in this approach include embryonic stem cells or already differentiated somatic cells. A recombination vector carrying a human Ig gene segment can be introduced into such recipient cells by any feasible means, e.g., transfection. Afterwards, cells in which the human Ig gene segment has replaced the corresponding endogenous Ig gene segment by homologous recombination, can be selected by standard methods. These genetically modified cells can serve as nuclei donor cells in a nuclear transfer procedure for cloning a transgenic animal. Alternatively, the selected genetically modified embryonic stem cells can be injected into developing embryos which can be subsequently developed into chimeric animals.

Transgenic animals produced by any of the foregoing methods form another embodiment of the present invention. The transgenic animals have at least one, i.e., one or more, humanized Ig loci in the genome, from which a functional repertoire of humanized antibodies is produced.

In a preferred embodiment, the present invention provides transgenic rabbits having one or more humanized Ig loci in the genome. The transgenic rabbits of the present invention are capable of rearranging and gene converting the humanized Ig loci, and expressing a functional repertoire of humanized antibodies.

In another preferred embodiment, the present invention provides transgenic chickens having one or more humanized Ig loci in the genome. The transgenic chickens of the present invention are capable of rearranging and gene converting the humanized Ig loci, and expressing a functional repertoire of humanized antibodies.

Cells derived from the transgenic animals of the present invention, such as B cells or cell lines established from a transgenic animal immunized against an antigen, are also part of the present invention.

In a further aspect of the present invention, methods are provided for treating a disease in a primate, in particular, a human subject, by administering a purified humanized antibody composition, preferably, a humanized polyclonal antibody composition, desirable for treating such disease.

The humanized polyclonal antibody compositions used for administration are generally characterized by containing a polyclonal antibody population, having immunoglobulin concentrations from 0.1 to 100 mg/ml, more usually from 1 to 10 mg/ml. The antibody composition may contain immunoglobulins of various isotypes. Alternatively, the antibody composition may contain antibodies of only one isotype, or a number of selected isotypes.

In most instances the antibody composition consists of unmodified immunoglobulins, i.e., humanized antibodies prepared from the animal without additional modification, e.g., by chemicals or enzymes. Alternatively, the immunoglobulin fraction may be subject to treatment such as enzymatic digestion (e.g. with pepsin, papain, plasmin, glycosidases, nucleases, etc.), heating, etc, and/or further fractionated.

The antibody compositions generally are administered into the vascular system, conveniently intravenously by injection or infusion via a catheter implanted into an appropriate vein. The antibody composition is administered at an appropriate rate, generally ranging from about 10 minutes to about 24 hours, more commonly from about 30 minutes to about 6 hours, in accordance with the rate at which the liquid can be accepted by the patient. Administration of the effective dosage may occur in a single infusion or in a series of infusions. Repeated infusions may be administered once a day, once a week once a month, or once every three months, depending on the half-life of the antibody preparation and the clinical indication. For applications on epithelial surfaces the antibody compositions are applied to the surface in need of treatment in an amount sufficient to provide the intended end result, and can be repeated as needed.

The antibody compositions can be used to bind and neutralize antigenic entities in human body tissues that cause disease or that elicit undesired or abnormal immune responses. An "antigenic entity" is herein defined to encompass any soluble or cell-surface bound molecules including proteins, as well as cells or infectious disease-causing organisms or agents that are at least capable of binding to an antibody and preferably are also capable of stimulating an immune response.

Administration of an antibody composition against an infectious agent as a monotherapy or in combination with chemotherapy results in elimination of infectious particles. A single administration of antibodies decreases the number of infectious particles generally 10 to 100 fold, more commonly more than 1000-fold. Similarly, antibody therapy in patients with a malignant disease employed as a monotherapy or in combination with chemotherapy reduces the number of malignant cells generally 10 to 100 fold, or more than 1000-fold. Therapy may be repeated over an extended amount of time to assure the complete elimination of infectious particles, malignant cells, etc. In some instances, therapy with antibody preparations will be continued for extended periods of time in the absence of detectable amounts of infectious particles or undesirable cells. Similarly, the use of antibody therapy for the modulation of immune responses may consist of single or multiple administrations of therapeutic antibodies. Therapy may be continued for extended periods of time in the absence of any disease symptoms.

The subject treatment may be employed in conjunction with chemotherapy at dosages sufficient to inhibit infectious disease or malignancies. In autoimmune disease patients or transplant recipients, antibody therapy may be employed in conjunction with immunosuppressive therapy at dosages sufficient to inhibit immune reactions.

The invention is further illustrated, but by no means limited, by the following examples.

EXAMPLE 1

Novel Sequences 3'Prime of the Cγ Gene from Cows, Sheep and Rabbits

Genomic DNA was isolated from blood of a Simmental cow using the QIAamp DNA Blood Kit (QIAGEN). The genomic region 3' of the cow Cγ gene (i.e., the cow Cγ gene 3' flanking sequence) was PCR-amplified using the isolated genomic DNA as template and the following primers:

5' primer: 5'cgcaagcttCCTACACGTGTGTGGTGATG3'; (SEQ ID NO: 1)

3' primer: 5'cgcaagcttAAGATGGWGATGGTSGTCCA3' (SEQ ID NO: 2)

(Universal degenerate code: W = (A/T) S = (G/C)).

The upper-case portion of the 5' primer was from exon 3 of Cγ, and the lower-case portion represented a terminal HindIII restriction site. The upper-case portion of the 3' primer was a degenerate sequence designed according to the published sequences from the human M1 exon and the mouse M1 exon, and the lower-case portion represented a terminal HindIII restriction site. A 1.3 kb PCR fragment was obtained using the EXPAND long template PCR system (Roche). The fragment was gel purified, digested with HindIII, and cloned into a Bluescript cloning vector. The resulting clones fell into three populations, which differ from one another in the pattern of the restriction fragments obtained with BamHI, EcoRI and XhoI. One clone from each population was sequenced, and the sequences are shown in FIG. 1 (SEQ ID NOS: 3–5).

Genomic DNA was isolated from blood of a Merino sheep using the QIAamp DNA Blood Kit (QIAGEN). The genomic region 3' of the sheep Cγ gene (i.e., the sheep Cγ gene 3' flanking sequence) was PCR-amplified using the isolated genomic DNA as template and the following primers:

5' primer: 5'cgcggatccCCTACGCGTGTGTGGTGATG3' (SEQ ID NO: 6)

3' primer: 5'cgcggatccACCGAGGAGAAGATCCACTT3' (SEQ ID NO: 7)

The upper-case portion of the 5' primer was from exon 3 of Cγ, and the lower-case portion represented a terminal BamHI restriction site. The upper-case portion of the 3' primer was designed according to the published sequences from the human M2 exon and the mouse M2 exon, and the lower-case portion represented a terminal BamHI restriction site. A 2.9 kb PCR fragment was obtained using the EXPAND long template PCR system (Roche). The fragment was gel purified, digested with BamHI, and cloned into a Bluescript cloning vector. The resulting clones fell into two populations, which differ from each other in the pattern of the restriction fragments obtained with HindIII, EcoRI and XhoI. One clone from each population was sequenced, and the sequences are shown in FIG. 2 (SEQ ID NOS: 8–9).

A 10 kb EcoRI fragment containing the Cγ gene and its flanking sequences from A2 allotype rabbit was subcloned from a genomic cosmid clone (cos 8.3 from Knight et al., *J Immunol* (1985) 1245–50, "Organization and polymorphism of rabbit immunoglobulin heavy chain genes"). The nucleotide sequences 5' and 3' of Cγ were determined using standard methods and are set forth in FIGS. 3 and 5, SEQ ID NO: 10, 12, 13, respectively.

Sequences 3' of rabbit Ckappa1 were determined from an EcoRI/BamHI subclone from VJk2Ck In pSV2neo. The nucleotide sequence is set forth in FIG. 4, SEQ ID NO: 11.

The amino acid sequences encoded by the M1 and M2 exons from cow, sheep and rabbit were deduced from the above 3' flanking sequence. These amino acid sequences were aligned with the published M1 and M2 sequences from camel, human and mouse, as shown in FIG. 6.

EXAMPLE 2

A Vector for Replacing the Rabbit Endogenous Cγ Gene Segment with the Human Cγ1 Segment Genomic DNA is isolated from rabbit fetal fibroblasts of an a2-homozygous rabbit. The DNA sequence upstream of rabbit Cγ (i.e., the 5' flanking sequence of rabbit Cγ) is amplified by PCR using the following primers:

5' taattatgcggccgcCTTCAGCGTGAACCACGCCCTC 3' (SEQ ID NO: 39) with a 5' NotI site and

5' GTCGACGCCCCTCGATGCACTCCCAGAG 3'(SEQ ID NO: 40).

The DNA sequence downstream of rabbit Cγ (i.e., the 3' flanking sequence of rabbit Cγ) is amplified with the following primers:

5' ggtaccCTCTCCCTCCCCCACGCCGCAGC 3' (SEQ ID NO: 41) with a 5' NpnI site and

5' atattcagaACTGGCTGTCCCTGCTGTAGTACACGG 3' (SEQ ID NO: 42) with a 5' NhoI site.

Human genomic DNA is isolated from human peripheral blood lymphocytes. The DNA fragment encoding human Cγ1 is amplified using the following primers:

5' GTCGACACTGGACGCTGAACCTCGCGG 3' (SEQ ID NO: 43)

and

5' GGTACCGGGGGCTTGCCGGCCGTCGCAC 3'. (SEQ ID NO: 44)

The fragments are digested with restriction enzymes and cloned into a Bluescript vector. Subsequently, a lox neocassette is inserted into the SalI site and an Hsv-tk cassette into the XhoI site. A schematic drawing of the final construct is shown in FIG. 7a.

EXAMPLE 3

A Vector for Replacing the Rabbit Endogenous Cκ Gene Segment with the Human Cκ Segment Genomic DNA was isolated from rabbit fetal fibroblasts of a b5-homozygous rabbit. The DNA sequence upstream of rabbit Cκ1 (i.e., the 5' flanking sequence of rabbit Cκ1) was amplified by PCR using the following primers:

5' gcggccgcTGGCGAGGAGACCAAGCTGGAGATCAAACG 3' (SEQ ID NO: 45)

with a 5' NotI site

5' GTCGACGCAGCCCAAAGCTGTTGCAATGGGGCAGCG 3'. (SEQ ID NO: 46)

The DNA sequence downstream of rabbit Cκ1 (i.e., the 5' flanking sequence of rabbit Cκ1) was amplified with the following primers:

5' atatggtaccGCGAGACGCCTGCCAGGGCACCGCC 3' (SEQ ID NO: 47) with a 5' NpnI site

5' GGATCCCGAGCTTTATGGGCAGGGTGGGGG 3' (SEQ ID NO: 48).

Human genomic DNA was isolated from human peripheral blood lymphocytes. The DNA fragment encoding human Cκ was amplified using the following primers:

```
                                           (SEQ ID NO: 49)
5' ATATGTCGACCTGGGATAAGCATGCTGTTTTCTGTCTGTCCC 3'

(SEQ ID NO: 50)
5' CTAGGTACCAGCAGGTGGGGCACTTCTCCC 3'.
```

The fragments were digested with restriction enzymes and cloned into a Bluescript vector. Subsequently, a lox neo-cassette was inserted into the SalI site and an Hsv-tk cassette into the XhoI site. A schematic drawing of the final construct is shown in FIG. 7b.

EXAMPLE 4

Replacement of the Endogenous Cγ and Cκ Gene Segments in Rabbit Fetal Fibroblasts with the Corresponding Human Gene Segments Rabbit fetal fibroblast cells are prepared by standard methods. After one passage, fibroblasts are transfected with 5 µg of the NotI-linearized targeting vector as shown in FIG. 5a for Cγ or FIG. 5b for Cκ, and are seeded in 96-well plates ($2\times10^3$ cells/well). After a positive selection with 600 µg/ml G418 and a negative selection with 200 nM FIAU, resistant colonies are replica-plated to two 96-well plates for DNA analysis and cryopreservation, respectively. PCR and/or Southern blot analysis is performed to identify cells with the human Cγ1 gene segment integrated in the genome. The cells having the integrated human Cγ1 gene are used in rabbit cloning as described in Example 5.

EXAMPLE 5

Cloning of Rabbits

Mature Dutch Belton rabbits are superovulated by subcutaneous injection of follicle stimulating hormone (FSH) every 12 hours (0.3 mg×2 and 0.4 mg×4). Ovulation is induced by intravenous administration of 0.5 mg luteinizing hormone (LH) 12 hours after the last FSH injection. Oocytes are recovered by oviducal flush 17 hours after LH injection. Oocytes are mechanically enucleated 16–19 hours after maturation. Chromosome removal is assessed with bisBENZIMIDE (HOECHST 33342, Sigma, St. Louis, Mo.) dye under ultraviolet light. Enucleated oocytes are fused with actively dividing fibroblasts by using one electrical pulse of 180 V/cm for 15 us (Electrocell Manipulator 200, Genetronics, San Diego, Calif.). After 3–5 hours oocytes are chemically activated with calcium ionophore (6 uM) for 4 min (# 407952, Calbiochem, San Diego, Calif.) and 2 mM 6-dimethylaminopurine (DMAP, Sigma) in CR2 medium (Specialty Media, Lavalett, N.J.) with 3 mg/ml bovine serum albumin (fatty acid free, Sigma) for 3 hours. Following the activation, the embryos are washed in hamster embryo culture medium (HECM)-Hepes five times and subsequently, cultivated in CR2 medium containing 3 mg/ml fatty-acid free BSA for 2–48 hours at 37.8° C. and 5% $CO_2$ in air. Embryos are then transferred into synchronized recipients. Offsprings are analyzed by PCR for a segment of the transgene.

EXAMPLE 6

Construction of a DNA Fragment Containing a Portion of a Rabbit Heavy Chain Locus with a Human Cγ1 Gene Segment and a VH Gene Segment Encoding a Human VH Domain Polypeptide Sequence The upstream and downstream regions (i.e., the 5' and 3' flanking regions) of the rabbit heavy chain Cγ gene from an a2-allotype rabbit were sequenced. A DNA fragment (SEQ ID NO: 51) is generated by PCR using overlapping oligonucleotides wherein the DNA fragment contains from 5' to 3', a sequence derived from the 5' flanking region of the rabbit Cγ gene, the human Cγ1 gene, and a sequence derived from the 3' flanking region of the rabbit Cγ gene (FIG. 8).

A genomic BAC library derived from an a2-allotype rabbit is generated by standard procedures and screened with probes specific for rabbit Cγ. A BAC clone containing rabbit heavy chain gene segments is identified. The rabbit Cγ gene on this BAC clone is replaced with the human Cγ1 gene by homologous recombination in *E.coli* using the DNA fragment of SEQ ID NO: 51 and the pET system. This replacement is accomplished by two consecutive recombination steps: first the rabbit Cγ gene segment is replaced with a marker gene; then the marker gene is replaced the human Cγ1 gene segment.

The modified BAC clone containing rabbit heavy chain genes and the inserted human Cγ1 gene is further modified by replacing the 3'proximal VH1 segment with a synthetic VH gene segment (FIG. 9). This synthetic VH gene segment (SEQ ID NO: 52) is made using overlapping oligoncuelotides and includes a 5' flanking sequence, a 3' flanking sequence, and a sequence coding for a polypeptide nearly identical to the human immunoglobulin heavy chain variable domain polypeptide sequence described by Huang and Stollar (*J. Immunol.* 151: 5290–5300, 1993). The coding sequence of the synthetic VH gene segment is designed based on the published sequence of a rabbit VH1 gene (a2, Knight and Becker, *Cell* 60:963–970, 1990) and is more than 80% identical to rabbit VH gene segments. The 5' and the 3' flanking sequences in the synthetic VH segment are derived from the upstream and downstream regions of the a2-allotype rabbit VH1 gene. The synthetic VH gene of SEQ ID NO: 52 is used to replace the rabbit VH1 gene on the BAC clone by homologous recombination using the pET or the redεβγ system. The modified BAC clone is amplified and purified using standard procedures.

EXAMPLE 7

Construction of a DNA Fragment Containing a Portion of a Rabbit Light Chain Locus with a Human Cκ Gene Segment and a VJ Gene Segment Encoding a Human VL Domain Polypeptide Sequence The upstream and downstream regions (i.e., the 5' and 3' flanking regions) of the rabbit light chain Cκ1 gene from a b5-allotype rabbit were sequenced. A DNA fragment (SEQ ID NO: 53) is generated by PCR using overlapping oligonucleotides wherein the DNA fragment contains from 5' to 3', a sequence derived from the 5' flanking region of the rabbit Cκ1 gene, the human Cκ1 gene, and a sequence derived from the 3' flanking region of the rabbit Cκ1 gene (FIG. 10).

A genomic BAC library derived from a b5-allotype rabbit is generated by standard procedures and screened with probes specific for rabbit Cκ1. A BAC clone containing rabbit light chain gene segments is identified. The rabbit Cκ1 gene on this BAC clone is replaced with the human Cκ1 gene on the DNA fragment of SEQ ID NO: 53 by homologous recombination in *E. coli* using the pET or the redεβγ system. This replacement is accomplished by two consecutive recombination steps: first the rabbit Cκ1 gene segment is replaced with a marker gene; then the marker gene is replaced the human Cκ1 gene segment.

The modified BAC clone containing rabbit light chain genes and the inserted human Cκ1 gene is further modified by inserting a rearranged VJ DNA fragment into the J region of the rabbit light chain locus. The rearranged VJ DNA fragment encodes a human immunoglobulin variable domain polypeptide described by Pritsch et al. (*Blood* 82(10):3103–3112, 1993) and Lautner-Rieske et al. (*Eur. J. Immunol.* 22 (4), 1023–1029, 1992)) (FIG. 7). The nucleotide sequence of the rearranged VJ fragment is designed to maximize the sequence homology at the nucleotide level to the rabbit Vkappa sequence published by Lieberman et al. (*J. Immunol.* 133 (5), 2753–2756, 1984). This rearranged VJ DNA sequence is more than 80% identical with known rabbit Vκ genes. Using overlapping oligonucleotides in PCR, the rearranged VJ DNA fragment is linked to a 5' and a 3' flanking sequence, resulting the DNA fragment of SEQ ID NO: 54 (FIG. 11). The 5'flanking sequence is derived from 5' of a rabbit Vκ, the 3'flanking sequence is derived from 3' of rabbit J2. The DNA fragment of SEQ ID NO: 54 is subsequently inserted into the rabbit light chain locus by homologous recombination in *E. coli* using the pET or the redεβγ system. The insertion is performed in such a way that the rabbit light chain region containing the rabbit Vκ1 gene segment, the rabbit J1 and J2 segments, and the sequences in between, is replaced with the rearranged VJ DNA fragment. Again, this insertion is accomplished by replacement of the rabbit V to J region with a marker gene, followed by the replacement of the marker gene with the rearranged VJ DNA fragment. The modified BAC clone is amplified and purified using standard procedures.

EXAMPLE 8

Transgenic Rabbits Expressing the Humanized Immunoglobulin Light and/or Heavy Chain Transgene Transgenic rabbits are generated as described by Fan et al. (*Pathol. Int.* 49: 583–594, 1999). Briefly, female rabbits are superovulated using standard methods and mated with male rabbits. Pronuclear-stage zygotes are collected from oviduct and placed in an appropriate medium such as Dulbecco's phosphate buffered saline supplemented with 20% fetal bovine serum. The exogenous DNA (e.g., the humanized BAC clone from Example 4 and/or 5 which has been linearized prior to injection) is microinjected into the male pronucleus with the aid of a pair of manipulators. Morphological surviving zygotes are transferred to the oviducts of pseudopregnant rabbits. Pseudopregnancy is induced by the injection of human chorionic gonadotrophin (hCG). Between about 0.1–1% of the injected zygotes develop into live transgenic rabbits. Integration of the transgene in the genome is confirmed by Southern blots analysis using a probe specific for the transgene.

cDNA is prepared using RNA isolated from B cells (in blood, spleen and/or lymph nodes) of a transgenic rabbit. Primers specific for the human transgene (human CH gene segment or the synthetic humanized VH gene segment) are used to generate amplified products from cDNA. The observation of amplified products indicates that the transgene is rearranged in the transgenic animal and the rearranged transgene is transcribed in the animal. Amplified products are sequenced and the presence of donor sequences from upstream V genes indicates that the transgene introduced into the germline of the animal undergoes gene conversion.

The presence of antibodies containing human IgG and/or human kappa light chain antigenic determinants in the serum of transgenic founder rabbits is determined using an ELISA assay.

EXAMPLE 9

Production of Humanized Antibodies from Transgenic Rabbits with the Genetic Background of the Alicia and/or Basilea Rabbit Strain The Alicia strain lacks the VH1 gene segment and therefore has an impaired Ig heavy chain expression. Transgenic founder rabbits capable of expressing humanized heavy chain molecules in the genetic background of the Alicia rabbit strain are generated, e.g., by using fetal fibroblasts established from Alicia rabbits in Examples 4–5 above, or by using zygotes from female Alicia rabbits mated with male Alicia rabbits in Example 8 above. Transgenic animals are also obtained which are homozygous for the Alicia Ig phenotype and are also homozygous for a humanized heavy chain transgene. Serum is tested in ELISA for the presence of humanized heavy chain (e.g., a human heavy chain constant region). The concentration of antibodies with humanized Ig heavy chains in these homozygous Alicia animals is substantially higher, e.g., about 10 to 100 fold higher, than that produced from a transgene integrated in the genome of wild type (non-Alicia) rabbits.

The Basilea strain does not express κ1 light chain and in its place exclusively express the κ2 and λ light chains. Transgenic founder rabbits capable of expressing humanized light chain molecules in the genetic background of the Basilea rabbit strain are generated, e.g., by using fetal fibroblasts established from Basilea rabbits in Examples 4–5 above, or by using zygotes from female Basilea rabbits mated with male Basilea rabbits in Example 8 above. Transgenic animals are obtained which are homozygous for the Basilea light chain phenotype, and are also homozygous for a humanized light chain transgene. Serum is tested in ELISA for the presence of the humanized light chain. The concentration of the humanized light chain in the homozygous Basilea animals is substantially higher, about 10–100 fold higher, than the concentration of a humanized light chain in a transgenic rabbit with the wild type (non-Basilea) genetic background. Transgenic founder rabbits are mated with each other to generate transgenic rabbits with the following traits: (1) having at least one humanized light chain transgene, (2) having at least one humanized heavy chain transgene, (3) homozygous for the Alicia heavy chain locus, and (4) homozygous for the Basilea light chain locus.

EXAMPLE 10

Construction of a DNA Fragment Containing a Modified Chicken Light Chain Locus Having a Human Clambda2 Gene Segment and a VJ Gene Segment Encoding a Human VL Domain A genomic BAC library derived from a jungle fowl chicken was screened with radiolabeled probes specific for chicken light chain Clambda and chicken Vpsi25 (the V gene segment at the very 5' end of the light chain locus). A BAC clone containing the entire lambda light chain locus was identified. The chicken Cλ gene on this BAC clone is replaced with the human Cλ2 gene by homologous recombination in *E. coli* using the pET system (Zhang et al., *Nat. Biotechnol.* 18(12):1314–7, 2000) as follows.

A first DNA fragment containing a kanamycin selection cassette was generated by PCR using primers specific for Tn5 gene. The 5' primer (5' catacacagccatacatacgcgtgtggc-cgctctgcctctctcttgcaggTATGGACAGCAAGCGAACCG 3', SEQ ID NO: 55) was designed to include 50 bp at the 5' end (lower case), derived from the 5' flanking region of the chicken light chain Cλ gene. The 3' primer (5' atcagggtgac-ccctacgttacactcctgtcaccaag-gagtgggagggacTCAGAAGAACTCGTCAAGA AG3', SEQ ID NO: 56) was designed to include about 50 bp at the end (lower case), derived from the 3' flanking region of the chicken light chain Cλ gene.

A second DNA fragment (SEQ ID NO: 57) was synthesized using overlapping oligonucleotides wherein the DNA fragment contains from 5' to 3', a sequence derived from the 5' flanking region of the chicken light chain Clambda gene, the human Clambda2 gene, and a sequence derived from the 3' flanking region of the chicken Clambda gene (FIG. 12).

*E. coli* cells of the chicken light chain BAC clone were transformed with a recombination plasmid expressing the recE and recT functions under an inducible promotor. Cells transformed with the recombination plasmid were then transformed with the first DNA fragment above and selected afterwards in media containing kanamycin. Clones resistant to kanamycin were identified, and the replacement of the chicken Cλ segment by the kanamycin selection cassette via homologous recombination was confirmed by restriction enzyme digest.

In the second homologous recombination step, cells positive for the kanamycin selection cassette were transformed with the second DNA fragment above. Transformed cells were screened for the loss of kanamycin resistance as indicative of the replacement of the kanamycin selection cassette by the human Cλ2 gene. The exchange was confirmed by restriction enzyme digest and/or sequence analysis.

The ET cloning procedure is summarized in FIG. 13.

The BAC clone containing the chicken light chain locus and the inserted human Clambda2 gene segment was further modified by inserting a rearranged VJ DNA fragment. The rearranged VJ DNA fragment encodes a human immunoglobulin variable domain polypeptide described by Kametani et al. (*J. Biochem.* 93 (2), 421–429, 1983) as IG LAMBDA CHAIN V-I REGION NIG-64 (P01702) (FIG. 14). The nucleotide sequence of the rearranged VJ fragment was so designed as to maximize the sequence homology at the nucleotide level to the chicken Vlambda1 sequence published by McCormack et al. (*Cell* 56, 785–791, 1989). This rearranged VJ DNA sequence is more than 80% identical with known chicken light chain V genes. The rearranged VJ DNA fragment was linked to a 5' flanking sequence and a 3' flanking sequence, resulting in the DNA fragment of SEQ ID NO: 58 (FIG. 14). The 5' flanking sequence was derived from 5' of chicken Vlambda1, and the 3'flanking sequence was derived from 3' of chicken J. The DNA fragment of SEQ ID NO: 58 was subsequently inserted into the chicken light chain locus in *E. coli* using the pET system as shown in FIG. 15. The insertion was performed in such a way that the region on the chicken light chain locus from the 5' end of the chicken Vlambda1 gene segment to the 3' end of the chicken J region was replaced with the rearranged, synthetic VJ DNA fragment. Again, this insertion was accomplished by the replacement of the chicken V-J region with a marker gene, followed by the replacement of the marker gene with the rearranged VJ DNA fragment. The modified region of the chicken light chain locus is shown in FIG. 15. The modified BAC clone was amplified and purified using standard procedures.

EXAMPLE 11

Construction of a DNA Fragment Containing a Portion of a Chicken Heavy Chain Locus with a Human Cγ1 Gene Segment and a VH Gene Segment Encoding a Human VH Domain Polypeptide Sequence A jungle fowl chicken genomic BAC library was generated by standard procedures and screened with probes specific for chicken Cγ. A BAC clone containing chicken heavy chain gene segments is identified. The upstream and downstream regions (i.e., the 5' and 3' flanking regions) of the heavy chain Cγ gene are sequenced. The chicken Cγ gene on this BAC clone is replaced with the human Cγ1 gene by homologous recombination in *E. coli* using the pET system as follows.

A first DNA fragment containing a kanamycin selection cassette is generated by PCR using primers specific for Tn5 gene. The 5' and 3' primers are designed to include about 50 bp at the end, derived from the 5' and 3' flanking regions of the chicken heavy chain Cγ gene.

A second DNA fragment is generated by PCR using overlapping oligonucleotides wherein this second DNA fragment contains from 5' to 3', a sequence of about 50 bp derived from the 5' flanking region of the chicken Cγ gene, the human Cγ1 gene, and a sequence of about 50 bp derived from the 3' flanking region of the chicken Cγ gene.

*E. coli* cells of the chicken CY BAC clone are transformed with a recombination plasmid expressing the recE and recT functions under an inducible promotor. Cells transformed with the recombination plasmid are further transformed with the first DNA fragment and selected in media containing kanamycin. Clones resistant to kanamycin are identified, and the replacement of the chicken CY segment by the kanamycin selection cassette via homologous recombination is confirmed by restriction enyme digest.

In the second homologous recombination step, cells positive for the kanamycin selection cassette are now transformed with the second DNA fragment described above. Transformed cells are screened for loss of kanamycin resistance as indicative of the replacement of the kanamycin selection cassette by the human Cγ1 gene. The exchange is confirmed by restriction enzyme digest and/or sequence analysis.

The BAC clone containing the inserted human Cγ1 gene is further modified by replacing the 3'proximal VH1 segment (i.e., the 3'proximal VH1 gene in the V region) with a synthetic VH gene segment. This synthetic VH gene segment is designed based on the published sequence of a chicken VH1 gene (Arakawa et al., EMBO J 15(10): 2540–2546, 1996). The synthetic gene segment is more than 80% identical to chicken VH gene segments and encodes an amino acid sequence that is identical to the amino acid sequence of a human immunoglobulin heavy chain variable domain polypeptide described by Matthyssens and Rabbitss (in Steinberg C M and Lefkovits I, (eds). *The Immune System:* 132–138, S. Karger, NY 1981). This synthetic VH segment including 5' and 3' flanking sequences is synthesized by PCR using overlapping oligonucleotides. The 5' and the 3' flanking sequences are derived from the upstream and downstream regions of chicken VH1 gene. This synthetic VH segment is used to replace the chicken VH1 gene on the BAC clone by homologous recombination using the pET system. The modified BAC clone is amplified and purified using standard procedures.

EXAMPLE 12

Transgenic Chicken Expressing the Humanized Immunoglobulin Light and/or Heavy Chain Transgenes The production of transgenic chicken is carried out using techniques as described by Etches et al., *Methods in Molecular Biology* 62: 433–450; Pain et al., *Cells Tissues Organs* 1999; 165(3–4): 212–9; Sang, H., "Transgenic chickens—methods and potential applications", *Trends Biotechnol* 12:415 (1994); and in WO 200075300, "Introducing a nucleic acid into an avian genome, useful for transfecting avian blastodermal cells for producing transgenic avian animals with the desired genes, by directly introducing the nucleic acid into the germinal disc of the egg".

Briefly, the modified BAC clones are linearized and mixed with a transfection reagent to promote uptake of DNA into cells. The formulations are injected into a multicell stage chicken embryo in close proximity to the germinal disc. The window in the egg shell is closed and the eggs are incubated. After hatching chimeric chickens are identified by PCR and Southern blot analysis using transgene specific sequences. Integration of the transgene in the genome is confirmed by Southern blots analysis using a probe specific for the transgene. Heavy and light chain transgenic animals are bred with each other to generate transgenic chickens expressing antibodies having humanized heavy and light chains.

cDNA is prepared using RNA isolated from B cells (in blood, spleen and/or lymph nodes) from transgenic chickens. Primers specific for the human transgene (e.g., human CH gene segments and/or the synthetic humanized VH gene segments) are used to generate amplified products from cDNA. The observation of amplified products indicates that the transgene is rearranged in the transgenic animal and the rearranged transgene is transcribed in the animal. Amplified products are sequenced and the presence of donor sequences from upstream V genes indicates that the transgene introduced into the germline of the animal undergoes gene conversion.

The presence of antibodies containing human IgG and/or human kappa light chain antigenic determinants in the serum of transgenic chickens is determined using an ELISA assay.

EXAMPLE 13

Production of Functional Humanized Antibodies in Transgenic Chicken with the Agammaglobulinemic Phenotype Transgenic chickens with the following traits are produced: (1) having at least one humanized light chain transgene, (2) having at least one humanized heavy chain transgene, and (3) homozygous for the agammaglobulinemic phenotype. These animals produce antibodies into the blood and eggs, and antibodies can be purified from either source. In general, antibody concentrations in the eggs are about 5% to 50% of antibodies concentration in the blood. Animals that contain humanized antibodies at high levels in eggs can be selected and bred to produce offspring. Alternatively, transgenic animals can be generated that specifically secrete humanized antibodies into their eggs.

EXAMPLE 14

Generation of Transgenic Chickens Expressing Humanized Immunoglobulin

Chicken embryonic stem cells are isolated and cultured as described by Pain et al. (*Development* 122, 2339–2348; 1996). Chicken embryos are obtained from eggs immediately after they are laid. The entire blastoderm is removed by gentle aspiration, embryos are slowly dissociated mechanically and cells are seeded in ESA complete medium on inactivated STO feeder cells. ESA medium is composed of MEM medium containing 10% FCS, 2% chicken serum, 1% bovine serum albumin, 10 ng/ml ovalbumin, 1 mM sodium pyruvate, 1% non-essential amino acids, 1 µM of each nucleotide adenosine, guanosine, cytidine, uridine, thymidine, 0.16 mM β-mercaptoethanol, ESA complete medium is supplemented with 10 ng/ml bFGF, 20 ng/ml h-IGF-1, 1% vol/vol avian-SCF and 1% vol/vol h-LIF, 1% vol/vol h-IL-11. Cell cultures are incubated wt 37° C. in 7.5 $CO_2$ and 90% humidity. After 48 hours fresh blastodermal cells are added to the culture in half of the original volume of ESA complete medium. After an additional incubation for three days, the culture medium is partially (50%) replaced with fresh ESA complete medium, and totally every day thereafter. For cell harvesting, cultures are washed with PBS and incubated in a pronase solution (0.025% w/v). Dissociated cells are transfected with various linearized transgenic constructs containing a humanized Ig locus. Transfected cells are incubated with STO feeder cells (as described above) in the presence of selective antibiotics. Cells are transferred onto fresh feeder cells twice per week. Antibiotic resistant cells are isolated and the integration of a humanized Ig gene fragments at a random site or at the corresponding chicken immunoglobulin gene loci is confirmed by PCR.

Subsequently, genetically modified cells are injected into recipient embryos. As recipient embryos, freshly laid eggs are irradiated (6Gy—Cobalt source). Between 100 to 200 genetically modified cells are injected into the subgerminal cavity using a micropipet. The window in the egg shell is closed and the eggs are incubated. Somatic chimerism of hatched chickens is evaluated by PCR. Germ-line chimerism is assessed by mating of somatic chimeras.

EXAMPLE 15

Immunization of Transgenic Animals

Genetically engineered chickens are immunized intramuscularly with purified Hepatitis B surface antigen (HBsAg) (5 µg in incomplete Freund's adjuvant) on day 0, 14 and day 28. On day 35 animals are bled and serum is prepared. ELISA plates (NUNC, Denmark) are coated with 1 µg/ml HBsAg in PBS for 1 hour at room temperature. Subsequently, available binding sites are blocked by incubation with 1% non-fat dry milk (NFM) in PBS (300 µl/well). Chicken serum is diluted in PBS/1% NFM and added to the coated wells. After an incubation of 1 hour, the plates are washed 3 times with PBS/0.05% Tween 20 and bound Ig is detected using goat anti-human Ig conjugated with horseradish peroxidase. Conjugated goat antibody is detected using o-phenylenediamine dihydrochloride (Sigma) at 1 mg/ml. The colorimetric reaction is stopped by addition of 1 M HCl solution and the absorbance is measured at 490 nm. As a control, serum from non-immunized chicken is used. Serum from non-immunized chickens does not react with HBsAg. At a dilution of 1:250 the optical density measured in uncoated and HBsAg coated wells is below 0.2. In contrast, serum from immunized chickens contains humanized antibodies reactive with HBsAg. At a serum dilution of 1:250 the measured optical density is 2.3. Upon further dilution of the serum the measured optical density declines to 0.1 (at a dilution of 25600). No antibodies reactive with a goat anti-chicken IgG-HRP conjugate can be detected. This demonstrates that the genetically engineered chickens produce humanized anti-HBsAg antibodies following immunization.

Genetically engineered rabbits are immunized intramuscularly with purified Hepatitis B surface antigen (HBsAg) (10 µg in incomplete Freund's adjuvant) on day 0 and day 14. On day 28 animals are bled from the ear and serum is prepared. ELISA plates (NUNC, Denmark) are coated with 1 µg/ml HBsAg in PBS for 1 hour at room temperature. Subsequently, available binding sites are blocked by incubation with 1% non-fat dry milk (NFM) in PBS (300 µl/well). Rabbit serum is diluted in PBS/1% NFM and added to the coated wells. After an incubation of 1 hour, the plates are washed 3 times with PBS/0.05% Tween 20 and bound Ig is detected using goat anti-human Ig conjugated with horseradish peroxidase. Conjugated goat antibody is detected using o-phenylenediamine dihydrochloride (Sigma) at 1 mg/ml. The colorimetric reaction is stopped by addition of 1 M HCl solution and the absorbance is measured at 490 nm. As a control serum from non-immunized rabbits is used. Serum from non-immunized rabbits does not react with HBsAg. At a dilution of 1:100 the optical density measured in uncoated and HBsAg coated wells is below 0.4. In contrast, serum from immunized rabbits contains partially human antibodies reactive with HBsAg. At a serum dilution of 1:100 the measured optical density is 2.8. Upon further dilution of the serum the measured optical density declines to 0.2 (at a dilution of 25600). No antibodies reactive with a goat anti-rabbit IgG-HRP conjugate can be detected. This demonstrates that the genetically engineered rabbits produce humanized anti-HBsAg antibodies following immunization.

EXAMPLE 16

Complement Mediated Cytotoxicity of Virus Infected Cell Line Using Humanized Antibodies A human liver carcinoma cell line expressing HBsAg is labeled with 0.1 mCi $^{51}$Cr in 100 ul PBS for 1 hr at 37° C. Two thousand $^{51}$Cr-lableled cells are incubated with serum from genetically engineered rabbits or chickens expressing anti-HbsAg humanized immunoglobulins. After two hours at 37° C. the release of $^{51}$Cr into the supernatant is determined by measuring radioactivity using a scintillation counter. For the determination of maximum release, 1% Triton X100 is added. The degree of cell lysis is calculated as follows: % Lysis=CPM experimental±CPM#spontaneous/CPM# total±CPM spontaneous. Incubation of labeled cells with serum (diluted 1:30) from non-immunized rabbits does not result in cell lysis (<10%). However, incubation of cells with serum from immunized rabbits causes 80% cell lysis. Inactivation of complement in the serum by heat treatment (56° C. for 30 minutes) renders the serum from immunized rabbits inactive. These results demonstrate that humanized antibodies produced by genetically engineered rabbits bind to HBsAg-positive cells and cause complement dependent lysis.

EXAMPLE 17

Immunization of Transgenic Animals Against *Staphylococcus aureus*

Genetically engineered chickens are immunized intramuscularly with a recombinant fragment of the *Staphylococcus aureus* collagen adhesin protein (100 µg in incomplete Freund's adjuvant) on day 0, 14 and day 28. On day 35 animals are bled and serum is prepared. ELISA plates (NUNC, Denmark) are coated with 2 µg/ml collagen adhesin protein in PBS for 1 hour at room temperature. Subsequently, available binding sites are blocked by incubation with 1% non-fat dry milk (NFM) in PBS (300 µl/well). Chicken serum is diluted in PBS/1% NFM and added to the coated wells. After an incubation of 1 hour, the plates are washed 3 times with PBS/0.05% Tween 20 and bound Ig is detected using goat anti-human Ig conjugated with horseradish peroxidase. Conjugated goat antibody is detected using o-phenylenediamine dihydrochloride (Sigma) at 1 mg/ml. The colorimetric reaction is stopped by addition of 1 M HCl solution and the absorbance is measured at 490 nm. As a control, serum from non-immunized chicken is used. Serum from non-immunized chickens does not react with collagen adhesin protein. At a dilution of 1:250 the optical density measured in uncoated and collagen adhesin protein coated wells is below 0.2. In contrast, serum from immunized chickens contains humanized antibodies reactive with collagen adhesin. At a serum dilution of 1:250 the measured optical density is 2.3. Upon further dilution of the serum the measured optical density declines to 0.1 (at a dilution of 25600). No antibodies reactive with a goat anti-chicken IgG-HRP conjugate can be detected. This demonstrates that the genetically engineered chickens produce humanized anti-*Staph. aureus* collagen adhesin antibodies following immunization.

Genetically engineered rabbits are immunized intramuscularly with recombinant fragment of the *Staphylococcus aureus* collagen adhesin protein (100 µg in incomplete Freund's adjuvant) on day 0 and day 14. On day 35 animals are bled and serum is prepared. ELISA plates (NUNC, Denmark) are coated with 2 μg/ml collagen adhesin protein in PBS for 1 hour at room temperature. Subsequently, available binding sites are blocked by incubation with 1% non-fat dry milk (NFM) in PBS (300 μl/well). Rabbit serum is diluted in PBS/1% NFM and added to the coated wells. After an incubation of 1 hour, the plates are washed 3 times with PBS/0.05% Tween 20 and bound Ig is detected using goat anti-human Ig conjugated with horseradish peroxidase. Conjugated goat antibody is detected using o-phenylenediamine dihydrochloride (Sigma) at 1 mg/ml. The calorimetric reaction is stopped by addition of 1 M HCl solution and the absorbance is measured at 490 nm. As a control, serum from non-immunized rabbit is used. Serum from non-immunized rabbits does not react with collagen adhesin protein. At a dilution of 1:250 the optical density measured in uncoated and collagen adhesin protein coated wells is below 0.2. In contrast, serum from immunized rabbits contains humanized antibodies reactive with collagen adhesin. At a serum dilution of 1:250 the measured optical density is 2.3. Upon further dilution of the serum the measured optical density declines to 0.1 (at a dilution of 25600). No antibodies reactive with a goat anti-rabbit IgG-HRP conjugate can be detected. This demonstrates that the genetically engineered rabbits produce humanized anti-*Staph. aureus* collagen adhesin antibodies following immunization.

EXAMPLE 18

Protection Against *Staphylococcus aureus* Infection in a Mouse Model

Naive mice are passively immunized i.p. on day −1 with 16 mg of the immunoglobulin fraction containing antibodies specific for the *S. aureus* collagen adhesin protein (from Example 17) or with the immunoglobulin fraction from non-immunized animals. On day 0, the mice are challenged i.v. with 4×10⁷ CFU *S. aureus* per mouse and mortality is monitored over the next 7 days. Mortality rate in the control groups is 80% and 10% in the group treated with the immunoglobulin fraction containing antibodies specific for the *S. aureus* collagen adhesin protein. The data indicate that anticollagen adhesin antibodies can protect mice against lethal *S. aureus* challenge.

EXAMPLE 19

Antigen-Specific Hybridomas Made from Transgenic Animals

Transgenic animals are immunized with an antigen (e.g., KLH, human red blood cells or sheep red blood cells). Spleen cells are removed at various times after immunization and fused with myeloma cell lines derived from rabbit and chicken, respectively. After fusion cells are plated into 96 well plates and supernatants are tested for the presence of humanized antibodies. To demonstrate that the antibodies contain human immunoglobulin sequences, hybridomas are stained with fluorescent-labeled antibodies reactive with human heavy and light chain immunoglobulins. Limiting dilution is conducted to purify hybridomas to monoclonality.

EXAMPLE 20

Evaluation of Immunogenicity

Serum samples are collected from five cynomologous monkeys on day 0. Subsequently, a purified partially human polyclonal antibody preparation (5 mg/kg) is administered into five cynomologous monkeys by intravenous administration. The administration is repeated six times in bi-weekly intervals. Monkeys are monitored closely for any side-effects (e.g., anaphylactic shock, reflected by an elevated body temperature). After seven months serum is collected from blood samples. Affinity resins containing purified human IgG or partially human IgG are produced by standard procedure using CNBr-activated Sepharose. Monkey serum samples (3 ml) are added to the IgG-affinity resin (4 ml) containing 10 mg human or partially human IgG. Subsequently, the columns are washed with PBS. Bound monkey immunoglobulin is eluted from the column with 0.1M glcyin/HCl pH2.5 and dialyzed 2 times against PBS. The protein content of the eluted fractions is determined using the BCA assay using human IgG as a standard. The total amounts of protein in these fractions demonstrate that therapy with partially human IgG does not lead to a significant antibody response in the treated animals.

EXAMPLE 21

Treating Animals Using Humanized Antibodies

Humanized polyclonal immunoglobulins are purified from the serum of genetically engineered rabbits, or from egg yolk of genetically engineered chickens, by ammonium sulfate precipitation and ion exchange chromatography. SCID-mice are injected with one million human liver carcinoma cells expressing HBsAg. Subsequently, 25 μg immunoglobulin is injected peritoneally once per day. Animals treated with antibodies isolated from non-immunized rabbit serum die after about 60 days. This is similar to untreated recipients of liver carcinoma cells. In contrast, mice treated with antibodies isolated from immunized rabbit serum survive for more than 150 days. This demonstrates that human antibodies produced in genetically engineered rabbits are capable of eliminating human carcinoma cells from SCID-mice.

What is claimed is:

1. A transgenic vector comprising a humanized Immunoglobulin (Ig) locus, wherein
   (a) said humanized Ig locus comprises multiple Ig gene segments, including multiple variable (V) gene segments, multiple J gene segments, and one or more constant region gene segments,
   (b) at least one of said gene segments is a functional V gene segment encoding a human V region amino acid sequence,
   (c) said V gene segments are separated only by non-coding, non-human sequences derived from a non-human animal that generates antibody diversity primarily through gene conversion and/or hypermutation,
   (d) at least one of said functional V gene segments encoding a human V region amino acid sequence is placed downstream of the other V gene segments, and
   (e) said Ig gene segments are juxtaposed in an unrearranged, partially rearranged or fully rearranged configuration, and
   wherein, as a result of structural features (a)–(e), said humanized Ig locus is capable of undergoing gene conversion and producing a repertoire of humanized immunoglobulins with V region amino acid sequences encoded by segments of more than one V region gene, in said non-human animal.

2. The transgenic vector of claim 1, wherein said non-human animal is rabbit, pig, chicken, sheep or cow.

3. The transgenic vector of claim 1, wherein said humanized Ig locus is a heavy chain locus and comprises at least two human V gene segments, at least one D gene segment, at least two J gene segments and one or more constant region segments.

4. The transgenic vector of claim 1, wherein said humanized Ig locus is a light chain locus and comprises at least two V gene segments, at least two J gene segments, and one or more constant region gene segments.

5. The transgenic vector of claim 3, wherein the non-human animal is a rabbit, and at least one of said non-coding sequences comprises the sequence of SEQ ID NO: 10.

6. The transgenic vector of claim 3, wherein said constant region gene segment is a human heavy chain constant region gene segment.

7. The transgenic vector of claim 6, wherein said human heavy chain constant region gene segment is a Cγ.

8. The transgenic vector of claim 6, comprising about 10–100 V gene segments and at least two human V gene segment, wherein said human V gene segment is placed downstream to said 10–100 V gene segments.

9. The transgenic vector of claim 8, wherein said V gene segments are selected from V gene segments at the 3' V-region of said non-human animal and human V gene segments.

10. The transgenic vector of claim 4, wherein said constant region gene segment is a human light chain constant region gene segment.

11. The transgenic vector of claim 10, wherein said human light chain constant region gene segment is Cλ or Cκ.

12. The transgenic vector of claim 10, comprising about 10–100 V gene segments and at least two human V gene segment, wherein said human V gene segment is placed downstream to said 10–100 V gene segments.

13. The transgenic vector of claim 12, wherein said V gene segments are selected from V gene segments at the 3' V-region of said non-human animal and human V gene segments.

14. The transgenic vector of claim 10, wherein said human V gene segment is placed immediately 5' to a J gene segment in a rearranged configuration.

15. A method of making a transgenic vector comprising a humanized Immunoglobulin (Ig) locus capable of producing a functional repertoire of humanized antibodies in a non-human animal generating antibody diversity primarily through gene conversion and/or hypermutation, comprising:
   (i) obtaining a DNA fragment comprising an Ig locus or a portion therefor from said non-human animal, which comprises at least two V gene segments, at least one J gene segment and at least one constant region gene segment, and non-coding sequences; and
   (ii) integrating by homologous recombination at least one functional human V gene segment encoding a human V region amino acid sequence, into said DNA fragment of step (i) to produce a humanized Ig locus,
   wherein the V gene segments present are separated only by non-coding, non-human sequences derived from said non-human animal that generates antibody diversity primarily through gene conversion and/or hypermutation, and at least one of the functional V gene segments encoding a human V region amino acid sequence is placed downstream of the other V gene segments, and
   wherein said Ig gene segments are juxtaposed in an unrearranged, partially rearranged or fully rearranged configuration, as to permit gene rearrangement and gene conversion of said humanized Ig locus and the production of a functional repertoire of humanized antibodies with V region amino acid sequences encoded by more than one V region gene segment, in said non-human animal.

16. The method of claim 15, wherein the integration of said human Ig gene segment by homologous recombination, replaces an Ig gene segment in said Ig locus or said portion thereof from said non-human animal.

17. The method of claim 16, wherein the homologous recombination is achieved in a bacterial cell, a yeast cell, or a non-human animal cell.

18. The method of claim 16, wherein the human Ig gene segment is provided on a recombination vector, and is linked to a 5' nucleotide sequence and a 3' nucleotide sequence which are homologous to the 5' and 3' flanking sequences of said Ig gene segment from the non-human animal.

* * * * *

SEQUENCE LISTING

<160> NUMBER OF SEQ ID NOS: 58

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 1
cgcaagcttc ctacacgtgt gtggtgatg                                29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 2
cgcaagctta agatggwgat ggtsgtcca                                29

<210> SEQ ID NO 3
<211> LENGTH: 1714
<212> TYPE: DNA
<213> ORGANISM: cow

<400> SEQUENCE: 3

```
cctacacgtg tgtggtgatg cacgaaactt tacggaatca ctacaaagag aagtccacct      60
cgaggtctcc gggtaaatga gcctcgcgcc gctgatctag tggacgttcc ctcatccacc     120
caccctccc cccacccgg gctccaggtc cagccagggc gccctagccc ctccctgtgt       180
gcattcctcc tgggccgccg tgaataaagc acccaggccg ccctgggacc ctgcaacgct     240
gtgctggttc tttccgaggc agagccctgg tggccgccag gcctgcgggg gtgggctgag     300
ccgactctgg gccactttgt tcagcatctg tggggagct gacccactc cgggccagac      360
acacagtgag tgggtccagc aggccacctg ggggctgccc aaggccacag aggggcttgg    420
ccagaggcac agctccacgg tcccctccag ccaccacctg ctgggccggc ctctggacag    480
gaaccgggga agcccccgag accctcaggg attgaggccc aatgcttccc gcctctgctc    540
cagcccacgc tgtggggcag gccacatcc ttgtccccag gccccgtgcc ttgggtgtcc     600
agagtccttg tgtccactct gggcctgcct ggagccacgc atggccaggg ggtggccctg    660
cttcaccctc aggctcccaa ggtcaggcct cgccctccct cggccaggag gctctgcccg    720
gctctccctg cccagggcca ggcctgtgcg cccatgggga ggtcatccct gtgcctgaaa    780
ggggtccagg ccgagagccc tgaatgtcca gggcagggac ctagctgctc cctgtggaca    840
cggagcccag agccacagac aacaagcccc agccccgcac gcacacgaga cagcccgcac    900
ccagcctcct ccacacgcac tcaggtgtac atgcgcacat gagcacactt caccccgtca    960
cacccacaca cctacacaca ctcaggtctc gcactcgggg acccatgggg tgaccccacg   1020
ggcccagacc agagctgggt cttgtgagcc ctccctgtgg acaccagctg gccccaccc    1080
tccagcgccc atgggctgct cagcggccct ttcccacact gaccacactg accaggtcag   1140
acatccgttc cttgcctccc ctgggacacc cacgcccctc cctagcaggc tgagatcccc   1200
cctcagcccc tcgtcctggc agcctcaccc ctcgggcaca gcacccctca ggcccggtgc   1260
tgtcagccct ccctccccgg gggcagggcc caggaacgtg cgctctgctg accctcccag   1320
ctccaggcct ggccccagg gcagaggagg ccaggaactg agcctctgtc ctgtggggag    1380
gtagggtcag ggtcccagct cagggcacag ctcaggatgg gagcaggacc cacaggcca    1440
ggcccagata gcagcaggg ctggaggggt tgggctggg gctggcccc agagactgac      1500
ctcaggtgac ccctgcctgg cccatgggga gatcacgcca ccttcccccc acccagaggg   1560
agccctgccc tacccagtg accctgccca gccctccgtg ggcagacaca gcactgacca   1620
cccctccctg tgcagacttg ctgctggagg aggagatctg tgcggacgac ctggatgggg   1680
```

```
agctggacgg gctctggacc accatctcca tctt                              1714

<210> SEQ ID NO 4
<211> LENGTH: 1704
<212> TYPE: DNA
<213> ORGANISM: cow

<400> SEQUENCE: 4
cctacacgtg tgtggtgatg cacgaggccc tgcacaatca ctacacgcag aagtccacct    60
ctaagtctgc gggtaaatga gcctcacgtc cctgcaccag caagccctca cccagcccac   120
cctccccggg ctccaagtcc agccaggacg ccctagcccc tccctgtgtg cattcctcct   180
gggccgccgt gaataaagca cccaggccac cctgggaccc tgcaacgctg tgctggttct   240
ttccgaggca gagccctggt ggccgccagg cctgcagggg tgggctgagc cgactctggg   300
ccactttgtt cagcatctgt gggggagctg accccgctcc gggccagaca cacagtgagt   360
gggtccagca ggccacctgg gggctgcccg aggccacgga ggggcttggc cagaggcgta   420
cctccacggc cccctccagc caccacctgc tgggccggcc tctggacagg aaccggggaa   480
gcccccgaga ccctcaggga ttgaggccca atgcttcccg cctctgctcc agcccacgct   540
gtggggcagg gccacatcct tgtccccagg cccctgtccc tgggtgccca gagtccttgt   600
gtccactctg ggcctgcctg gagccacgcg tggccggggg atggccctgc tccaccctca   660
ggctcccaag gtcaggcctc gccctcccct cagcaggagg ctctgcccgg ctctccctgc   720
ccagggccag gcctgtgcgc ccatgggggag gtcatccctg tgcctgaaag gctccaggc   780 cgggagccct gaatgtccag ggcagggacc tagctgctcc ctgcagacac ggagcccaga   840
gccacagaca acaagcccca gccccgcacg cacacaagac agcccgcacc cagcctcctc   900
cacacgcact caggtgtgca tccgcacatg agcacacttc acccgtcac acccacacgc    960 ctacacacac tcaggtctcg cactcgggga cccatgggt gaccccacag gcccagaccc   1020
agagctgggt cttgtgagcc ctccctgtgg acaccagctg gtccccaccc tccagcgccc   1080
atgggctgct cagtggccct ttcccacact gaccacactg accaggtcag acatccgttc   1140
cttgcctccc ctgggcacc cacgcccctc cctagcaggc tgagatcccc cctcagcccc   1200
tcgtcctggc accctcaccc ctcaggcaca gggacacagc ccggcgctgt ctgccctccc   1260
tccctggggg cagggcccag gctcacatgc tctgctgacc ctcccggctc caggcctggc   1320
ccccagggca gaggaggcca ggaactgagc ctctgtcctg gggggaggtg gggtcagggc   1380
cccagctcag ggcacagctc aggatgggaa caggacacca caggccaggc ccagacagtg   1440
gccagggctg gaggggtggg gtctgggct ggggcccaga gactgacctc aggtgatccc   1500
tgcccagccc atgggggat cctgccacct tcccccacc cagagggagc cctgccccga   1560
ggccctgatg atgccaccca gccccgtg ggcagacaca gcactgacca cccctccctg   1620
tgcagacctg ctgctggagg aggagatctg tgcggacgcc caggacgggg agctggacgg   1680
gctctggacg accatcacca tctt                                         1704

<210> SEQ ID NO 5
<211> LENGTH: 1704
<212> TYPE: DNA
<213> ORGANISM: cow

<400> SEQUENCE: 5
cctacacgtg tgtggtgatg cacgaggccc tgcacaatca ctacacgcag aagtccacct    60
```

```
ctaagtctgc gggtaaatga gcctcacgtc cctgcaccag caagccctca cccagcccac    120
cctccccggg ctccaggtcc agccaggacg ccctagcccc tccctgtgtg cattcctcct    180
gggccgccgt gaataaagca cccaggccgc cctgggaccc tgcaacgctg tgctggttct    240
ttccgaggca gagccctggt ggccgccagg cctgcggggg tgggctgagc cgactctggg    300
ccactttgtt cagcatctgt gggggagctg accccactcc gggccagaca cacagtgagt    360
gggtccagca ggccacctgg gggctgccca aggccacaga ggggcttggc cagaggcaca    420
gctccacggt ccctccagc caccacctgc tgggccggcc tctggacagg aaccggggaa     480
gcccccgaga ccctcaggga ttgaggccca atgcttcccg cctctgctcc agcccacgct    540
gtggggcagg gccacatcct tgtccccagg cccctgtcct tgggtgtcca gagtccttgt    600
gtccactctg ggcctgcctg gagccacgca tggccagggg gtggccctgc ttcaccctca    660
ggctcccaag gtcaggcctc gccctccctc ggccaggagg ctctgcccgg ctctccctgc    720
ccagggccag gcctgtgcgc ccatggggag gtcatccctg tgcctgaaag gggtccaggc    780
cgagagccct gaatgtccag ggcagggacc tagctgctcc ctgtggacac ggagcccaga    840
gccacagaca acaagcccca gccccgcacg cacgcgagac agcccacacc ccgcctcctc    900
cacacgcact caggtgtgca tccgcacatg agcacacttc accccatcac acccacacgc    960
ctacacacac tcaggtctcg cactcgggga cccatgggt gacccacag gcccagaccc     1020
agagctgggt cttgtgagcc ctccctgtgg acaccagctg gtccccaccc tccagcgccc    1080
gtgggctgct cagcggtcct ttcccacact gaccacactg accaggtcag acatccgttc    1140
cttgcctccc ctggggcacc catgcccctc cctagcaggc tgagatcccc cctcagcccc    1200
tcgtcctggc accctcaccc ctcaggcaca gggacacagc ccggtgctgt ctgccctccc    1260
tccctggggg cagggcccag gctcacatgc tctgctgacc ctcccagctc caggcctggc    1320
ccccagggca gaggaggcca ggaactgagc ctctgtcctg gggggaggtg gggtcagggc    1380
cccagctcag ggcacagctc aggatgggag caggacacca caggccaggc ccagacagtg    1440
gccaggctg gagggtggg gtctgggct gggcccaga gaatgacctc aggtgatccc       1500
tgcccagccc atgggggat cctgccacct tccccccacc cagagggagc cctgccccga    1560
ggccctgatg atgccaccca gccccccgtg ggcagacaca gcactgacca cccctccctg    1620
tgcagacctg ctgctggagg aggagatctg tgcggacgcc caggacgggg agctggacgg    1680
gctctggacc accatcacca tctt                                          1704
```

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 6
cgcggatccc ctacgcgtgt gtggtgatg                                      29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 7
cgcggatcca ccgaggagaa gatccactt                                      29

<210> SEQ ID NO 8
<211> LENGTH: 2842
<212> TYPE: DNA
<213> ORGANISM: sheep

<400> SEQUENCE: 8

```
cctacgcgtg tgtggtgatg cacgaggctc tacacaacca ctacacacag aagtcgatct      60
ctaagcctcc gggtaaatga gccacatgcc cccgcaccag caagccctca cccagcccgc     120
cctccccggg ctccaggtcc agccaggacg ccctagcccc tccctgtgtg catgcctcct     180
gggccgccat gaataaagca cccaggccgc cctgggaccc tgcaacgctg tgcttgttct     240
ttccgaggca gagccctggt gaccgccagg cctgcggggg gtgggctgag cccactctgg     300
gccgcttggt tcagcatctg tgggggcgct gaccctctc cgggccagac acacagtgag     360
tgggtccggc agggcacctg ggggctgccc gaggcctcgg aggggcttgg ccagaggcgc     420
agcttcacgg cccctccag ccaccacatt ctgggccaga ctctgggcag gaacggggga     480
agcccccgac acctcaggga ttgaggccca acgcttcccg cctctgctcc agcccacgct     540
gaggggcagg gccgcggcct tgtccccagg cccctgttcc tgggtgccca gagtccgtgt     600
gtccactctg ggcctgcctg gagccagact ggcccagggg gaggccctgc ttcaccctca     660
ggctcccgag gtcaggcatc atcctcgtcg gccagtagct ctgcctggct ctctctgccc     720
ggggccaagc ctgtgtgccc atggggaggt cgtccctgtg cctgaaaagg gcccaggctg     780
ggagccctga acgtccaggg cagggaccta gctgctccct ggggacactg agcccagagc     840
cccagacacc aagccccagc cccgcacgca cacgagacag cccacacccca gcgtcctcca     900
cacgcactca ggcgtccacc cgcacacaag catgcttcac ccccgtcaca cacccacatg     960
cctgcacaca ctcaggtctc acgctccggg acccatggag tgatcccacg ggcccagacc    1020
cagagctggg tctcatgagc cctccctgtg acaccagct ggtccccatt ctccagcgcc    1080
cttgggctgc tcagtggccc tttcccacac tgaccacact gaccaggtca gacatccttc    1140
ctcgcctccc ctggggcacc cacgcccctc cctcgcaggc tgagacccc cctcagcccc    1200
tcgtcctggc accctcaccc ctcgggcaca gggacacagc ccggcactgt ctgccctccc    1260
tctcggggac agagcccagg cacgtgtgct ctgctgagcc tccggctcc aggcctggcc    1320
cccagggcag aggaggccag gaattgagcc tctgtcctgc ggggaggtgg ggtcagggcc    1380
ccagctcagg gcacagctca ggatgggagc aggaccccac aggccaggcc cagacagtgg    1440
ccagggctgg ggctggggct ggggcccaga gactgacctc aggtgacccc tgcccggccc    1500
atggggatc acaccgccat ccccccgcc gcagagggag ccctgccccg aagcccgat      1560
ggccccgccc agccccccgt gggcagacac agcactgacc cccctccctg tgcagatctg    1620
ctgctggagg aggagagctg tgcggacgcc caggacgggg agctggacgg gctctggacg    1680
actatctcca tcttcatcac gcccttcctg ctcagcgtct gctacagcgc caccgtgacc    1740
ctcttcaagg tggggtcca ccctgctggg ccctcgggcc cctctctgt ccccagggtc      1800
cccgcagagt ccctccctgc ccctcactgt cctccctgt ccctctctgt ccctctctgt    1860
ccctctctgt ccctctctgt ccgttcattt ccccttcacc gtaagcttga dacagattgg    1920
ggtcatttca gagggcgtct gaagagtctc tgtgccgcac gcctcccttc atgtcagtgg    1980
ggagaattca gcaagggtgg agtgctgggt gagaaatgag gcttgcggcg ctcacgagca    2040
gtgatggggc actgctgctc cctgagacct gcgcggacac cgttttccat cgcaggagaa    2100
```

| | |
|---|---|
| gcgggcaagg gaaaacgccc tcttggtctc tcttgagtaa atgtcgcgtt ttggtcatca | 2160 |
| gtccctcccc cagtgaggct agaggagttt acttctccct ctcgatggtc aggtcaggac | 2220 |
| tgtcatagac tccggatcac cttcctgtaa atgcttgctt tttgtgtgca gagagcctgt | 2280 |
| tttagctcgg gggtcctcag ctcactgagc tcgcggggca ggggtgggct cgggctggcg | 2340 |
| ccgcctgttc gggagcgcat ctccagcatg ctgtcgcaca gcttcgttgc taacaagacc | 2400 |
| gcttagtctc gtggttagac caacctgctt tctcgagtaa ttgttaattt acaggagttt | 2460 |
| cctgtatttt tcaacttata atccctagt cagataactc tttaatcacc tattctgccc | 2520 |
| cttcattttc tccctatcga tctcagcaac ccatcactgc cctcactgtc cttaaactgt | 2580 |
| cccttaactg accagactgt ccctcagtgt ccctcagag tcacctccct atcacctcac | 2640 |
| tgtccctctc tgcccctctc tgcccctctc tgtccctccc tgcccctccc cgtccctct | 2700 |
| ctgtccctct ctgcccctca ctgctcctct ctgcacctca ctgctcctca ctgccctggg | 2760 |
| ggaggcccgc atcgaggtgt ctctgctcac cccgtccccc accccgtacc cccgccagg | 2820 |
| tgaagtggat cttctcctcg gt | 2842 |

<210> SEQ ID NO 9
<211> LENGTH: 2840
<212> TYPE: DNA
<213> ORGANISM: sheep

<400> SEQUENCE: 9

| | |
|---|---|
| cctacgcgtg tgtggtgatg cacgaggctc tgcacaacca ctacacacag aagtcggtct | 60 |
| ctaagcctcc gggtaaatga gccacacgcc cccgcaccag caagccctca cccagcccgc | 120 |
| cctccccggg ctccaggtcc agccaggacg ccctagcccc tccctgtgtg catgcctcct | 180 |
| gggccgccat gaataaagca cccaggccgc cctgggaccc tgcagcgctg tgctggttct | 240 |
| ttccgaggca gagccctggt gatcgccagg cctgcggggg gcgggctgag cccactctgg | 300 |
| gccgcttggt tcagcatctg tgggggcgct gaccctctc cgggccagac acacagtgag | 360 |
| tgggtccggc agggcacctg ggggctgccc gaggcctcgg aggggcttgg ccagaggcgc | 420 |
| agctccacgg cccctccag ccaccacatt ctgggccaga ctctgggcag gaacggggga | 480 |
| agccccccgac acctcaggga ttgaggccca acgcttcccg cctctgctcc agcccacgct | 540 |
| gaggggcagg gccgcggcct tgtccccagg cccctgttcc tgggtgccca gagtccgtgt | 600 |
| gtccactctg ggcctgcctg gagccagact ggcccagggg gaggccctgc ttcaccctca | 660 |
| ggctcccgag gtcaggcatc atcctcgtcg gccagtagct ctgcctggct ctctctgccc | 720 |
| ggggccaagc ctgtgtgccc atggggaggt cgtccctgtg cctgaaaagg gcccaggctg | 780 |
| ggagccctga acgtccaggg cagggaccta gctgctccct ggggacactg agcccagagc | 840 |
| cccagacacc aagccccagc ccgcacgca cacgagacag cccacaccca gcgtcctcca | 900 |
| cacccactca ggcgtccacc cgcacacaag catgcttcac ccccgtcaca cacccacatg | 960 |
| cctgcacaca ctcaggtctc acgctccggg acccatggag tgatcccacg ggcccagacc | 1020 |
| cagagctggg tctcatgagc cctccctgtg acaccagct ggtccccatc ctccagcgcc | 1080 |
| cttgggctgc tcagtggccc tttcccacac tgaccacact gaccaggtca gacatccttc | 1140 |
| ctcgcctccc ctggggcacc cacgcccctc ccttgcaggc tgagacccc cctcagcccc | 1200 |
| tcgtcctggc accctcaccc ctcgggcaca gggacacagc ccggcactgt ctgccctccc | 1260 |
| tctcggggac agagcccagg cacgtgtgct ctgctgagcc tccggctcc aggcctggcc | 1320 |
| cccagggcag aggaggccag gaattgagcc tctgtcctgc ggggaggtgg ggtcagggcc | 1380 |

```
ccagctcagg gcacagctca ggatgggagc aggaccccac aggccaggcc cagacagtgg    1440
ccagggctgg ggctggggct ggggcccaga gactgacctc aggtgacccc tgcccggccc    1500
atgggggatc acaccgccat ccccccccgcc gcagagggag ccctgccccg aagcccccgat   1560 ggccccgccc agccccccgt gggcagacac agcactgacc cccctccctg tgcagatctg    1620
ctgctggagg aggagagctg tgcggacgcc caggacgggg agctggacgg gctctggacg    1680
actatctcca tcttcatcac gctcttcctg ctcagcgtct gctacagtgc caccgtgacc    1740
ctcttcaagg tggggcccca ccctgctggg ccctcgggcc cctctctgt ccccagggtc     1800 cccgcagagt ccctccctgc ccctcactgt ccctccctgt ccctctctgt ccctctctgt    1860
ccctctctgt ccctctctgt ccgctcattt tcccttcacc gtaagcttga gacagattgg    1920
ggtcatttca gagggcgtct gaagagtctc tgtgccgcac gcctcccttc atgtcagtgg    1980
ggagaattca gcaagggtgg agtgctgggt gagaaatgag gcttgcggcg ctcacgagca    2040
gtgatggggc actgctgctc cctgagacct gcgcggacac cgttttccat cgcaggagaa    2100
gcgggcaagg gaaaacgccc tcttggtctc tcttgagtaa atgtcgcgtt ttggtcatca    2160
gtccctcccc cagtgaggct agaggagttt acttctcccct ctcgatggtc aggtcaggac    2220
tgtcatagac tccggatcac cttcctgtaa atgcttgctt tttgtgtgca gagcctgttt    2280
tagctcgggg gtcctcagct cactgagctc gcggggcagg ggtgggctcg ggctggcgcc    2340
gcctgttcgg gagcggcatc tccagctgct gtcgcacagc ttcgttgcta acaagaccgc    2400
ttagtctcgt ggttagacca acctgctttc tcgagtaatt gttaatttac aggagtttcc    2460
tgtatttttc aacttataat cccctagtca gataactctt taatcaccta ttctgcccct    2520
tcattttctc cctatcgatc tcagcaaccc atcactgccc tcactgtcct taaactgtcc    2580
cttaactgac cagactgtcc ctcagtgtcc cctcagagtc acctccctat cacctcactg    2640
tccctctctg cccctctctg cccctctctg tccctctctg tccctccccg tccctctct     2700 gtccctctct gccctcact gctcctctct gcacctcact gctcctcact gccctggggg     2760
aggcccgcat cgaggtgtct ctgctcaccc cgtcccccac cccgtccccc ccgccaggtg    2820
aagtggatct tctcctcggt                                                 2840
```

<210> SEQ ID NO 10
<211> LENGTH: 3120
<212> TYPE: DNA
<213> ORGANISM: rabbit

<400> SEQUENCE: 10

```
ctccccccca cgccgcagct gtgcaccccg cacacaaata agcacccag ctctgccctg      60 agaggctgtc ctgattcctt ccaaggcaga ggcttccact cgggccggac agggttgggc    120
gggcgccgtg ggctctgctg tggccagcag ccagaacggt caacagtggg acaggggcag    180
acccacagca caggggcctg ccaagaactg ggctcagccg gagtgctgtg gcaggtcccc    240
ccttgcagct agcacgtgtg tgctgggcag gcagaggccc caggggagg agcacacagc     300 taccacctct gcaagagcct ggcctggcgc ccaggtccca gtccacaggg tgtgtagtac    360
acagagcctc atcttaccac agatgtaggg acagacccac cacgcccctg cacccccaccc   420 agcctcgccc cttgtgggac cagggctacc actccactcc ccgcccaga gcagcagaag     480 caggtggcat cctcagcaga gggacagtct cacccctcca cggcactgag ccctgaccca    540
tcaaacaagc ccctcctgct gcacagcacc tgtgtgcaca tcacacacac acacacacac    600
```

```
acactgaggc ctgaccccat caaacaagcc cctcctgctg cacagcacct gtgtgcacat    660
cacacacaca cacacacaca cactgaggcc tgacccatc ctgccctcct gctgcatggc     720
acctgtgtgc acatcacaca cacatgcaca cacacactca cacacactga gccctgaccc    780
catcctgccc tcctgctgca tggcacctgt gtgcacatca cacacacaca cacacacaca    840
cacacactga gccctgaccc catcctgccc tcctgctgca tggcacctgt gcacacatca    900
caaacacgcc tgcctcatac actggcactc agaaggggcc cctgtacacg catacacatg    960
cacacacctt gacacatggg cccctacacg catcaca cacactcatg cacactcctc      1020
acacatggcc ctcctgcaca tacattgcac acacatgtgc acagacctca caatgggccc    1080
ctgcacacac attgtacaca cgcatgtgca cacttcac acatgggccc cctgcacatg      1140
cattgcacac acagacacac acatgtgcat tcctcacaca ttggggcctt gcaagggatg    1200
ccctgcacac acattgcaca tgctcacatg tgcacacacc ccacactgga gccttgcata    1260
gggccccctg tacacacacc atgcatacac acacacctca cacaagggc cccctacata     1320 cgcaaaacac acacacacac atgcacacac ctcatacacg gcccctac acacatcaca     1380 cacacacaca cacacgta tgcatgcctc acacacagac cttgcaaggg gccccctgca      1440
catgcatcaa acacatatgc acatgtttca cacacggt ccctacaca cactgcacac       1500 gcacacatgt gtacatgctt cacacactgg ggccttgcat gggtccct gcatagcata      1560 gcacccagag ccacgccagg tgcctgggca catggacact ggtgcacaca cagcacccaa    1620
gcccagctct cccatccaag gggcaccagc accccccact cacgagcacc ctgaattcct    1680
gctccccaca agcgaacgtg caccctacct ctccagacgt cccttcctg tggccactcc     1740 cataggtatt ggcgagaccc tcccttgacc cttgggcctg gtcacccagg ggacaggaga    1800
gggccaagtt gggccacagt accactgccc agcagggtg aggcaagcag agggtgggtc     1860
tgtgaggcgt ctggccagcc gtgctggggc ccaggtgggg agcagctggg tggctgaggt    1920
ggcttccttg caggtggttg gggggagctg gccccacaag tgccactgcc cagcactgtc    1980
cagtgcttcc ccctgaacct cccggccacc catccccagc tgcagccgca gaggagtgc     2040 ccctcggcct cctcggcaag acgcacgctg actgcccctc cccatccaga gctgcagctg    2100
gacgagagct gtgccgaggc ccaggacggg gagctggacg ggctgtggac caccatcacc    2160
atcttcatct ccctcttcct gctcagcgtg tgctacagcg ccacagtcac cctcttcaag    2220
gtgggtgctg cacccggcac gggtgggctg ggggccaggg gcgggggccg ggggccaggc    2280
cctcctcacc ccgcgccgcc gctgctgcag gtgaagtgga tcttctcgtc cgtggtggag    2340
ctgaaacaca ccatcgctcc cgactacagg aacatgatcg gcagggggc ctaggccctt     2400 cgttctcaca gcctgcctcc ctggccagca ggagcccccg cctccgcctc ggaccccatg    2460
gctctctgct ctggccgctc cggacccctc cgcctcggga aagcgcgca gctgatgcct    2520 gccgccccct ccacgcagca gtgcggacag cacgcatctg tcgtccaccc ggcaggaccc    2580
cacccagggc cagccctgac cgccagcctc ctggactcag gctcctctg agaaaaggcc     2640 cacttgttgg tccctcagc ccacacccag gcagcctccg gtgggtgctt ccctggaccc     2700
cagcctgagg cctatgcttg ttctcctgtg gctcttactc agaggccgt gctggactcc    2760 cacccacagg gacagtgccc tgctccaacc ctcactgcac tggggtcat ggggccacct     2820 tctgtgcagg ggtcctggct ccaaggagaa cactcgaagg gcctgcttgg ccacctggca    2880
ccacgggagc ccgctgggt agcttggcag ggaccctga gtagaggtgg gtgcacccag     2940
ccagaaagcc tgctggatgg acaggagcct ggcgtccggg cccaggcag gcagacacgg    3000
```

```
                                          -continued cttcatggac aggagaggcc aaggaacatc agcaaagaga gacagctggg ccggcgttc    3060 cagccagacc catcctgcag cccagcatcg gccccgtgta ctacagcagg gacagccagt   3120

<210> SEQ ID NO 11
<211> LENGTH: 2587
<212> TYPE: DNA
<213> ORGANISM: rabbit

<400> SEQUENCE: 11
gcgagacgcc tgccagggca ccgccagtga ccctgaggcc cagcctcgcc gctccctccc     60
ctcagtggac ccattcccac cacagtcctc cagcccctcc cctcccggcc ctcaccccct    120
ccttggcttt aaccttgcga atgttggtga gatggatgaa taaagtgaat cttttgcactt   180 gtgacttctc tctgcttctt catttaatgg ttattactca tggtttccca gttgccctaa    240
agtcaccgcc atttcatcct ccatcccacc ctgccctgct gtcctccggg agacaccact    300
ccctgaaacc cacaggcccc tgtcttcaca ccgccgaccc cgaccacacg tgagggcttt    360
gcttcgtgtc tcactcccct catcgagccc cagagtcctc ctttagtgtt cttacagtca    420
catacagtta tacagtttga gtcaatccaa cctgccctgc caatttccca aaacaaagat    480
tttcagaata aaacagctat gaagaaagtc atttatggaa gcatgatata caacaacaaa    540
acaatgcaaa caacctaact gaataagcag agggaaatgt tcagacacac tatggggctt    600
gggcttcatg gagtattaca ccttcattac attttttaaac ttgtattaag gagctcctat    660
attacaagga ttatactaga gcactttcca tgacctaatt aattctcatt acactgtgag    720
gttaaaagca ttagttaaaa tattgggcag gctccctata gccaacagtt gttcatattc    780
cataacccaa ccatcattta ggtgactcag ggtccttgtc caccaagaac tttggcaaga    840
atgttcagag caacttcctt tataaaagtc aaaaattgga agtaactcaa atgtctacca    900
acagtagaat gggctgttaa ttggcatatg tttacatatt agaatgctgt taataaaga    960 gaattaacaa actacaacta tccctaataa cataggtgac tcataaacat gatgttaagc   1020
acaagaaccc aaacacaaaa gacacactgt gtatgtttc atccatagga agttcaaaac    1080
tagttaaaaa ttgaattaga aattgagatg aagtttactc ttggctgggg gtgtggagtg   1140
aggcggtgcc tggtgggga cagaaagtgg ctgctgggt cttggtgatg ttctagtcct    1200
cactgtggtg tgtgctactc tgaaaatgta ttgagtacac aattaggttt tgtgctttca    1260
ttatactcca aagtaagttc tcataaacat tgccttacac ggggtctaca gataagagag    1320
actaagagga atgagtaaca gatcaaggcc acacagctgg taggcatggg cctgggatca    1380
aaccctgtct gcccaattct gctctcttga gccctacact attctttcca gcactggaat    1440
gccatgcaga acagggagta ggacatgcta cctccctagg gtctcctcct ttacccacct    1500
aaccaggagc acccatacat agaaacagga tggaaaagac catcagcaat ggaacaaggg    1560
agagattaac cttgttcagt attgtgatcc catgtaggaa agattgtggg aggagggctg    1620
cacacagagc accgtccccc ttctatgtgc ccaccgctct gtgccccctt atctgctcac    1680
ccgcccagcg tgcattcact cagcacccctt ttcgcctgcc ctctgaaaga ggtgcagaag   1740
taactaaacc agcttccctc cttcagtgac ttggaatcca gttttcctcc tctatttccc    1800
cctccttttc agtgcaggag cctggagaaa tgtgatttgt gttattataa atttcccaca    1860 tcatttgtg taagggaaaa tatactcaac agtcataact ggtaaaactg ctgtgaaaac    1920
taagagaagt aattcatgcg aaggttgagc accagccttg tatatactaa gagatccaga   1980
```

-continued

```
agtgttagtc accgttagaa ataagaagga gtagctcaat ttgactagtt cctggttcac      2040
tccttgaaca tgttcttcag ttatcatctt tcagtcccaa atgattgaac ttggaattaa      2100
ctcacatgga ttctagacct gtgccgagaa tggctgccac tcgtgctcta gagctctggg      2160
gatgaggctg tccctactgt ggtgtgctac aggtctaaca acacaccagg ttttgaagac      2220
ttagcactat gaatatatat atatattata ttccaataaa tttaacatac tttctacttt      2280
cattgcatgt tgagatagta atctactttg gatatatttg gttaaaccaa actattctca      2340
agacaaattt cataggttta tggtttttt acaatttaat caaaatataa acatagtcca       2400
aacaattaat ccatttaaag tggagaatgg cccaagtgtt tgggcccctg ctacccattt      2460
ttaagaccag atgttgctct tggcttctgg cttttgcttg gctcagccct ggccattgca      2520
gccatctgag gagtaaacag tggatggaag acatctcccc ccaccctgcc cataaagctc      2580
gggatcc                                                                2587
```

<210> SEQ ID NO 12
<211> LENGTH: 1205
<212> TYPE: DNA
<213> ORGANISM: rabbit
<220> FEATURE:
<221> NAME/KEY: Unsure
<222> LOCATION: (997)
<223> OTHER INFORMATION: n at position 997 is uncertain
<221> NAME/KEY: Unsure
<222> LOCATION: (1127)
<223> OTHER INFORMATION: n at position 1127 is uncertain

<400> SEQUENCE: 12

```
cttcagcgtg aaccacgccc tcccgctgag tctcacgcac cccggtgca ggcagtccgg        60 cctcacctgg aaggtgcact gactgaagac actgcaaggg gtgagagcat ttctcaggaa      120
agagccctga gtttagaagg ccagagagca gagggctgag ggctgccttg cgctgcaacc      180
catggaaaca caggcttagc agatgttcaa gctccgggga tccacactgg gtgagggcag      240
gcgtccagcc tgacatggcc cccacagact cgcccacagg tgacgccaga tgaggacggt      300
caaggatcgg gggatcctac atgcccaggg gcaccaagac agccaggaga gcaccagagg      360
ccacaagaga ggcctgggac agtctccctg ctgacatcca gagcccaggc cccacttggc      420
agagctggct gagaacacgt ctctgcggtg aagctgcccc cgtcctgggt gttgctcggc      480
gggctaagcc gactgacgcg gggcgggcca ggccatcggc cccacggcct gcagcttcct      540
ccccagccca ggccacgtgg gctcctggct gaactggccg ctcgctgagc tctcaccccc      600
ccacccagca gcaggccggg cggtgctgcc atgagctcca ttcccaccac acaagcgaca      660
gcccgggcag cgccccaggc ccacggggcg tttgctgtgc ggctcgcact cgctgctcag      720
ggccagcgca gggtgcagca gggactcacc aacccgcccc gactcggctg gcacgtttac      780
tggaggcctc tgagcctgac cgtggcagtg gggcccgagc aggctccagg ctgccccctg      840
caccctgggc ttgccgctcc gggacccctg gtgggcacct tcccagatgt gctcccaccg      900
tgcctccttg gggctctggg ctcatagcgg tcactctccg ccttctctcc tcccagccct      960
ttcctgcctc cctatggccc catctagctc tgccctntct agagcctcta cctggaagga     1020
atctgctgtt ggaccaagac accacccgca gcacaggtgg gcgccttgca ctgtgctagg     1080
ccctccccgc acagaaaagg gccctaggct ctggaggctg ctgctgnctc tggggctggc     1140
atcgggcgca ccctgcaccc tgcaccctga ggaaactcag gcctgcccgc tccaggcctg     1200
tccct                                                                 1205
```

<210> SEQ ID NO 13
<211> LENGTH: 668
<212> TYPE: DNA
<213> ORGANISM: rabbit

<400> SEQUENCE: 13

```
gaagctttac ttgttggggg cgggcaggtc taagggacct gccaggtgtg ggggctgggc      60
ttgactcagc aggagccttc tagaaggaaa gctctggaga aggtggggc agagggcggg     120
aaaggcctgt gaggaggcgg gtggtgggca gggccactgg aaggagggg ctgggggtga     180
cactcaggtt ggcactgggg aggacctgag gaggcaggtg ccaggcacag agctgaacct     240
gggcagggca ggggcaggta acaagaagga ttctccttgg agcctggtcc agggtggtcc     300
agggcggtcc agggcctggg gtttgcaagc tgggctgtga cagggcctct ctccccaggg     360
gcaagcagca aagcctgggc acagagccca agcccccac acagagaagc tccccagggc      420
agggcctgca gggcttgggg gaccttcttg gagcaggcag aggacagagg catgagatca     480
gcctcccaga ggctggaatg ataggtccag caggaggggc ccacatgggc tctggttagc     540
aggagaaaac agcccccagg tccccatggc caccacgcac cgactgctgg tgaagctttg     600
ggtggcagac gagagccaca tggcagctgc tcctgtcact ctctgggagt gcatcgaggg     660
gcgtcgac                                                             668
```

<210> SEQ ID NO 14
<211> LENGTH: 45
<212> TYPE: PRT
<213> ORGANISM: camel

<400> SEQUENCE: 14

```
Glu Pro Leu Leu Glu Glu Ser Cys Ala Glu Ala Gln Ser Gly Glu
 1               5                  10                  15
Leu Asp Gly Leu Trp Thr Thr Ile Ser Ile Phe Ile Thr Leu Phe Leu
                20                  25                  30
Leu Ser Val Cys Tyr Ser Ala Thr Val Thr Leu Phe Lys
        35                  40                  45
```

<210> SEQ ID NO 15
<211> LENGTH: 44
<212> TYPE: PRT
<213> ORGANISM: Homo sapiens

<400> SEQUENCE: 15

```
Glu Leu Gln Leu Glu Glu Ser Cys Ala Glu Ala Gln Asp Gly Glu Leu
 1               5                  10                  15
Asp Gly Leu Trp Thr Thr Ile Thr Ile Phe Ile Thr Leu Phe Leu Leu
                20                  25                  30
Ser Val Cys Tyr Ser Ala Thr Val Thr Phe Phe Lys
        35                  40
```

<210> SEQ ID NO 16
<211> LENGTH: 44
<212> TYPE: PRT
<213> ORGANISM: Homo sapiens

<400> SEQUENCE: 16

```
Glu Leu Gln Leu Glu Glu Ser Cys Ala Glu Ala Gln Asp Gly Glu Leu
 1               5                  10                  15
Asp Gly Leu Trp Thr Thr Ile Thr Ile Leu Ile Thr Leu Phe Leu Leu
                20                  25                  30
```

Ser Val Cys Tyr Ser Ala Thr Val Thr Phe Phe Lys
        35                  40

<210> SEQ ID NO 17
<211> LENGTH: 44
<212> TYPE: PRT
<213> ORGANISM: Homo sapiens

<400> SEQUENCE: 17

Glu Leu Gln Leu Glu Glu Ser Cys Ala Glu Ala Gln Asp Gly Glu Leu
 1               5                  10                  15

Asp Gly Leu Trp Thr Thr Ile Thr Ile Phe Ile Thr Leu Phe Leu Leu
            20                  25                  30

Ser Val Cys Tyr Ser Ala Thr Val Thr Phe Phe Lys
        35                  40

<210> SEQ ID NO 18
<211> LENGTH: 44
<212> TYPE: PRT
<213> ORGANISM: mouse

<400> SEQUENCE: 18

Gly Leu Gln Leu Asp Glu Thr Cys Ala Glu Ala Gln Asp Gly Glu Leu
 1               5                  10                  15

Asp Gly Leu Trp Thr Thr Ile Thr Ile Phe Ile Ser Leu Phe Leu Leu
            20                  25                  30

Ser Val Cys Tyr Ser Ala Ala Val Thr Leu Phe Lys
        35                  40

<210> SEQ ID NO 19
<211> LENGTH: 44
<212> TYPE: PRT
<213> ORGANISM: mouse

<400> SEQUENCE: 19

Gly Leu Asp Leu Asp Asp Val Cys Ala Glu Ala Gln Asp Gly Glu Leu
 1               5                  10                  15

Asp Gly Leu Trp Thr Thr Ile Thr Ile Phe Ile Ser Leu Phe Leu Leu
            20                  25                  30

Ser Val Cys Tyr Ser Ala Ser Val Thr Leu Phe Lys
        35                  40

<210> SEQ ID NO 20
<211> LENGTH: 45
<212> TYPE: PRT
<213> ORGANISM: mouse

<400> SEQUENCE: 20

Pro Gly Leu Gln Leu Asp Glu Thr Cys Ala Glu Ala Gln Asp Gly Glu
 1               5                  10                  15

Leu Asp Gly Leu Trp Thr Thr Ile Thr Ile Phe Ile Ser Leu Phe Leu
            20                  25                  30

Leu Ser Val Cys Tyr Ser Ala Ala Val Thr Leu Phe Lys
        35                  40                  45

<210> SEQ ID NO 21
<211> LENGTH: 44
<212> TYPE: PRT
<213> ORGANISM: mouse

<400> SEQUENCE: 21

```
Glu Leu Glu Leu Asn Glu Thr Cys Ala Glu Ala Gln Asp Gly Glu Leu
  1               5                  10                  15

Asp Gly Leu Trp Thr Thr Ile Thr Ile Phe Ile Ser Leu Phe Leu Leu
                 20                  25                  30

Ser Val Cys Tyr Ser Ala Ser Val Thr Leu Phe Lys
                 35                  40

<210> SEQ ID NO 22
<211> LENGTH: 44
<212> TYPE: PRT
<213> ORGANISM: mouse

<400> SEQUENCE: 22

Glu Leu Glu Leu Asn Gly Thr Cys Ala Glu Ala Gln Asp Gly Glu Leu
  1               5                  10                  15

Asp Gly Leu Trp Thr Thr Ile Thr Ile Phe Ile Ser Leu Phe Leu Leu
                 20                  25                  30

Ser Val Cys Tyr Ser Ala Ser Val Thr Leu Phe Lys
                 35                  40

<210> SEQ ID NO 23
<211> LENGTH: 44
<212> TYPE: PRT
<213> ORGANISM: sheep

<400> SEQUENCE: 23

Leu Leu Leu Glu Glu Glu Ser Cys Ala Asp Ala Gln Asp Gly Glu Leu
  1               5                  10                  15

Asp Gly Leu Trp Thr Thr Ile Ser Ile Phe Ile Thr Pro Phe Leu Leu
                 20                  25                  30

Ser Val Cys Tyr Ser Ala Thr Val Thr Leu Phe Lys
                 35                  40

<210> SEQ ID NO 24
<211> LENGTH: 44
<212> TYPE: PRT
<213> ORGANISM: sheep

<400> SEQUENCE: 24

Leu Leu Leu Glu Glu Glu Ser Cys Ala Asp Ala Gln Asp Gly Glu Leu
  1               5                  10                  15

Asp Gly Leu Trp Thr Thr Ile Ser Ile Phe Ile Thr Leu Phe Leu Leu
                 20                  25                  30

Ser Val Cys Tyr Ser Ala Thr Val Thr Leu Phe Lys
                 35                  40

<210> SEQ ID NO 25
<211> LENGTH: 19
<212> TYPE: PRT
<213> ORGANISM: cow

<400> SEQUENCE: 25

Leu Leu Leu Glu Glu Glu Ile Cys Ala Asp Asp Leu Asp Gly Glu Leu
  1               5                  10                  15

Asp Gly Leu

<210> SEQ ID NO 26
<211> LENGTH: 19
<212> TYPE: PRT
<213> ORGANISM: cow
```

-continued

```
<400> SEQUENCE: 26

Leu Leu Leu Glu Glu Glu Ile Cys Ala Asp Ala Gln Asp Gly Glu Leu
  1               5                  10                  15

Asp Gly Leu

<210> SEQ ID NO 27
<211> LENGTH: 43
<212> TYPE: PRT
<213> ORGANISM: rabbit

<400> SEQUENCE: 27

Leu Gln Leu Asp Glu Ser Cys Ala Glu Ala Gln Asp Gly Glu Leu Asp
  1               5                  10                  15

Gly Leu Trp Thr Thr Ile Thr Ile Phe Ile Ser Leu Phe Leu Leu Ser
             20                  25                  30

Val Cys Tyr Ser Ala Thr Val Thr Leu Phe Lys
         35                  40

<210> SEQ ID NO 28
<211> LENGTH: 27
<212> TYPE: PRT
<213> ORGANISM: camel

<400> SEQUENCE: 28

Val Lys Trp Ile Phe Ser Ser Val Val Glu Leu Lys Arg Thr Ile Val
  1               5                  10                  15

Pro Asp Tyr Arg Asn Met Ile Gly Gln Gly Ser
             20                  25

<210> SEQ ID NO 29
<211> LENGTH: 27
<212> TYPE: PRT
<213> ORGANISM: Homo sapiens

<400> SEQUENCE: 29

Val Lys Trp Ile Phe Ser Ser Val Val Asp Leu Lys Gln Thr Ile Ile
  1               5                  10                  15

Pro Asp Tyr Arg Asn Met Ile Gly Gln Gly Ala
             20                  25

<210> SEQ ID NO 30
<211> LENGTH: 27
<212> TYPE: PRT
<213> ORGANISM: Homo sapiens

<400> SEQUENCE: 30

Val Lys Trp Ile Phe Ser Ser Val Val Asp Leu Lys Gln Thr Ile Ile
  1               5                  10                  15

Pro Asp Tyr Arg Asn Met Ile Gly Gln Gly Ala
             20                  25

<210> SEQ ID NO 31
<211> LENGTH: 27
<212> TYPE: PRT
<213> ORGANISM: Homo sapiens

<400> SEQUENCE: 31

Val Lys Trp Ile Phe Ser Ser Val Val Asp Leu Lys Gln Thr Ile Ile
  1               5                  10                  15

Pro Asp Tyr Arg Asn Met Ile Gly Gln Gly Ala
```

```
                    20                  25

<210> SEQ ID NO 32
<211> LENGTH: 27
<212> TYPE: PRT
<213> ORGANISM: mouse

<400> SEQUENCE: 32

Val Lys Trp Ile Phe Ser Ser Val Val Glu Leu Lys Gln Thr Leu Val
  1               5                  10                  15

Pro Glu Tyr Lys Asn Met Ile Gly Gln Ala Pro
                    20                  25

<210> SEQ ID NO 33
<211> LENGTH: 27
<212> TYPE: PRT
<213> ORGANISM: mouse

<400> SEQUENCE: 33

Val Lys Trp Ile Phe Ser Ser Val Val Glu Leu Lys Gln Thr Ile Ser
  1               5                  10                  15

Pro Asp Tyr Arg Asn Met Ile Gly Gln Gly Ala
                    20                  25

<210> SEQ ID NO 34
<211> LENGTH: 27
<212> TYPE: PRT
<213> ORGANISM: mouse

<400> SEQUENCE: 34

Val Lys Trp Ile Phe Ser Ser Val Val Glu Leu Lys Gln Thr Leu Val
  1               5                  10                  15

Pro Glu Tyr Lys Asn Met Ile Gly Gln Ala Pro
                    20                  25

<210> SEQ ID NO 35
<211> LENGTH: 27
<212> TYPE: PRT
<213> ORGANISM: mouse

<400> SEQUENCE: 35

Val Lys Trp Ile Phe Ser Ser Val Val Gln Val Lys Gln Thr Ala Ile
  1               5                  10                  15

Pro Asp Tyr Arg Asn Met Ile Gly Gln Gly Ala
                    20                  25

<210> SEQ ID NO 36
<211> LENGTH: 27
<212> TYPE: PRT
<213> ORGANISM: mouse

<400> SEQUENCE: 36

Val Lys Trp Ile Phe Ser Ser Val Val Gln Val Lys Gln Thr Ala Ile
  1               5                  10                  15

Pro Asp Tyr Arg Asn Met Ile Gly Gln Gly Ala
                    20                  25

<210> SEQ ID NO 37
<211> LENGTH: 27
<212> TYPE: PRT
<213> ORGANISM: rabbit

<400> SEQUENCE: 37
```

```
Val Lys Trp Ile Phe Ser Ser Val Val Glu Leu Lys His Thr Ile Ala
 1               5                  10                  15

Pro Asp Tyr Arg Asn Met Met Gly Gln Gly Ala
             20                  25
```

```
<210> SEQ ID NO 38
<211> LENGTH: 8
<212> TYPE: PRT
<213> ORGANISM: sheep

<400> SEQUENCE: 38
```

```
Val Lys Trp Ile Phe Ser Ser Val
 1               5
```

```
<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 39
cgcaagcttc ctacacgtgt gtggtgatg                                    29

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 40
gtcgacgccc ctcgatgcac tcccagag                                     28

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 41
ggtaccctct ccctccccca cgccgcagc                                    29

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 42
atatctcaga actggctgtc cctgctgtag tacacgg                           37

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 43
gtcgacactg gacgctgaac ctcgcgg                                      27
```

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 44
ggtaccgggg gcttgccggc cgtcgcac                                         28

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 45
gcggccgctg gcgaggagac caagctggag atcaaacg                              38

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 46
gtcgacgcag cccaaagctg ttgcaatggg gcagcg                                36

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 47
atatggtacc gcgagacgcc tgccagggca ccgcc                                 35

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 48
ggatcccgag ctttatgggc agggtggggg                                       30

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 49
atatgtcgac ctgggataag catgctgttt tctgtctgtc cc                         42

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence:primer

```
<400> SEQUENCE: 50
ctaggtacca gcaggtgggg gcacttctcc c                                  31

<210> SEQ ID NO 51
<211> LENGTH: 1719
<212> TYPE: DNA
<213> ORGANISM: Artificial Sequence
<220> FEATURE:
<223> OTHER INFORMATION: Description of Artificial Sequence:human
      immunoglobulin heavy chain Cγ1 gene segment
      flanked by nucleotides derived from the rabbit
      heavy chain.

<400> SEQUENCE: 51
tgacctacct accctgccaa ggtcaggggt cctccaaggc aagggatcac atggcaccac     60
ctctcttgca gcctccacca agggcccatc ggtcttcccc ctggcaccct cctccaagag    120
cacctctggg ggcacagcgg ccctgggctg cctggtcaag gactacttcc ccgaaccggt    180
gacggtgtcg tggaactcag gcgccctgac cagcggcgtg cacaccttcc cggctgtcct    240
acagtcctca ggactctact ccctcagcag cgtggtgacc gtgccctcca gcagcttggg    300
cacccagacc tacatctgca acgtgaatca caagcccagc aacaccaagg tggacaagaa    360
agttggtgag aggccagcac agggagggag ggtgtctgct ggaagccagg ctcagcgctc    420
ctgcctggac gcatcccggc tatgcagccc cagtccaggg cagcaaggca ggccccgtct    480
gcctcttcac ccggaggcct ctgcccgccc cactcatgct cagggagagg gtcttctggc    540
tttttcccca ggctctgggc aggcacaggc taggtgcccc taacccaggc cctgcacaca    600
aaggggcagg tgctgggctc agacctgcca agagccatat ccgggaggac cctgcccctg    660
acctaagccc accccaaagg ccaaactctc cactccctca gctcggacac cttctctcct    720
cccagattcc agtaactccc aatcttctct ctgcagagcc caaatcttgt gacaaaactc    780
acacatgccc accgtgccca ggtaagccag cccaggcctc gccctccagc tcaaggcggg    840
acaggtgccc tagagtagcc tgcatccagg acaggcccc agccgggtgc tgacacgtcc    900
acctccatct cttcctcagc acctgaactc ctggggggac cgtcagtctt cctcttcccc    960
ccaaaaccca aggacaccct catgatctcc cggacccctg aggtcacatg cgtggtggtg   1020
gacgtgagcc acgaagaccc tgaggtcaag ttcaactggt acgtggacgg cgtggaggtg   1080
cataatgcca agacaaagcc gcgggaggag cagtacaaca gcacgtaccg tgtggtcagc   1140
gtcctcaccg tcctgcacca ggactggctg aatggcaagg agtacaagtg caaggtctcc   1200
aacaaagccc tcccagcccc catcgagaaa accatctcca agccaaaagg tgggacccgt   1260
ggggtgcgag ggccacatgg acagaggccg gctcggccca ccctctgccc tgagagtgac   1320
cgctgtacca acctctgtcc ctacagggca gccccgagaa ccacaggtgt acaccctgcc   1380
cccatcccgg gatgagctga ccaagaacca ggtcagcctg acctgcctgg tcaaaggctt   1440
ctatcccagc gacatcgccg tggagtggga gagcaatggg cagccggaga acaactacaa   1500
gaccacgcct cccgtgctgg actccgacgg ctccttcttc ctctacagca agctcaccgt   1560
ggacaagagc aggtggcagc aggggaacgt cttctcatgc tccgtgatgc atgaggctct   1620
gcacaaccac tacacgcaga agagcctctc cctgtctccg ggtaaatgag cgctgtgccg   1680
gcgagctgcc cctctccctc ccccccacgc cgcagctgt                          1719

<210> SEQ ID NO 52
<211> LENGTH: 390
<212> TYPE: DNA
```

<210> SEQ ID NO 52
<211> LENGTH: 390
<212> TYPE: DNA
<213> ORGANISM: Artificial Sequence
<220> FEATURE:
<223> OTHER INFORMATION: Description of Artificial Sequence:a VH gene
    segment encoding a human VH element polypeptide
    sequence, with flanking sequences derived from
    rabbit immunoglobulin DNA sequences.

<400> SEQUENCE: 52

```
tgagtgacag tgtcctgacc atgtcgtctg tgtttgcagg tgtccagtgt gaggtgcagc      60
tgttggagtc cggggaggt ctcgtccagc caggggggac cctgagactc acctgcgcag     120
tctctggatt caccttcagt agctatgcaa tgagctggt ccgccaggct ccagggaagg     180
ggctggaatg ggtcggagcc attagtggta gtggtagcac atactacgcg gacagcgtga     240
aaggccgatt caccatctcc agagacaact ccaagaacac gctgtatctg caaatgaaca     300
gtctgagagc cgaggacacg gccgcctatt actgtgcgaa agacacagtg aggggccctc     360
aggctgagcc cagacacaaa cctccctgca                                      390
```

<210> SEQ ID NO 53
<211> LENGTH: 445
<212> TYPE: DNA
<213> ORGANISM: Artificial Sequence
<220> FEATURE:
<223> OTHER INFORMATION: Description of Artificial Sequence:containing a
    human immunoglobulin light chain Cκ gene segment
    flanked by 50 nuleotides derived from the rabbit
    light chain immunoglobulin Kappa1 gene.

<400> SEQUENCE: 53

```
catccacatg gcacccaggg gagatgtcca ctggtaccta agcctcgcca tcctgtttgc      60
ttctttcctc aggaactgtg gctgcaccat ctgtcttcat cttcccgcca tctgatgagc     120
agttgaaatc tggaactgcc tctgttgtgt gcctgctgaa taacttctat cccagagagg     180
ccaaagtaca gtggaaggtg gataacgccc tccaatcggg taactcccag gagagtgtca     240
cagagcagga cagcaaggac agcacctaca gcctcagcag caccctgacg ctgagcaaag     300
cagactacga gaaacacaaa gtctacgcct gcgaagtcac ccatcagggc ctgagctcgc     360
ccgtcacaaa gagcttcaac aggggagagt gttagagcga gacgcctgcc agggcaccgc     420
cagcgaccct gaggcccagc ctcgc                                           445
```

<210> SEQ ID NO 54
<211> LENGTH: 632
<212> TYPE: DNA
<213> ORGANISM: Artificial Sequence
<220> FEATURE:
<223> OTHER INFORMATION: Description of Artificial Sequence:a Vκ gene
    segment encoding a human Vκ element polypeptide
    sequence, flanking by sequences derived from
    rabbit immunoglobulin DNA.

<400> SEQUENCE: 54

```
ggcaggctgc tcccacccca tgcaggaggc agtaccaggc aggacccagc atggacatga      60
gggtccctgc tcagctcctg ggactcctgc tgctctggct cccaggtaag gagggaaaca     120
acaaaatttt tattcagcca gtgtagccac taatgcctgg cacttcagga aattcttctt     180
agaacattac taatcatgtg gatatgtgtt tttatgttcc taatatcaga taccagatgt     240
tacatccaga tgacccagtc tccatcctct ctgtctgcat ctgtgggaga cagagtcacc     300
atcacttgcc gagccagtca ggcattagc aattacttag cctggtatca gcagaaacca     360
gggaaggttc ccaagctcct gatttatgct gcatccactt tgcaatctgg ggtcccatcg     420
```

```
cggttcagtg gcagtggatc tgggacagat ttcactctta ccatcagcag cctgcagcct      480
gaagatgttg ccacctatta ctgtcaaaag tacaacagtc cccctccact tttcggcgga      540
gggaccaagg tggagatcaa acgtaagtgc actttcctaa tgttcctcac cgtttctgcc      600
tgatttgttt gcttttttcca ttttttcgct at                                  632

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence:primer

<400> SEQUENCE: 55
catacacagc catacatacg cgtgtggccg ctctgcctct ctcttgcagg tatggacagc      60
aagcgaaccg                                                            70

<210> SEQ ID NO 56
<211> LENGTH: 71
<212> TYPE: DNA
<213> ORGANISM: Artificial Sequence
<220> FEATURE:
<223> OTHER INFORMATION: Description of Artificial Sequence:primer

<400> SEQUENCE: 56
atcagggtga cccctacgtt acactcctgt caccaaggag tgggagggac tcagaagaac      60
tcgtcaagaa g                                                          71

<210> SEQ ID NO 57
<211> LENGTH: 419
<212> TYPE: DNA
<213> ORGANISM: Artificial Sequence
<220> FEATURE:
<223> OTHER INFORMATION: Description of Artificial Sequence:a gene
      encoding human immunoglobulin light chain constant region
      Clambda2 flanked by nucleotides derived from the
      chicken light chain gene.

<400> SEQUENCE: 57
catacacagc catacatacg cgtgtggccg ctctgcctct ctcttgcagg tcagcccaag      60
gctgccccct ccgtcactct gttcccgccc tcctctgagg agcttcaagc caacaaggcc     120
acactggtgt gtctcataag tgacttctac ccgggagccg tgacagtggc ttggaaagca     180
gatagcagcc ccgtcaaggc gggagtggag accaccacac cctccaaaca aagcaacaac     240
aagtacgcgg ccagcagcta tctgagcctg acgcctgagc agtggaagtc ccacagaagc     300
tacagctgcc aggtcacgca tgaagggagc accgtggaga agacagtggc ccctacagaa     360
tgttcatagt agtcccactg gggatgcaat gtgaggacag tggttcctca ccctccctg      419

<210> SEQ ID NO 58
<211> LENGTH: 416
<212> TYPE: DNA
<213> ORGANISM: Artificial Sequence
<220> FEATURE:
<223> OTHER INFORMATION: Description of Artificial Sequence:a VJ gene
      segment encoding a human VJ immunoglobulin
      polypeptide, with flanking sequences derived from
      chicken immunoglobulin DNA.

<400> SEQUENCE: 58
ttgccgtttt ctcccctctc tcctctccct ctccaggttc cctggtgcag tcagtgctga      60
ctcagccgcc ctcggtgtca gcagccccgg gacaagaagt cacgatctcc tgctccgggt     120
```

```
ctagtagcaa cattggcgat aatttcgtct cttggtacca gcagctgcct ggcactgccc    180
ctaagcttct gatctatgat aacaacaaga gaccctcggg catccctgac cgattctccg    240
gttccaaatc cggcacctca gccacattag gcatcactgg gctccaaacc ggcgacgagg    300
ctgactatta ctgtgggact tgggacagca gcctttctgt tggtatgttt gggggcggga    360
cacgcgtgac cgtcctaggt gagtcgctga cctcgtctcg gtctttcttc ccccat       416
```